(12) United States Patent
Wang et al.

(10) Patent No.: US 11,389,463 B2
(45) Date of Patent: Jul. 19, 2022

(54) ANTIVIRAL NUCLEOSIDE REVERSE TRANSCRIPTASE INHIBITOR

(71) Applicant: Shenzhen TargetRx, Inc., Guangdong (CN)

(72) Inventors: Yihan Wang, Guangdong (CN); Jiuyang Zhao, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 0 days.

(21) Appl. No.: 16/954,824

(22) PCT Filed: Dec. 4, 2018

(86) PCT No.: PCT/CN2018/119085
§ 371 (c)(1),
(2) Date: Jun. 17, 2020

(87) PCT Pub. No.: WO2019/120071
PCT Pub. Date: Jun. 27, 2019

(65) Prior Publication Data
US 2021/0093650 A1 Apr. 1, 2021

(30) Foreign Application Priority Data
Dec. 21, 2017 (CN) .......................... 201711395814.X

(51) Int. Cl.
| | | |
|---|---|---|
| *A61K 31/675* | (2006.01) | |
| *C07F 9/02* | (2006.01) | |
| *A61P 31/14* | (2006.01) | |
| *A61P 31/18* | (2006.01) | |
| *C07F 9/6561* | (2006.01) | |
| *A61P 31/22* | (2006.01) | |

(52) U.S. Cl.
CPC ............ *A61K 31/675* (2013.01); *A61P 31/14* (2018.01); *A61P 31/18* (2018.01); *A61P 31/22* (2018.01); *C07F 9/65616* (2013.01)

(58) Field of Classification Search
CPC .......................... C07F 9/65616; A61K 31/661
USPC ............................................. 514/81; 544/244
See application file for complete search history.

(56) References Cited

FOREIGN PATENT DOCUMENTS

| CN | 102786549 A | 11/2012 |
| CN | 103224530 A | 7/2013 |
| CN | 103242366 A | 8/2013 |

OTHER PUBLICATIONS

Siegler et al. "The prevalence of pre-exposure prophylaxis use and the pre-exposure prophylaxis-to-need ratio in the fourth quarter of 2017, United States," Annals of Epidemiology, 2018, vol. 28, pp. 841-849 (Year: 2018).*
Chinese First Office Action for Application No. 201811473082.6, dated Jun. 12, 2020.
International Search Report and Written Opinion for Application No. PCT/CN2018/119085, dated Feb. 20, 2019.
Giesler et al., Next-Generation Reduction Sensitive Lipid Conjugates of Tenofovir: Antiviral Activity and Mechanism of Release. J. Med. Chem. 2016;59:10244-10252. DOI: 10.1021/acs.jmedchem.6b01292.
Giesler et al., Reduction Sensitive Lipid Conjugates of Tenofovir: Synthesis, Stability, and Antiviral Activity. J. Med. Chem. 2016;59:7097-7110. DOI: 10.1021/acs.jmedchem.6b00428.

* cited by examiner

*Primary Examiner* — Shengjun Wang
(74) *Attorney, Agent, or Firm* — Wolf, Greenfield & Sacks, P.C.

(57) ABSTRACT

The present invention relates to a compound of a novel antiviral nucleoside reverse transcriptase inhibitor, a pharmaceutical composition containing the compound, and preparation and application of the compound. Specifically, disclosed in the present invention are a fused pyrimidine compound as represented by formula (I) and a pharmaceutical composition comprising the compound, or a pharmaceutically acceptable salt, stereoisomer, solvate, hydrate, crystal form, prodrug or isotopic derivative of the compound. The compound of the present invention can be used for treatment and/or prevention of infectious diseases caused by viruses, such as human immunodeficiency virus (HIV), hepatitis B virus (HBV).

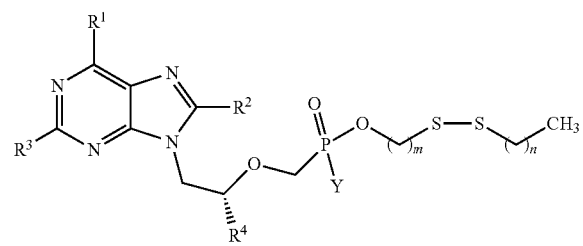

(I)

14 Claims, No Drawings

ANTIVIRAL NUCLEOSIDE REVERSE TRANSCRIPTASE INHIBITOR

CROSS REFERENCE TO RELATED APPLICATIONS

The present application is a national application of PCT/CN2018/119085 filed on Dec. 4, 2018, which claims the priority of the Chinese Patent Application No. 201711395814.X, filed on Dec. 21, 2017. The Chinese Patent Application No. 201711395814.X is incorporated herein by reference as part of the disclosure of the present application.

TECHNICAL FIELD

The present disclosure belongs to the pharmaceutical field. Specifically, the present disclosure relates to a class of novel nucleoside reverse transcriptase inhibitors, to pharmaceutical compositions containing the same, as well as to the preparation methods and the use thereof as antiviral drugs, especially the use for the treatment and/or prevention of patients having the human immunodeficiency virus (HIV) and/or hepatitis B virus (HBV).

BACKGROUND

A virus is a nucleic acid particle with an extremely simple structure. Most of them lack an enzyme system and can only rely on the host cell to proliferate by replicating their nucleic acid and protein, which are then assembled into a virus particle. Viral infections cause a variety of diseases and seriously endanger the health and life of human. According to certain statistics, about 60% of epidemic infectious diseases are caused by viral infections. So far, more than 3000 types of viruses have been discovered in the world, and new viruses are still being discovered. Among others, viral infections, such as caused by AIDS, hepatitis B/C, cytomegalovirus infection, etc. have high incidence and great danger.

Acquired Immune Deficiency Syndrome (AIDS) is an infectious disease caused by human immunodeficiency virus (HIV) infection. It is a fatal disease in which acquired defects in cellular immune function lead to serious random infection and/or provoke tumors. It is characterized by HIV specifically attacking T-helper lymphocytes, causing progressive destruction of the immune system function, leading to various opportunistic infections and the occurrence of related tumors. HIV virus, a type of retrovirus, is a lentivirus that infects cells of the human immune system. HIV is divided into two subtypes: HIV-1 and HIV-2. In terms of pathogenicity and infectivity, HIV-1 is stronger, and HIV-2 is basically only found in part areas of West Africa. Therefore, the current research on anti-HIV infection drugs mainly targets HIV-1. According to the latest report of United Nations Programme on HIV/AIDS: by the end of 2015, there are 36.7 million people infected with HIV, including 11 million deaths and 1.8 million children infected with HIV worldwide. AIDS is not only a medical problem, but also a serious social problem, which threatens human survival, development and stability. So there is still a need to develop novel high-efficient and low-toxic drugs and pharmaceutical compositions for the treatment and prevention of AIDS.

Hepatitis B is a worldwide epidemic infectious disease with high morbidity, strong infectivity and serious threat to human health. Currently, approximately 2 billion people worldwide have been infected with hepatitis B virus (HBV), of which 350 million people have become chronic HBV carriers, and approximately 1 million people worldwide each year died of liver diseases related to HBV infection. China is a high incidence area of hepatitis B. According to the 2002 National Epidemiological Survey of HBV Infectors, the prevalence of HBsAg is 9.09%, and about 120 million people carry HBV. Among them, there are more than 30 million patients with chronic hepatitis B (CHB). 15%-25% of patients with chronic hepatitis B are at risk of dying from HBV-related liver diseases, including chronic severe liver diseases, cirrhosis and hepatocellular carcinoma. The annual incidence of decompensation in cirrhosis is about 3%, and the cumulative incidence in 5 years is about 16%, of which 6%-15% can develop into hepatic cell carcinoma (HCC). The 5-year mortality rate of chronic hepatitis B, compensated and decompensated cirrhosis is 0%-2%, 14%-20%, and 70%-86%, respectively. More than 300,000 people died of hepatitis B-related complications in China every year. In addition, more than 90% of those infected with HBV during infancy become chronic HBV carriers, and they evolve into chronic hepatitis, cirrhosis, liver failure, and hepatocellular carcinoma when growing up. The continuous replication of HBV is an important factor that causes the continuous development of liver inflammation in patients with chronic hepatitis B, and leads to cirrhosis and liver cancer.

TDF (Tenofovir Disoproxil Fumarate) developed by Gilead was approved by the US Food and Drug Administration (FDA) for the first-line treatment of HIV and HBV infections in 2001 and 2008, respectively. TDF greatly improves cell penetration and oral availability, and is also recommended by the US Centers for Disease Control as a drug to prevent AIDS. The disadvantage of TDF is that it is easily hydrolyzed into TFV (Tenofovir) in plasma; on the other hand, for patients with impaired renal function, TDF may cause the risk of renal toxicity.

In order to reduce the metabolism of TDF to TFV in plasma, Gilead developed a more metabolically stable drug TAF (Tenofovir Alafenamide Fumarate). Two compound formulations of the TAF were approved by the FDA for the first-line treatment of HIV. TAF has also been successful in treating HBV, and was approved by the FDA in November 2016 for the treatment of HBV patients with compensatory liver disease.

TAF has two significant differences from TDF as follows: (1) the concentration of TFV in plasma metabolized by TAF is 90% lower than that of TDF, and (2) the concentration of TFV in immune cells metabolized by TAF is 4 times higher than that of TDF. Therefore, TAF can be used in clinical with very low doses, which significantly reduces the nephrotoxicity and bone toxicity caused by TDF.

Although TAF is used with a very low dose in clinical and has high anti-HIV and anti-HBV activity, TAF still has a small amount of hydrolysis during operation and in plasma. Therefore, there is still a clinical need to develop new compounds and specific metabolic manner, to further improve the stability of drugs in plasma and increase the concentration of drugs in tissue cells, thereby effectively reducing the clinical dose of drugs and further reducing the nephrotoxicity and bone toxicity of drugs, and better exerting the clinical effect of treatment of hepatitis B and AIDS.

SUMMARY OF THE INVENTION

The present disclosure provides a new nucleoside compound and a composition containing the same and the use thereof, wherein the compound has good anti-HIV and anti-HBV activity, and can be used in the treatment and/or prevention of HIV infection or/and HBV infection, and can greatly reduce the nephrotoxicity and bone toxicity caused by TDF or TAF.

In this regard, the present disclosure adopts the technical solutions as follows:

In the first aspect of the present disclosure, a compound represented by formula (I) is provided,

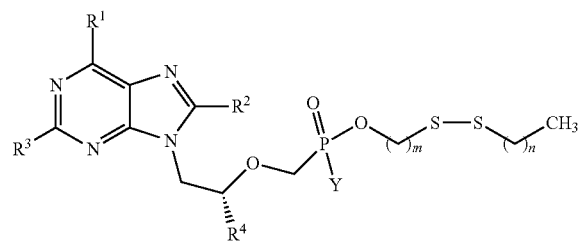

(I)

wherein, $R^1$ is selected from OH or $NR^5R^6$; wherein $R^5$ and $R^6$ are each independently selected from H, optionally substituted $C_1$-$C_6$ alkyl, optionally substituted $C_1$-$C_6$ heteroalkyl or optionally substituted $C_3$-$C_6$ carbocyclyl, or $R^5$ and $R^6$ together with the nitrogen atom to which they are attached form optionally substituted 3- to 6-membered heterocyclyl;

$R^2$ and $R^3$ are independently selected from H, $NH_2$, OH, halogen, CN, $NO_2$, optionally substituted $C_1$-$C_6$ alkyl, optionally substituted $C_1$-$C_6$ heteroalkyl, optionally substituted $C_1$-$C_6$ acyl, optionally substituted $C_2$-$C_6$ alkenyl, optionally substituted $C_2$-$C_6$ alkynyl, optionally substituted $C_3$-$C_7$ carbocyclyl, optionally substituted $C_3$-$C_7$ heterocyclyl, optionally substituted $C_6$-$C_{10}$ aryl or optionally substituted $C_5$-$C_{10}$ heteroaryl;

$R^4$ is selected from H, halogen, optionally substituted $C_1$-$C_6$ alkyl or optionally substituted $C_1$-$C_6$ heteroalkyl;

Y is selected from the following structures:

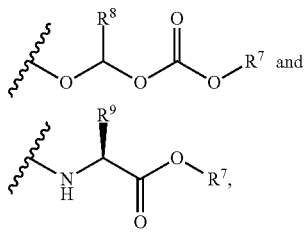

wherein $R^7$ is selected from optionally substituted $C_1$-$C_6$ alkyl, optionally substituted $C_1$-$C_6$ heteroalkyl, optionally substituted $C_1$-$C_6$ acyl, optionally substituted $C_2$-$C_6$ alkenyl, optionally substituted $C_2$-$C_6$ alkynyl, optionally substituted $C_3$-$C_7$ carbocyclyl, optionally substituted $C_3$-$C_7$ heterocyclyl, optionally substituted $C_6$-$C_{10}$ aryl or optionally substituted $C_5$-$C_{10}$ heteroaryl, as valency permits; $R^8$ and $R^9$ are independently selected from H, halogen, CN, $NO_2$, optionally substituted $C_1$-$C_6$ alkyl, optionally substituted $C_1$-$C_6$ heteroalkyl or optionally substituted $C_3$-$C_7$ carbocyclyl;

m is selected from 2 to 6;

n is selected from 10 to 21;

or a pharmaceutically acceptable salt, a stereoisomer, a solvate, a hydrate, a polymorph, a prodrug or an isotopic derivatives thereof.

In another aspect, the disclosure provides a pharmaceutical composition comprising a compound disclosed herein and a pharmaceutically acceptable excipient. In a particular embodiment, the compound disclosed herein is provided in the pharmaceutical composition in an effective amount. In a particular embodiment, the compound disclosed herein is provided in a therapeutically effective amount. In a particular embodiment, the compound disclosed herein is provided in a prophylactically effective amount.

In another aspect, the disclosure provides a pharmaceutical composition comprising a compound disclosed herein and a pharmaceutically acceptable excipient, further comprising other therapeutic agents.

In another aspect, the disclosure provides a kit containing a compound, or a pharmaceutically acceptable salt, a stereoisomer, a solvate, a hydrate, a polymorph, a prodrug or an isotopic variants thereof, and other therapeutic agents, and pharmaceutically acceptable carriers, adjuvants or vehicles.

In another aspect, the present disclosure provides a method of treating and/or preventing viral infections-related conditions in a subject in need thereof, said method comprising: administering to the subject an effective amount of the compound disclosed herein. In a specific embodiment, said viral infections are selected from: human immunodeficiency virus (HIV) infection, and hepatitis B virus (HBV) infection. In a specific embodiment, the compound is administered orally, subcutaneously, intravenously, or intramuscularly. In a specific embodiment, the compound is administered chronically.

Other objects and advantages of the present disclosure will be apparent to those skilled in the art from the following specific embodiments, examples and claims.

Definition

Chemical Definitions

Definitions of specific functional groups and chemical terms are described in more detail below.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$0_5$, $C_3$-$C_4$, $C_4$-$C_6$, $C_4$-$C_5$ and $C_5$-$C_6$ alkyl.

It should be understood that when described herein any of the moieties defined forth below may be substituted with a variety of substituents, and that the respective definitions are intended to include such substituted moieties within their scope as set out below. Unless otherwise stated, the term "substituted" is to be defined as set out below.

"$C_1$-$C_6$ alkyl" refers to a straight-chain or branched saturated hydrocarbon group having from 1 to 6 carbon atoms, and it is also referred to herein as "lower alkyl". In some embodiments, $C_{1-4}$ alkyl is particularly preferred. Examples of alkyl groups include, but are not limited to methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), n-hexyl ($C_6$) 3-methylhexyl ($C_6$), 2,2-dimethylpentyl ($C_6$) and 2,3-dimethylpentyl($C_6$). Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_1$-$C_6$ alkyl (e.g., —$CH_3$). In certain embodiments, the alkyl group is substituted $C_1$-$C_6$ alkyl.

"$C_1$-$C_6$ heteroalkyl" refers to an alkyl group, as defined herein, which further contains one or more (e.g., 1, 2, 3 or 4) heteroatoms (e.g., oxygen, sulfur, nitrogen, boron, silicon, phosphorus) in the parent carbon chain, wherein one or more heteroatoms are between adjacent carbon atoms in the parent carbon chain, and/or one or more heteroatoms are between the carbon atom and the parent molecule, that is, between the connection points. Unless otherwise stated, each heteroalkyl group is independently substituted, i.e., unsubstituted ("unsubstituted heteroalkyl") or substituted with one or more substituents ("substituted heteroalkyl"). In some embodiments, a heteroalkyl group is an unsubstituted $C_1$-$C_6$ heteroalkyl group. In some embodiments, a heteroalkyl group is a substituted $C_1$-$C_6$ heteroalkyl group. As a specific example, the $C_1$-$C_6$ heteroalkyl group includes $C_1$-$C_6$ alkoxy group, $C_1$-$C_6$ alkylthio group, $C_1$-$C_6$ alkylamino group and the like, which are defined in details as follows.

"$C_1$-$C_6$ alkoxy" refers to the group —OR wherein R is a substituted or unsubstituted $C_1$-$C_6$ alkyl group. In some embodiments, $C_1$-$C_4$ alkoxy group is particularly preferred. Specific $C_1$-$C_6$ alkoxy groups include, but are not limited to, methoxy, ethoxy, n-propoxy, isopropoxy, n-butoxy, tert-butoxy, sec-butoxy, n-pentyloxy, n-hexyloxy and 1,2-dimethylbutoxy.

"$C_1$-$C_6$ alkylthio" refers to the group —SR wherein R is optionally substituted $C_1$-$C_6$ alkyl. In some embodiments, $C_1$-$C_4$ alkylthio group is particularly preferred. Specifically, the $C_1$-$C_6$ alkylthio group includes, but is not limited to, methylthio, ethylthio, n-propylthio, isopropylthio, n-butylthio, tert-butylthio, sec-butylthio, n-pentylthio, n-hexylthio and 1,2-dimethylbutylthio.

"$C_1$-$C_6$ alkylamino" refers to the group —NHR or —$NR_2$, wherein R is optionally substituted $C_1$-$C_6$ alkyl. In some embodiments, $C_1$-$C_4$ alkylamino group is particularly preferred. Specifically, the $C_1$-$C_6$ alkylamino group includes, but is not limited to, methylamino, ethylamino, n-propylamino, isopropylamino, n-butylamino, t-butylamino, dimethylamino, methylethylamino and diethylamino.

"$C_1$-$C_6$ acyl" refers to the group —(=O)R, wherein R is optionally substituted $C_1$-$C_6$ alkyl. In some embodiments, $C_1$-$C_4$ acyl group is particularly preferred. Exemplary $C_1$-$C_6$ acyl groups include, but are not limited to, —(=O)$CH_3$, —(=O)$CH_2CH_3$, —(=O)$CH_2CH_2CH_3$ and —(=O)CH($CH_3$)$_2$.

"Halo" or "halogen" means fluorine (F), chlorine (Cl), bromine (Br) and iodine (I). In some embodiments, the halo group is F, —Cl or Br. In some embodiments, the halogen group is F or Cl. In some embodiments, the halogen group is F.

Thus, "$C_1$-$C_6$ haloalkyl" and "$C_1$-$C_6$ haloalkoxy" refer to the above "$C_1$-$C_6$ alkyl" and "$C_1$-$C_6$ alkoxy", which are substituted by one or more halo groups. In some embodiments, $C_1$-$C_4$ haloalkyl group is particularly preferred, and more preferably $C_1$-$C_2$ haloalkyl group. In some embodiments, $C_{1-4}$ haloalkoxy group is particularly preferred, and more preferably $C_1$-$C_2$ haloalkoxy group. Exemplary haloalkyl groups include, but are not limited to, —$CF_3$, —$CH_2F$, —$CHF_2$, —$CHFCH_2F$, —$CH_2CHF_2$, —$CF_2CF_3$, —$CCl_3$, —$CH_2Cl$, —$CHCl_2$, 2,2,2-trifluoro-1,1-dimethyl-ethyl, and the like. Exemplary haloalkoxy groups include, but are not limited to: —$OCH_2F$, —$OCHF_2$, —$OCF_3$, and the like.

"$C_3$-$C_7$ carbocyclyl" refers to a non-aromatic cyclic hydrocarbon group having from 3 to 7 ring carbon atoms and zero heteroatoms. In some embodiments, $C_5$-$C_6$ carbocyclyl is preferred, which is a non-aromatic cyclic hydrocarbon group having from 5 to 6 ring carbon atoms and zero heteroatoms. In some embodiments, $C_3$ carbocyclyl is preferred, which is a non-aromatic cyclic hydrocarbon group having 3 ring carbon atoms and zero heteroatoms. In some embodiments, $C_4$ carbocyclyl is preferred, which is a non-aromatic cyclic hydrocarbon group having 4 ring carbon atoms and zero heteroatoms. $C_5$ carbocyclyl is preferred, which is a non-aromatic cyclic hydrocarbon group having 5 ring carbon atoms and zero heteroatoms. $C_6$ carbocyclyl is preferred, which is a non-aromatic cyclic hydrocarbon group having 6 ring carbon atoms and zero heteroatoms. Carbocyclyl also includes ring systems wherein the carbocyclyl ring, as defined above, is fused, bridged or spiro-connected with one or more carbocyclyl, heterocyclyl, aryl or heteroaryl groups wherein the point of attachment is on the carbocyclyl ring, and in such instances, the number of carbons continue to designate the number of carbons in the carbocyclic ring system. Exemplary carbocyclyl groups include, but is not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cyclohexadienyl ($C_6$), as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_3$-$C_7$ carbocyclyl. In certain embodiments, the carbocyclyl group is a substituted $C_3$-$C_7$ carbocyclyl.

"$C_3$-$C_7$ heterocyclyl" refers to a radical of a 3- to 7-membered non-aromatic ring system having ring carbon atoms and 1 to 3 ring heteroatoms, wherein each heteroatom is independently selected from nitrogen, oxygen, sulfur, boron, phosphorus, and silicon, wherein the carbon, nitrogen, sulfur and phosphorus atoms may be present in the oxidation state, such as C(O), S(O), S(O)$_2$, P(O), and the like. In heterocyclyl groups that contain one or more nitrogen atoms, the point of attachment can be a carbon or nitrogen atom, as valency permits. In some embodiments, $C_4$-$C_7$ heterocyclyl is preferred, which is a radical of a 4- to 7-membered non-aromatic ring system having ring carbon atoms and 1 to 3 ring heteroatoms. In some embodiments, $C_4$-$C_6$ heterocyclyl is preferred, which is a radical of a 4- to 6-membered non-aromatic ring system having ring carbon atoms and 1 to 3 ring heteroatoms. In some embodiments, $C_5$-$C_6$ heterocyclyl is preferred, which is a radical of a 5- to 6-membered non-aromatic ring system having ring carbon atoms and 1 to 3 ring heteroatoms. In some embodiments, $C_5$ heterocyclyl is preferred, which is a radical of a 5-membered non-aromatic ring system having ring carbon atoms and 1 to 3 ring heteroatoms. In some embodiments, the above mentioned heterocyclyl contain 1 to 3 (more preferably 1 or 2) ring heteroatoms selected from nitrogen, oxygen and sulfur (preferably nitrogen and oxygen). Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted $C_3$-$C_7$ heterocyclyl. In certain embodiments, the heterocyclyl group is substituted $C_3$-$C_7$ heterocyclyl. Heterocyclyl also includes ring systems wherein the heterocyclyl ring, as defined above, is fused, bridged or spiro-connected with one or more carbocyclyl, heterocyclyl, aryl or heteroaryl groups, wherein the point of attachment is on the heterocyclyl ring; and in such instances, the number of ring members continue to designate the number of ring members in the heterocyclyl ring system. Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxathiolanyl, oxathiolyl (1,2-oxathiolyl, 1,3-oxathiolyl), dithiolanyl, dihydropyrazolyl, dihydroimidazolyl, dihydrothiazolyl, dihydroisothiazolyl, dihydrooxazolyl, dihydroisoxazolyl, dihydrooxadiazolyl and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, tetrahydropyridinyl, and thianyl. Exemplary 6-membered heterocyclyl groups containing two heteroatoms include, without limitation, dihydropyrazinyl, piperazinyl, morpholinyl, dithianyl, dioxanyl. Exemplary 6-membered heterocyclyl groups containing three heteroatoms include, without limitation, triazinanyl Exemplary 7-membered heterocyclyl groups containing one or two heteroatoms include, without limitation, azepanyl, diazepanyl, oxepanyl and thiepanyl. Exemplary 5-membered heterocyclyl groups fused to a 6-membered aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an 6-membered aryl ring (also referred to herein as a 6,6-bicyclic heterocyclic ring) include, without limitation, tetrahydroquinolinyl, tetrahydroisoquinolinyl, and the like.

"$C_6$-$C_{10}$ aryl" refers to a radical of a monocyclic or polycyclic (e.g., bicyclic or tricyclic) 4n+2 aromatic ring system (e.g., having 6, 10 π electrons shared in a cyclic array) having 6-10 ring carbon atoms and zero heteroatoms provided in the aromatic ring system. In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). "$C_6$-$C_{10}$ aryl" also includes ring systems wherein the aryl ring, as defined above, is fused with one or more carbocyclyl, heterocyclyl, aryl or heteroaryl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, mbicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-10}$ aryl. In certain embodiments, the aryl group is substituted $C_{6-10}$ aryl.

"$C_5$-$C_{10}$ heteroaryl" refers to a radical of a 5-10 membered monocyclic or bicyclic 4n+2 aromatic ring system (e.g., having 6 or 10π electrons shared in a cyclic array) having ring carbon atoms and 1-4 ring heteroatoms provided in the aromatic ring system, wherein each heteroatom is independently selected from nitrogen, oxygen and sulfur. In some embodiments, $C_5$ heteroaryl is preferred, which is a radical of a 5-membered monocyclic 4n+2 aromatic ring system (e.g., having 6π electrons shared in a cyclic array) having ring carbon atoms and 1-4 ring heteroatoms, wherein each heteroatom is independently selected from nitrogen, oxygen and sulfur. In some embodiments, $C_6$ heteroaryl is preferred, which is a radical of a 6-membered monocyclic 4n+2 aromatic ring system (e.g., having 6π electrons shared in a cyclic array) having ring carbon atoms and 1-4 ring heteroatoms, wherein each heteroatom is independently selected from nitrogen, oxygen and sulfur. In heteroaryl groups that contain one or more nitrogen atoms, the point of attachment can be a carbon or nitrogen atom, as valency permits. Heteroaryl bicyclic ring systems can include one or more heteroatoms in one or both rings. Heteroaryl includes ring systems wherein the heteroaryl ring, as defined above, is fused with one or more carbocyclyl, heterocyclyl, aryl or heteroaryl groups wherein the point of attachment is on the heteroaryl ring, and in such instances, the number of ring members continue to designate the number of ring members in the heteroaryl ring system. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted $C_5$-$C_{10}$ heteroaryl. In certain embodiments, the heteroaryl group is substituted $C_5$-$C_{10}$ heteroaryl. Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Alkyl, alkenyl, alkynyl, carbocyclyl, heterocyclyl, aryl, and heteroaryl groups, as defined herein, are optionally substituted groups. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary substituents on carbon atom include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), alkyl, haloalkyl, alkenyl, alkynyl, cathocyclyl, heterocyclyl, aryl, and heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$, each instance of R$^{aa}$ is, independently, selected from alkyl, haloalkyl, alkenyl, alkynyl, carbocyclyl, heterocyclyl, aryl, and heteroaryl, or two R$^{aa}$ groups are joined to form a heterocyclyl or heteroaryl ring, wherein each alkyl, alkenyl, alkynyl, cathocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)R$^{aa}$)$_2$, —P(=O)$_2$N(R$^{cc}$)$_2$, —P(=O)(NR$^{cc}$)$_2$, alkyl, haloalkyl, alkenyl, alkynyl, cathocyclyl, heterocyclyl, aryl, and heteroaryl, or two R$^{bb}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, alkyl, haloalkyl, alkenyl, alkynyl, carbocyclyl, heterocyclyl, aryl, and heteroaryl, or two R$^{cc}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, alkyl, haloalkyl, alkenyl, alkynyl, carbocyclyl, heterocyclyl, aryl, heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from alkyl, haloalkyl, alkenyl, alkynyl, carbocyclyl, aryl, heterocyclyl, and heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, alkyl, haloalkyl, alkenyl, alkynyl, carbocyclyl, heterocyclyl, aryl and heteroaryl, or two R$^{ff}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_2$-C$_6$ alkenyl, C$_2$-C$_6$ alkynyl, C$_3$-C$_7$ carbocyclyl, C$_6$-C$_{10}$ aryl, C$_3$-C$_7$ heterocyclyl, C$_5$-C$_{10}$ heteroaryl; or two geminal R$^{gg}$ substituents can be joined to form =O or =S; wherein X$^-$ is a counterion.

Exemplary substituents on nitrogen atoms include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, alkyl, perhaloalkyl, alkenyl, alkynyl, carbocyclyl, heterocyclyl, aryl, and heteroaryl, or two $R^{cc}$ groups attached to a nitrogen atom are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present disclosure include those derived from suitable inorganic and organic acids and inorganic and organic bases. Examples of pharmaceutically acceptable, nontoxic acid addition salts are salts of inorganic acids such as hydrochloric acid, hydrobromic acid, phosphoric acid, sulfuric acid and perchloric acid or salts of organic acids such as acetic acid, oxalic acid, maleic acid, tartaric acid, citric acid, succinic acid or malonic acid. Also included herein is the salt formed by using the conventional methods in the art such as ion exchange Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or elderly adult)) and/or a non-human animal, e g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound disclosed herein may vary depending on such factors as the desired biological endpoint, the pharmacokinetics of the compound, the disease being treated, the mode of administration, and the age, health, and condition of the subject. An effective amount encompasses therapeutically effective amount and prophylactically effective amount.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

"Combination" and related terms mean the simultaneous or sequential administration of a compound and other therapeutic agent of the present disclosure. For example, a compound disclosed herein may be administered simultaneously or sequentially with another therapeutic agent in separate unit dosage forms, or together with another therapeutic agent in a single unit dosage form.

The compound disclosed herein can be used in the treatment and/or prevention of viral infections. These diseases include, but are not limited to, human immunodeficiency virus (HIV) infection, hepatitis B virus (HBV) infection.

SPECIFIC EMBODIMENTS OF THE INVENTION

Compounds

In the present disclosure, "the compound disclosed herein" refers to the following compound of formula (I), a pharmaceutically acceptable salt, a stereoisomer, a solvate, a hydrate, a polymorph, a prodrug or an isotopic derivatives thereof.

In one embodiment, the present disclosure relates to a compound of formula (I):

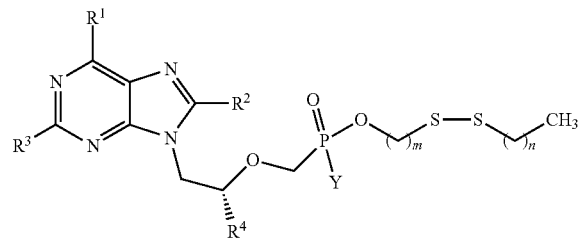

wherein, $R^1$ is selected from OH or $NR^5R^6$; wherein $R^5$ and $R^6$ are each independently selected from H, optionally substituted $C_1$-$C_6$ alkyl, optionally substituted $C_1$-$C_6$ heteroalkyl or optionally substituted $C_3$-$C_6$ carbocyclyl, or $R^5$ and $R^6$ together with the nitrogen atom to which they are attached form optionally substituted 3- to 6-membered heterocyclyl;

$R^2$ and $R^3$ are independently selected from H, $NH_2$, OH, halogen, CN, $NO_2$, optionally substituted $C_1$-$C_6$ alkyl, optionally substituted $C_1$-$C_6$ heteroalkyl, optionally substituted $C_1$-$C_6$ acyl, optionally substituted $C_2$-$C_6$ alkenyl, optionally substituted $C_2$-$C_6$ alkynyl, optionally substituted $C_3$-$C_7$ carbocyclyl, optionally substituted $C_3$-$C_7$ heterocyclyl, optionally substituted $C_6$-$C_{10}$ aryl or optionally substituted $C_5$-$C_{10}$ heteroaryl;

$R^4$ is selected from H, halogen, optionally substituted $C_1$-$C_6$ alkyl or optionally substituted $C_1$-$C_6$ heteroalkyl;

Y is selected from the following structures:

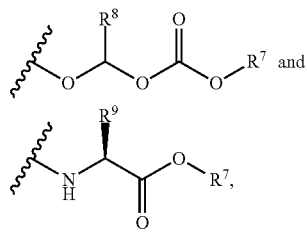

wherein $R^7$ is selected from optionally substituted $C_1$-$C_6$ alkyl, optionally substituted $C_1$-$C_6$ heteroalkyl, optionally substituted $C_1$-$C_6$ acyl, optionally substituted $C_2$-$C_6$ alkenyl, optionally substituted $C_2$-$C_6$ alkynyl, optionally substituted $C_3$-$C_7$ carbocyclyl, optionally substituted $C_3$-$C_7$ heterocyclyl, optionally substituted $C_6$-$C_{10}$ aryl or optionally substituted $C_5$-$C_{10}$ heteroaryl, as valency permits; $R^8$ and $R^9$ are independently selected from H, halogen, CN, $NO_2$, optionally substituted $C_1$-$C_6$ alkyl, optionally substituted $C_1$-$C_6$ heteroalkyl or optionally substituted $C_3$-$C_7$ carbocyclyl;

m is selected from 2 to 6;

n is selected from 10 to 21;

or a pharmaceutically acceptable salt, a stereoisomer, a solvate, a hydrate, a polymorph, a prodrug or an isotopic derivatives thereof.

Alternatively, in this embodiment, $R^1$ is $NR^5R^6$.

In the above embodiment of $R^1$, $R^5$ and $R^6$ are each independently selected from H, optionally substituted $C_1$-$C_6$ alkyl, optionally substituted $C_1$-$C_6$ heteroalkyl or optionally substituted $C_3$-$C_6$ carbocyclyl, or $R^5$ and $R^6$ together with the nitrogen atom to which they are attached form optionally substituted 3- to 6-membered heterocyclyl; alternatively, $R^5$ and $R^6$ are each independently selected from H, optionally substituted $C_1$-$C_6$ alkyl or optionally substituted $C_1$-$C_6$ heteroalkyl; alternatively, $R^5$ and $R^6$ are each independently selected from H or optionally substituted $C_1$-$C_6$ alkyl; yet alternatively, $R^5$ and $R^6$ are both H.

Alternatively, in this embodiment, $R^2$ and $R^3$ are independently selected from H, $NH_2$, OH, halogen, optionally substituted $C_1$-$C_6$ alkyl, optionally substituted $C_1$-$C_6$ heteroalkyl, optionally substituted $C_1$-$C_6$ acyl, optionally substituted $C_2$-$C_6$ alkenyl, optionally substituted $C_2$-$C_6$ alkynyl, optionally substituted $C_3$-$C_7$ carbocyclyl, optionally substituted $C_3$-$C_7$ heterocyclyl, optionally substituted $C_6$-$C_{10}$ aryl or optionally substituted $C_5$-$C_{10}$ heteroaryl; alternatively, $R^2$ and $R^3$ are independently selected from H, $NH_2$, OH, halogen, optionally substituted $C_1$-$C_6$ alkyl, optionally substituted $C_1$-$C_6$ heteroalkyl, optionally substituted $C_2$-$C_6$ alkenyl or optionally substituted $C_2$-$C_6$ alkynyl; alternatively, $R^2$ and $R^3$ are independently selected from H, $NH_2$, OH, halogen or optionally substituted $C_1$-$C_6$ alkyl; alternatively, $R^2$ and $R^3$ are independently selected from H, $NH_2$, OH or halogen; yet alternatively, $R^2$ and $R^3$ are independently selected from H, $NH_2$, OH or F; yet alternatively, $R^2$ and $R^3$ is independently selected from H or $NH_2$; still alternatively, $R^2$ and $R^3$ are both H.

Alternatively, in this embodiment, $R^4$ is selected from optionally substituted $C_1$-$C_6$ alkyl or optionally substituted $C_1$-$C_6$ heteroalkyl; alternatively, $R^4$ is optionally substituted $C_1$-$C_6$ alkyl; yet alternatively, $R^4$ is methyl.

Alternatively, in this embodiment, $R^7$ is selected from optionally substituted $C_1$-$C_6$ alkyl, optionally substituted $C_1$-$C_6$ heteroalkyl, optionally substituted $C_1$-$C_6$ acyl, optionally substituted $C_2$-$C_6$ alkenyl, optionally substituted $C_2$-$C_6$ alkynyl, optionally substituted $C_3$-$C_7$ carbocyclyl or optionally substituted $C_3$-$C_7$ heterocyclyl; alternatively, $R^7$ is selected from optionally substituted $C_1$-$C_6$ alkyl, optionally substituted $C_1$-$C_6$ heteroalkyl, optionally substituted $C_3$-$C_7$ carbocyclyl or optionally substituted $C_3$-$C_7$ heterocyclyl; alternatively, $R^7$ is selected from optionally substituted $C_1$-$C_6$ alkyl or optionally substituted $C_3$-$C_7$ carbocyclyl;

Yet alternatively, $R^7$ is selected from the following groups:

methyl, ethyl, n-propyl, isopropyl, n-butyl, s-butyl, isobutyl, t-butyl, n-pentyl, isopentyl, neopentyl, tert-pentyl, n-hexyl, 3-methylhexyl, 2,2-dimethylpentyl, 2,3-dimethylpentyl, cyclopropyl, cyclobutyl, cyclopentyl, cyclohexyl and cycloheptyl;

Most alternatively, $R^7$ is selected from the following groups:

methyl, ethyl, n-propyl, isopropyl, n-butyl, s-butyl, isobutyl, t-butyl, neopentyl, cyclopentyl and cyclohexyl.

Alternatively, in this embodiment, $R^8$ and $R^9$ are independently selected from H, halogen, optionally substituted $C_1$-$C_6$ alkyl, optionally substituted $C_1$-$C_6$ heteroalkyl or optionally substituted $C_3$-$C_7$ carbocyclyl; alternatively, $R^8$ and $R^9$ are independently selected from H, halogen or optionally substituted $C_1$-$C_6$ alkyl; yet alternatively, $R^8$ and $R^9$ are independently selected from H or optionally substituted $C_1$-$C_6$ alkyl; still alternatively, $R^8$ is H, and $R^9$ is methyl.

Alternatively, in this embodiment, m is selected from 2, 3, 4 or 5; alternatively, m is selected from 2, 3 or 4.

Alternatively, in this embodiment, n is selected from 11 to 19; yet alternatively, n is selected from 11, 13, 15 or 17.

In another embodiment, the compound of formula (I) is the following compound of formula (II):

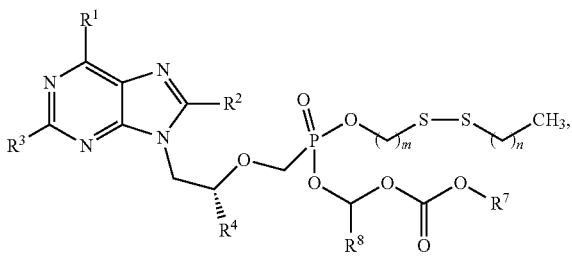

(II)

wherein $R^1$, $R^2$, $R^3$, $R^4$, $R^7$, $R^8$, m and n are as defined above.

In another embodiment, the compound of formula (I) is the following compound of formula (III):

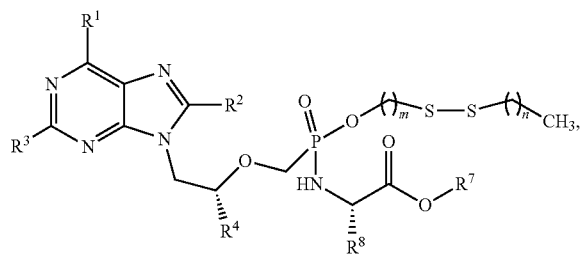

(III)

wherein $R^1$, $R^2$, $R^3$, $R^4$, $R^7$, $R^9$, m and n are as defined above.

In another embodiment, the present disclosure provides a compound of formula (I-1):

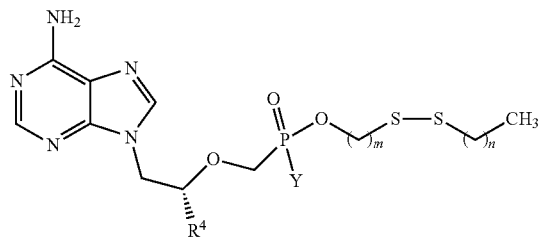

(I-1)

wherein, $R^4$ is selected from H or optionally substituted $C_1$-$C_6$ alkyl;

Y is selected from the following structures:

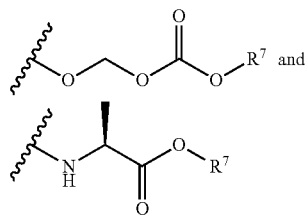

wherein, $R^7$ is selected from optionally substituted $C_1$-$C_6$ alkyl, optionally substituted $C_1$-$C_6$ heteroalkyl, optionally substituted $C_3$-$C_7$ carbocyclyl or optionally substituted $C_3$-$C_7$ heterocyclyl, as valency permits;

m is selected from 2 to 6;

n is selected from 10 to 21;

or a pharmaceutically acceptable salt, a stereoisomer, a solvate, a hydrate, a polymorph, a prodrug or an isotopic derivatives thereof.

In some embodiments, $R^4$ is selected from H or optionally substituted $C_1$-$C_4$ alkyl; alternatively, $R^4$ is H; alternatively, $R^4$ is methyl.

In some embodiments, Y is

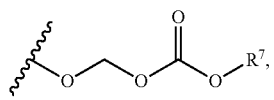

wherein, $R^7$ is selected from optionally substituted $C_1$-$C_6$ alkyl, optionally substituted $C_1$-$C_6$ heteroalkyl, optionally substituted $C_3$-$C_7$ carbocyclyl or optionally substituted $C_3$-$C_7$ heterocyclyl, as valency permits; alternatively, wherein $R^7$ is selected from optionally substituted $C_1$-$C_6$ alkyl or optionally substituted $C_3$-$C_7$ carbocyclyl; alternatively, wherein $R^7$ is selected from methyl, ethyl, n-propyl, isopropyl, n-butyl, s-butyl, isobutyl, t-butyl, n-pentyl, isopentyl, neopentyl, tert-pentyl, n-hexyl, 3-methylhexyl, 2,2-dimethylpentyl, 2,3-dimethylpentyl, cyclopropyl, cyclobutyl, cyclopentyl, cyclohexyl or cycloheptyl; alternatively, wherein $R^7$ is selected from methyl, ethyl, n-propyl, isopropyl, n-butyl, s-butyl, isobutyl, t-butyl, neopentyl, cyclopentyl or cyclohexyl; yet alternatively, wherein $R^7$ is isopropyl.

In some embodiments, Y is

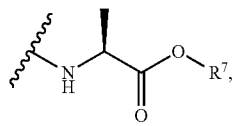

wherein, $R^7$ is selected from optionally substituted $C_1$-$C_6$ alkyl, optionally substituted $C_1$-$C_6$ heteroalkyl, optionally substituted $C_3$-$C_7$ carbocyclyl or optionally substituted $C_3$-$C_7$ heterocyclyl, as valency permits; alternatively, wherein $R^7$ is selected from optionally substituted $C_1$-$C_6$ alkyl or optionally substituted $C_3$-$C_7$ carbocyclyl; alternatively, wherein $R^7$ is selected from methyl, ethyl, n-propyl, isopropyl, n-butyl, s-butyl, isobutyl, t-butyl, n-pentyl, isopentyl, neopentyl, tert-pentyl, n-hexyl, 3-methylhexyl, 2,2-dimethylpentyl, 2,3-dimethylpentyl, cyclopropyl, cyclobutyl, cyclopentyl, cyclohexyl or cycloheptyl; alternatively, wherein $R^7$ is selected from methyl, ethyl, n-propyl, isopropyl, n-butyl, s-butyl, isobutyl, t-butyl, neopentyl, cyclopentyl or cyclohexyl; yet alternatively, wherein $R^7$ is isopropyl.

In some embodiments, m is selected from 2 to 6; alternatively, m is selected from 2, 3, 4 or 5; alternatively, m is selected from 2, 3 or 4; yet alternatively, m is 2.

In some embodiments, n is selected from 10 to 21; alternatively, n is selected from 11 to 19; alternatively, n is selected from 11, 13, 15 or 17; yet alternatively, n is 15.

In another embodiment, the compounds described herein (including formulae (I) to (III) and subsets thereof (for example, (I-1))) have a chirality at the phosphorus atom, and the configuration is selected from S-configuration, R-configuration or a mixture of S-configuration and R-configuration.
In another embodiment, the above compound of formulae (I) to (III) is the following compounds:
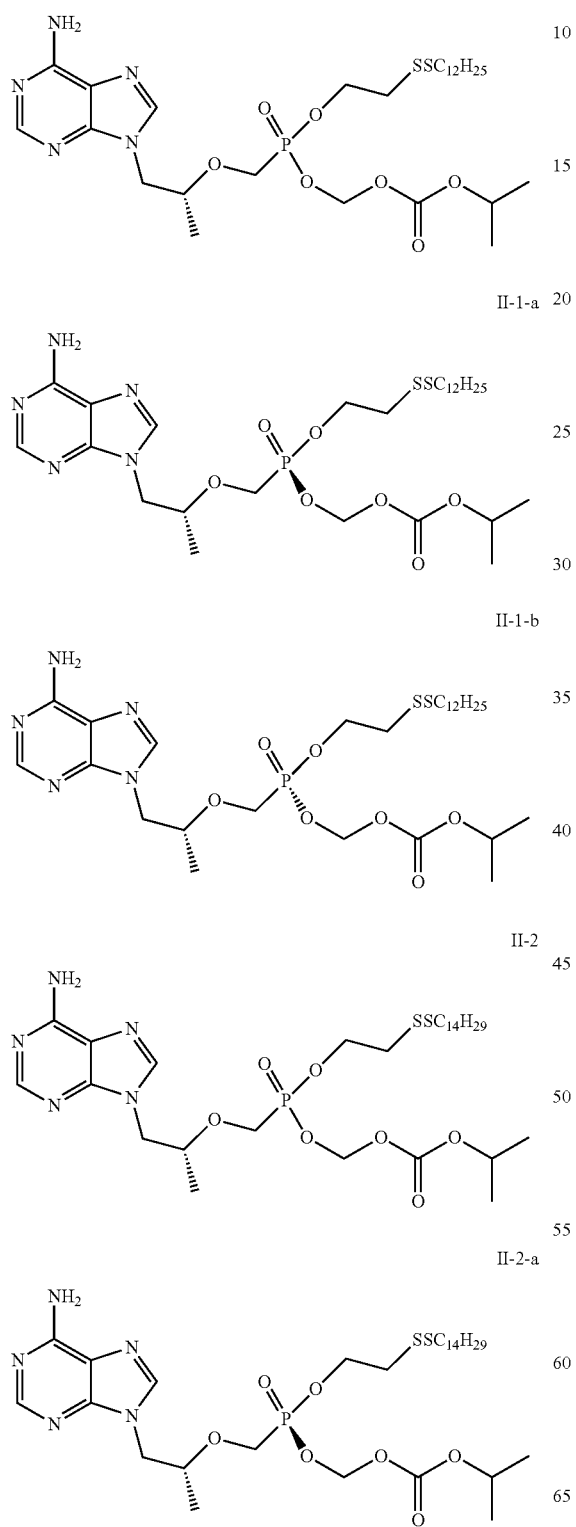
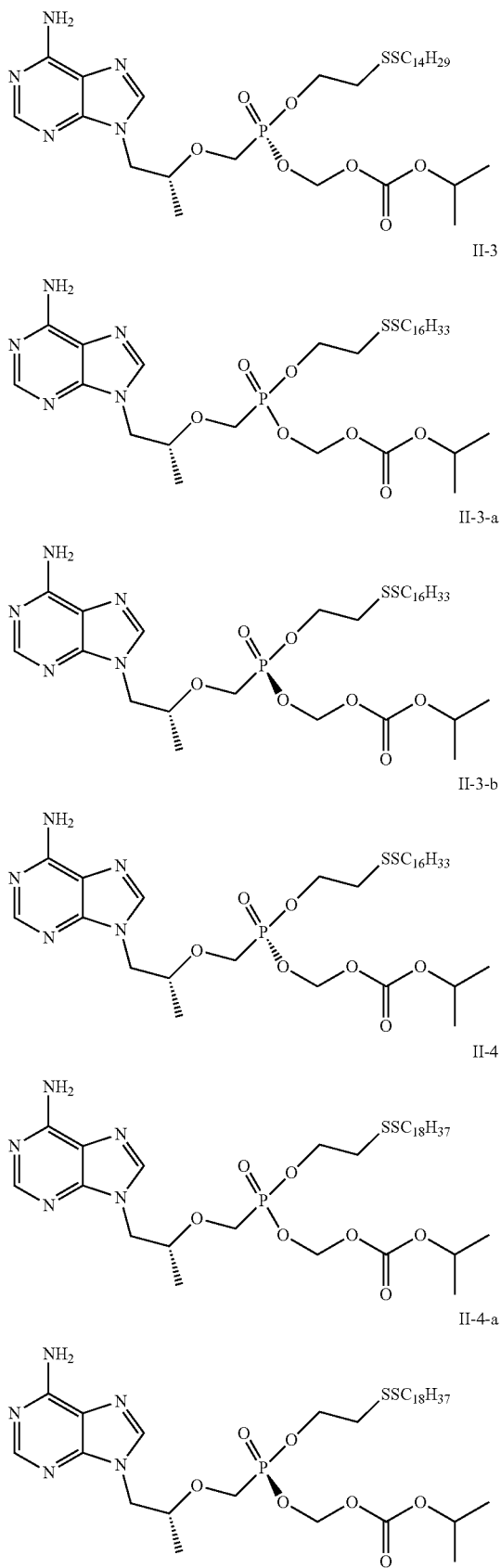

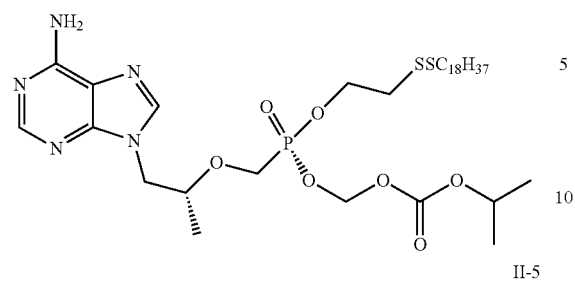
II-4-b
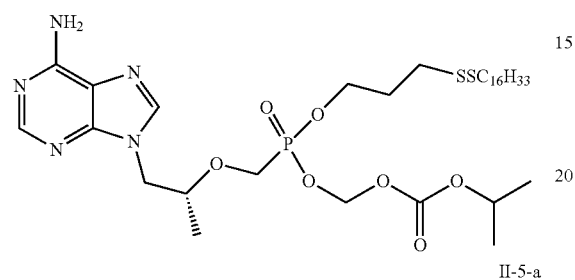
II-5
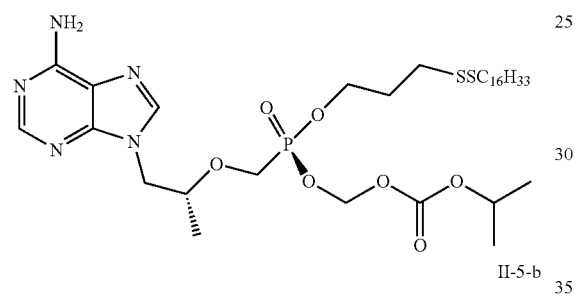
II-5-a
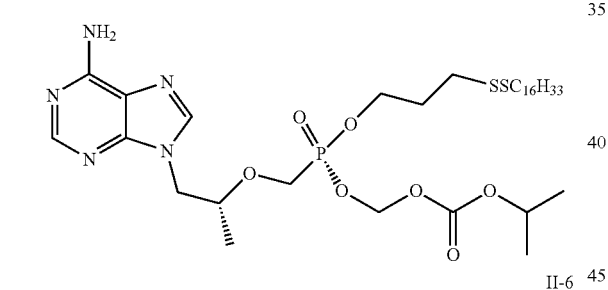
II-5-b
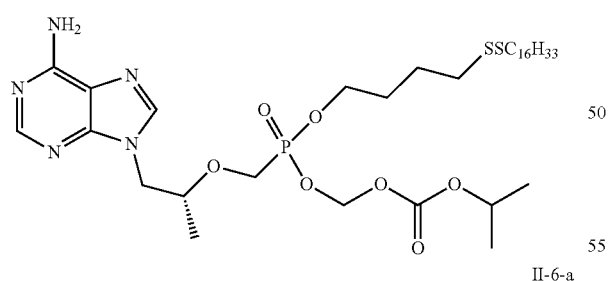
II-6
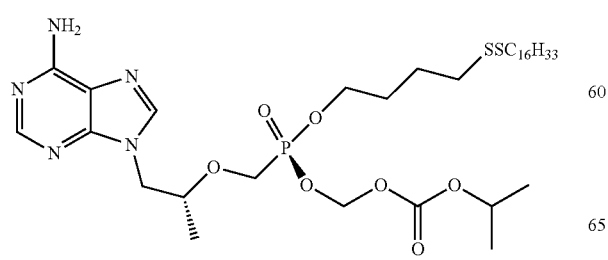
II-6-a
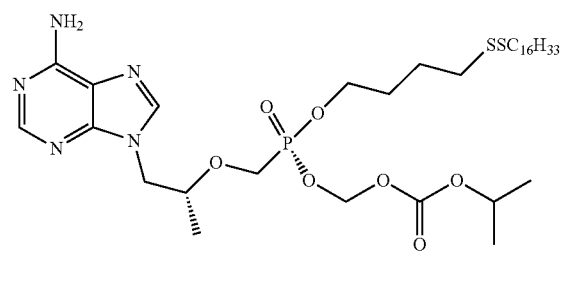
II-6-b
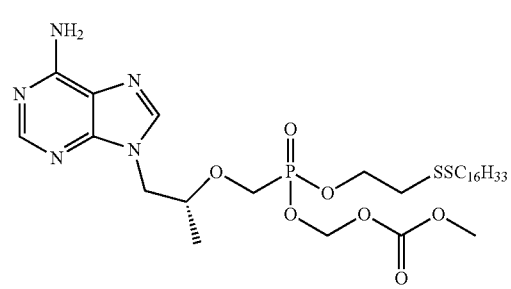
II-7
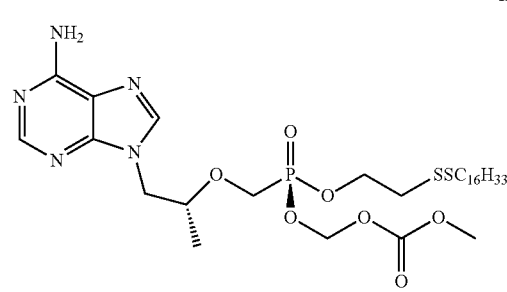
II-7-a
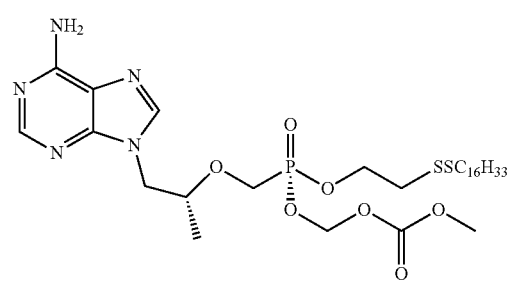
II-7-b
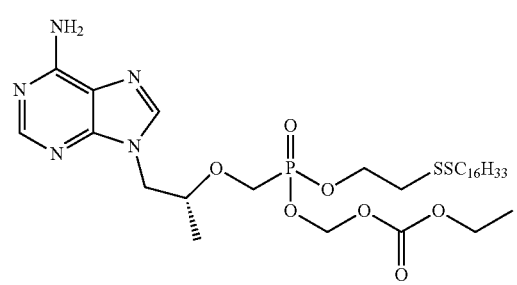
II-8

II-8-a
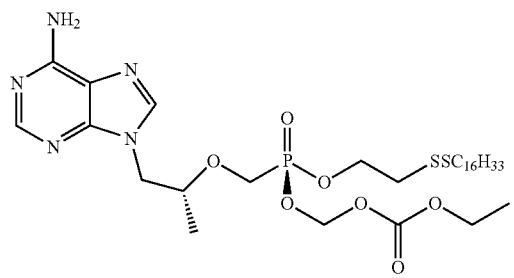
II-8-b
II-9
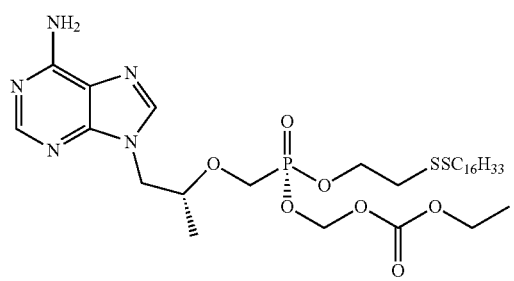
II-9-a
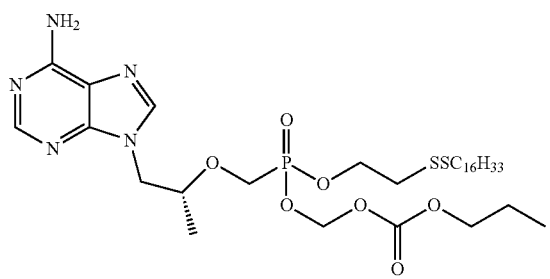
II-9-b
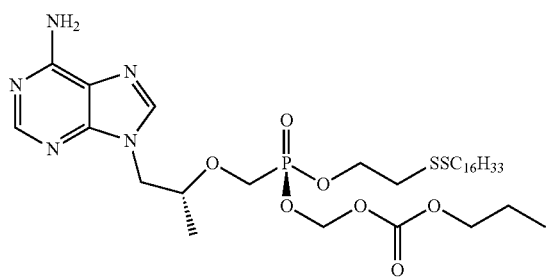
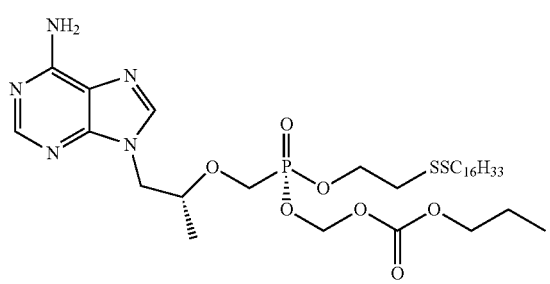
II-10
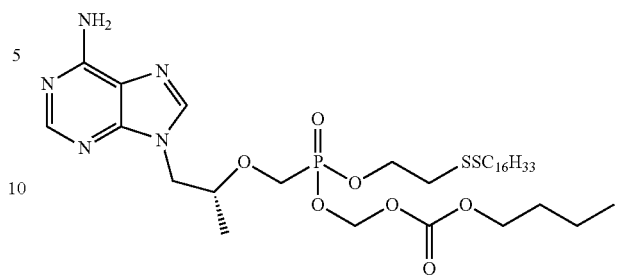
II-10-a
II-10-b
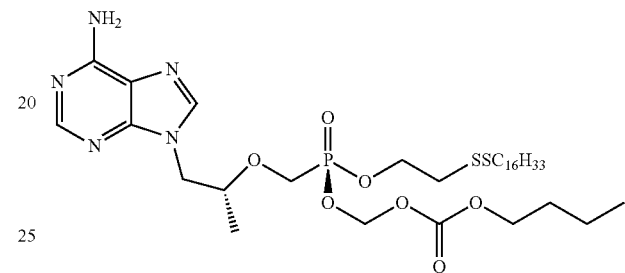
II-11
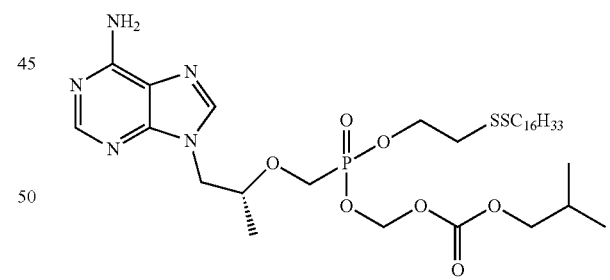
II-11-a
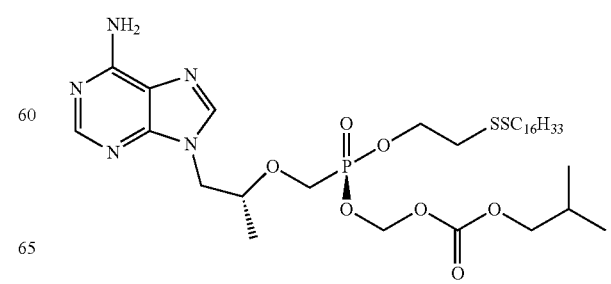

II-11-b
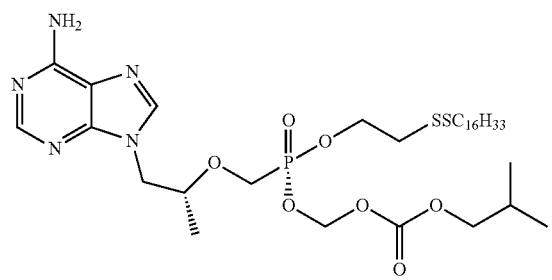
II-12
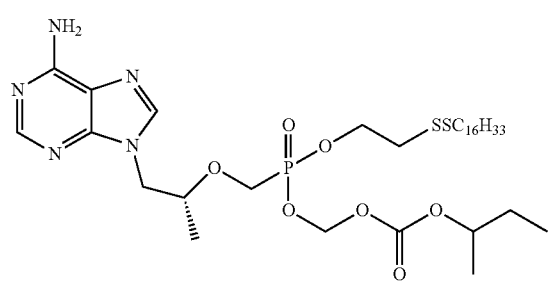
II-12-a
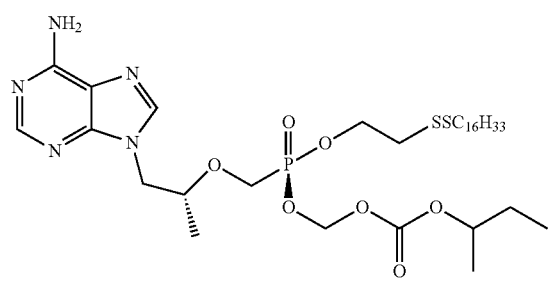
II-12-b
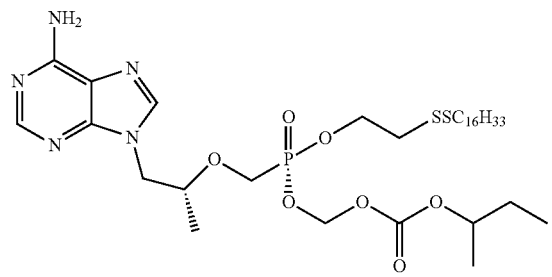
II-13
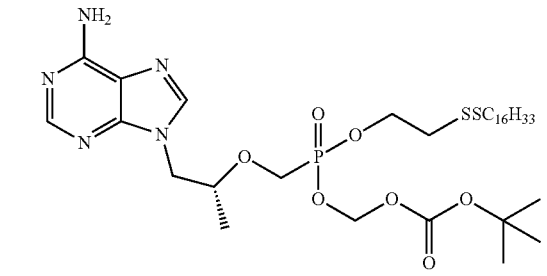
II-13-a
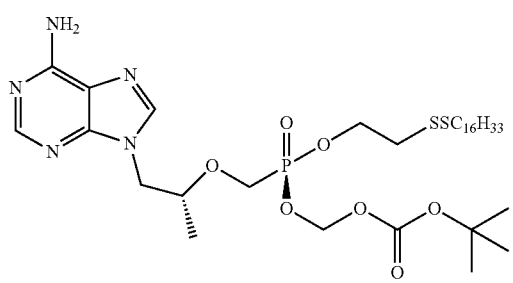
II-13-b
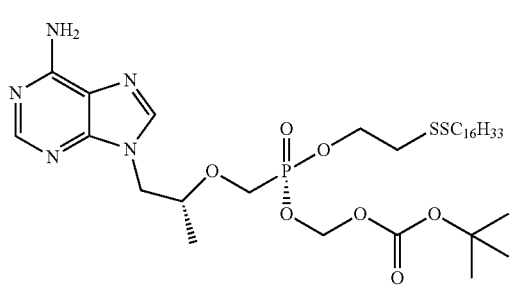
II-14
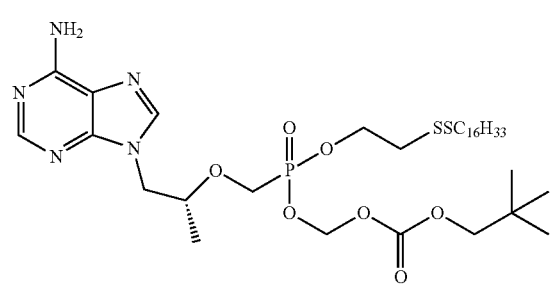
II-14-a
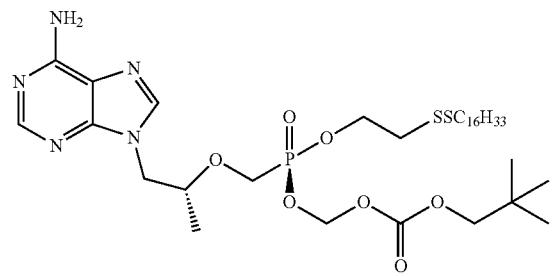
II-14-b
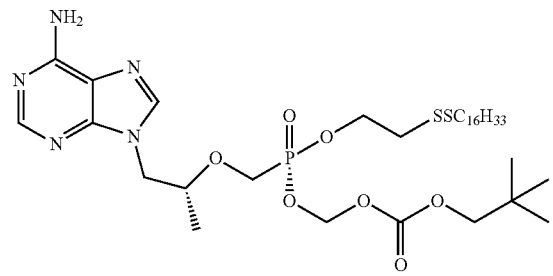

II-15
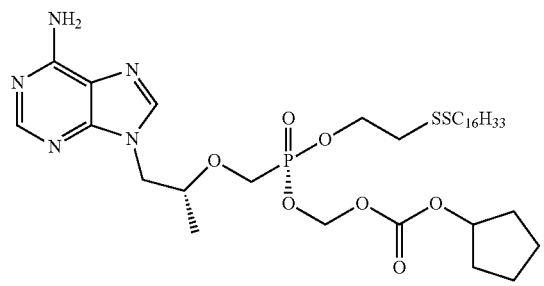
II-15-a
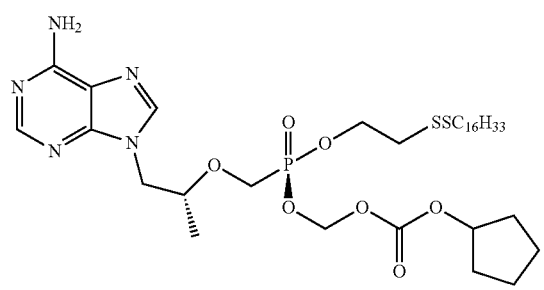
II-15-b
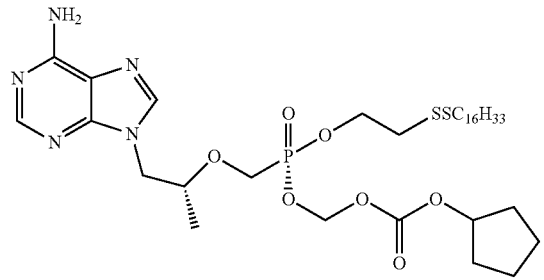
II-16
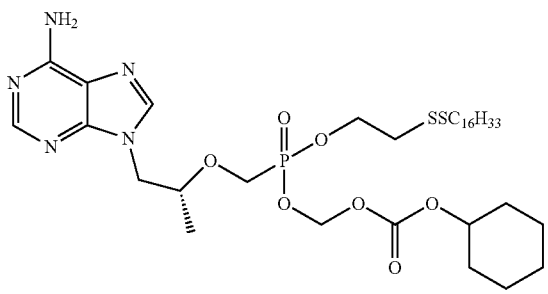
II-16-a
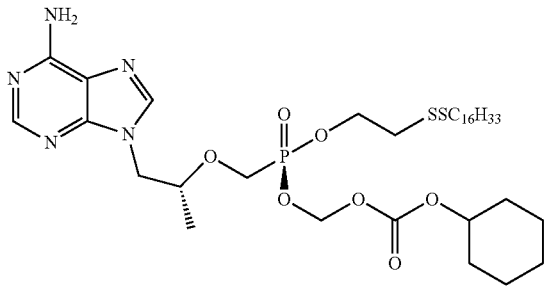
II-16-b
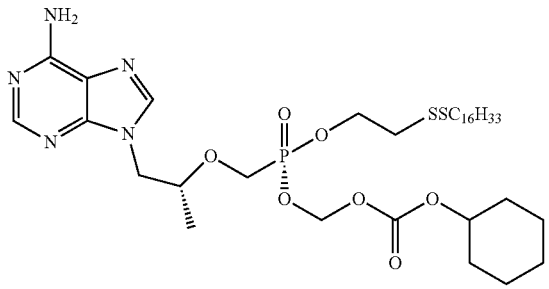
III-1
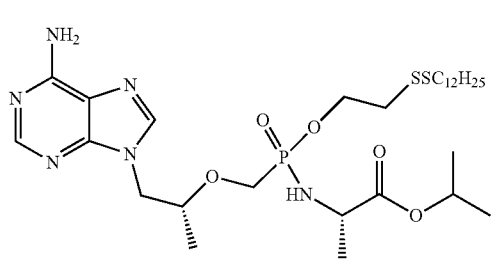
III-1-a
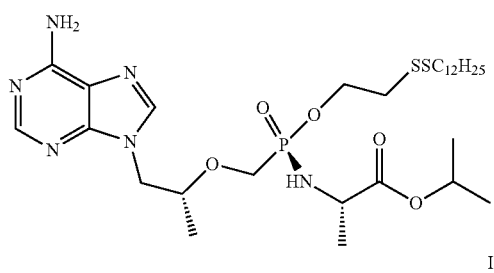
III-1-b
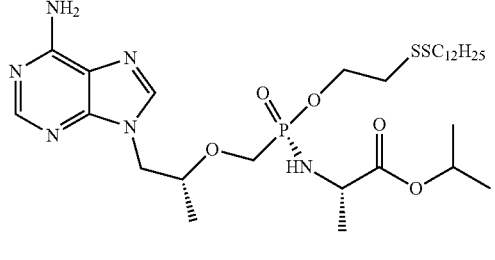
III-2
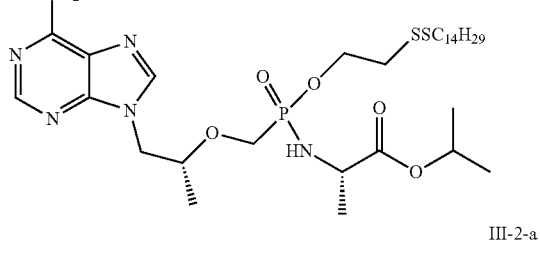
III-2-a
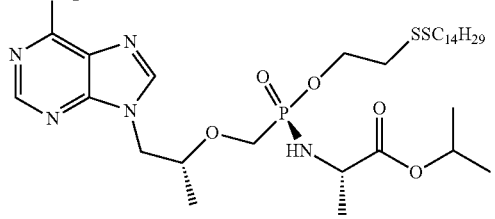

-continued
III-2-b
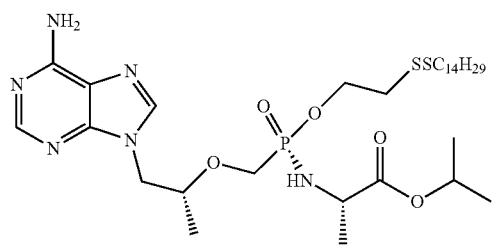
III-3
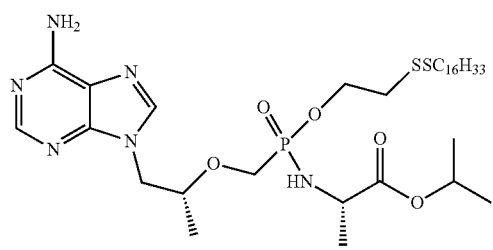
III-3-a
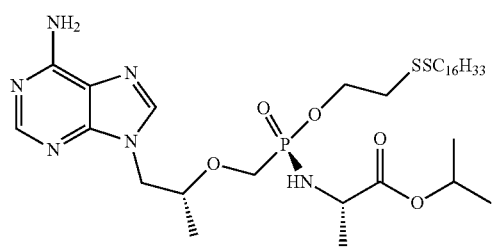
III-3-b
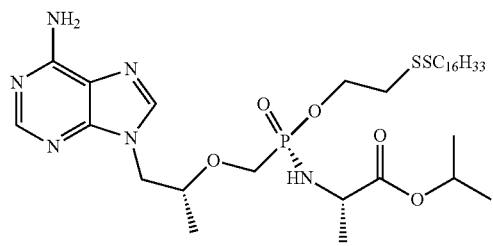
III-4
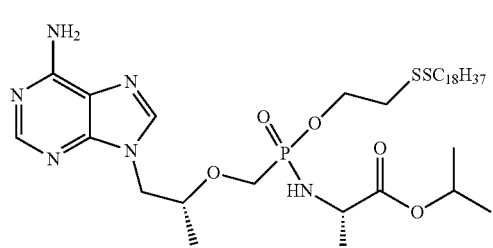
III-4-a
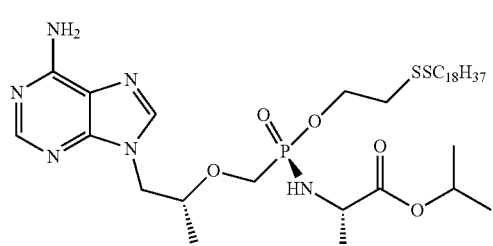
-continued
III-4-b
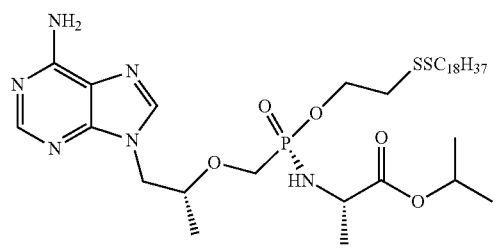
III-5
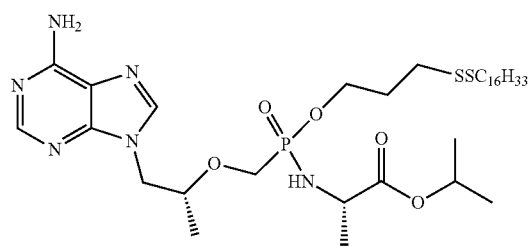
III-5-a
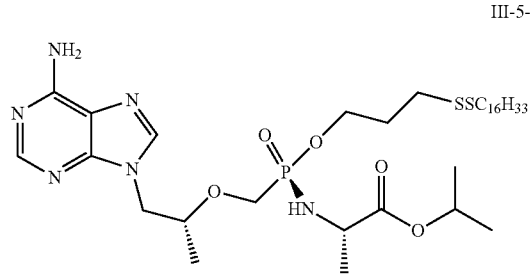
III-5-b
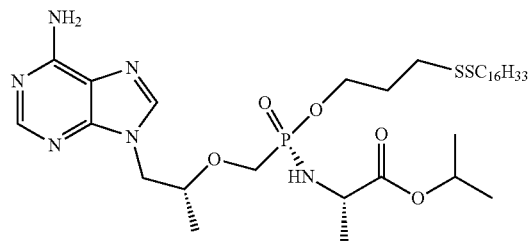
III-6
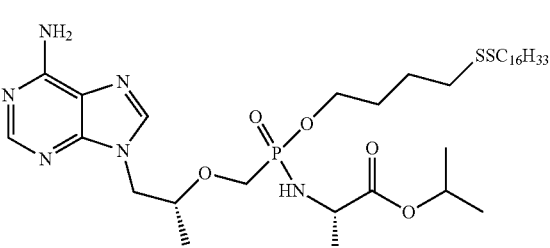
III-6-a
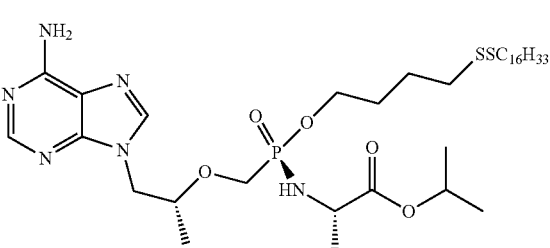

-continued

III-6-b

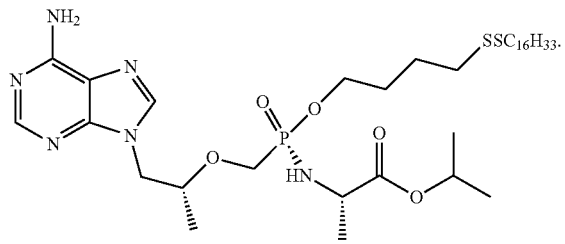

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer (such as cis- and trans-isomer), or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses.

Also disclosed herein are all suitable isotopic derivatives of the compounds disclosed herein. An isotopic derivative of a compound disclosed herein is defined as wherein at least one atom is replaced by an atom having the same atomic number but differing in atomic mass from the atomic mass typically found in nature. Examples of isotopes that can be incorporated into compounds disclosed herein include hydrogen, carbon, nitrogen, oxygen, fluorine, and chlorine isotopes, such as $^{2}H$, $^{3}H$, $^{13}C$, $^{14}C$, $^{15}N$, $^{17}O$, $^{18}O$, $^{18}F$, $^{31}F$, $^{32}P$, $^{35}S$ and $^{36}Cl$, respectively. Certain isotopic derivatives of the compounds disclosed herein, such as the radioisotopes of $^{3}H$ and $^{14}C$ are incorporated are useful in the tissue distribution experiments of drugs and substrates. Tritium, i.e., $^{3}H$, and carbon-14, i.e., $^{14}C$, are particularly preferred for their ease of preparation and detectability. In addition, substitution with heavier isotopes such as deuterium, i.e., $^{2}H$, has therapeutic advantages due to its good metabolic stability, for example, increased half-life in vivo or reduced dosage, and is thus preferable in some cases. Isotopic derivatives of the compounds disclosed herein can be prepared conventionally by the following procedures, for example by descriptive methods or by the preparations described in the Examples below, using appropriate reagents containing appropriate isotopes.

The compounds of the present disclosure or a pharmaceutically acceptable salt thereof may be in an amorphous or crystalline form. Furthermore, the compounds disclosed herein may exist in one or more crystalline forms. Accordingly, the disclosure includes within its scope all amorphous or crystalline forms of the compounds disclosed herein. The term "polymorph" refers to the crystalline form (or its salt, hydrate or solvate) of a compound in a specific crystal packing arrangement. All polymorphs have the same elemental composition. Different crystalline forms usually have different X-ray diffraction patterns, infrared spectra, melting points, density, hardness, crystal shape, photoelectric properties, stability, and solubility. Recrystallization solvent, crystallization rate, storage temperature and other factors can cause a crystalline form to dominate. Various polymorphs of the compound can be prepared by crystallization under different conditions.

Those skilled in the art will appreciate that many organic compounds can form complexes with solvents that react in or precipitate or crystallize from the solvent. These complexes are referred to as "solvates." When the solvent is water, the complex is referred to as a "hydrate." The disclosure encompasses all solvates of the compounds disclosed herein.

In addition, prodrugs are also included within the context of the present disclosure. The term "prodrug" as used herein refers to a compound which is converted in vivo to an active form thereof having a medical effect by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19(2) 115-130, each is incorporated herein by reference.

A prodrug is any covalently bonded carrier which, when administered to a patient, releases the compound of formula (I) in vivo. Prodrugs are typically prepared by modifying functional groups in such a way that the modification can be produced by conventional operations or cleavage in vivo to yield the parent compound. Prodrugs include, for example, compounds disclosed herein wherein a hydroxy, amino or sulfhydryl group is bonded to any group which, when administered to a patient, can be cleaved to form a hydroxy, amino or sulfhydryl group. Therefore, representative examples of prodrugs include, but are not limited to, acetate, formate, and benzoate derivatives of alcohol, mercapto, and amine functional groups of the compound of formula (I). Further, in the case of a carboxylic acid (—COOH), an ester such as a methyl ester, an ethyl ester or the like can be used. The ester itself may be active and/or may hydrolyze under conditions in human bodies. Suitable pharmaceutically acceptable hydrolysable in vivo ester groups include those groups which readily decompose in the human body to release the parent acid or a salt thereof.

Pharmaceutical Compositions, Formulations and Kits

In another aspect, the disclosure provides a pharmaceutical composition comprising a compound of the present disclosure (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that can be used in the compositions of the present disclosure include, but are not limited to, ion exchangers, alumina oxide, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agents, and a first and a second containers (eg, vials, ampoules, bottles, syringes, and/or dispersible packages or other materials) containing the compound disclosed herein or other therapeutic agents. In some embodiments, kits provided can also optionally include a third container containing a pharmaceutically acceptable excipient for diluting or suspending the compound disclosed herein and/or other therapeutic agent. In some embodiments, the compound disclosed herein provided in the first container and the other therapeutic agents provided in the second container is combined to form a unit dosage form.

The following formulation examples illustrate representative pharmaceutical compositions that may be prepared in accordance with this disclosure. The present disclosure, however, is not limited to the following pharmaceutical compositions.

Exemplary Formulation 1—Tablets: A compound of the present disclosure may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 2—Tablets: A compound of the present disclosure may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 3—Tablets: A compound of the present disclosure may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 4—Tablets: A compound of the present disclosure may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 5—Tablets: A compound of the present disclosure may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 6—Tablets: A compound of the present disclosure may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Exemplary Formulation 7—Tablets: A compound of the present disclosure may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 8—Capsules: A compound of the present disclosure may be admixed as a dry powder with a starch diluent in an approximate 1:1 weight ratio. The mixture is filled into 250 mg capsules (125 mg of active compound per capsule).

Exemplary Formulation 9—Liquid: A compound of the present disclosure (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 10—Injection: A compound of the present disclosure may be dissolved or suspended in a buffered sterile saline injectable aqueous medium to a concentration of approximately 5 mg/mL.

Administration

The pharmaceutical composition provided by the present disclosure can be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, infrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present disclosure may be further delivered using a variety of dosing methods. For example, in certain embodiments, the pharmaceutical composition may be given as a bolus, e.g., in order to raise the concentration of the compound in the blood to an effective level. The bolus dose depends on the target systemic level of the active ingredient passing through the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional dermal penetration ingredients to enhance the stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's *Pharmaceutical Sciences,* 17th edition, 1985, Mack Publishing Company, Easton, Pa., which is incorporated herein by reference.

The compounds of the present disclosure can also be administered in sustained release forms or from sustained release drug delivery systems. A description of representative sustained release materials can be found in Remington's Pharmaceutical Sciences.

The present disclosure also relates to the pharmaceutically acceptable formulations of a compound of the present disclosure. In one embodiment, the formulation comprises water. In another embodiment, the formulation comprises a cyclodextrin derivative. The most common cyclodextrins are α-, β- and γ-cyclodextrins consisting of 6, 7 and 8 α-1, 4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol. See, e.g., U.S. Pat. No. 5,376,645. In certain embodiments, the formulation comprises hexapropyl-β-cyclodextrin (e.g., 10-50% in water).

Combination Therapy

The compound disclosed herein or its composition can be administered in combination with other therapeutic agents to treat said diseases. Examples of the known therapeutic agent include, but are not limited to:

1) amprenavir, atazanavir, fosamprenavir, indinavir, lopinavir, ritonavir, nelfinavir, saquinavir, tipranavir, brecanavir, darunavir, TMC-126, TMC-114, mozenavir, JE-2147 (AG1776), L-756423, R00334649, KNI-272, DPC-681, DPC-684, GW640385X, DG17, GS-8374, PPL-100, DG35, and AG1859;

2) non-nucleoside inhibitors of HIV reverse transcriptase, for example capravirine, emivirine, delaviridine, efavirenz, nevirapine, (+) calanolide A, etravirine, GW5634, DPC-083, DPC-961, DPC-963, WIV-150, TMC-120, rilpivirine, BILR355BS, VPX840773, UK-453061, and RDEA806;

3) nucleoside inhibitors of HIV reverse transcriptase, for example zidovudine, emtricitabine, didanosine, stavudine (d4T), zalcitabine (ddC), lamivudine (3TC), abacavir, amdoxovir, elvucitabine, alovudine, MIV-210, racivir, D-d4FC, phosphazide, fozivudine tidoxil, apricitibine (AVX754), GS-7340, KP-1461, and fosalvudine tidoxil;

4) nucleotide inhibitors of HIV reverse transcriptase, for example tenofovir alafenamide and adefovir dipivoxil;

5) HIV integrase inhibitors, for example curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir, L-870812, and L-870810, raltegravir, elvitegravir, BMS-538158, GSK364735C, BMS-707035, MK-2048, and BA011;

6) gp41 inhibitors, for example enfuvirtide, sifuvirtide, FB006M, and TRI-1144;

7) CXCR4 inhibitors, for example AMD-070;

8) entry inhibitors, for example SP01A;

9) gp120 inhibitors, for example BMS-488043 or BlockAide/CR;

10) G6PD and NADH-oxidase inhibitors, for example immunitin;

11) CCR5 inhibitors, for example aplaviroc, vicriviroc, maraviroc, PRO-140, INCB15050, PF-233798, and CCR5mAb004;

12) other drugs for treating HIV, for example BAS-100, SPI-452, REP9, SP-01A, TNX-355, DES6, ODN-93, ODN-112, VGX-1, PA-457 (bevirimat), Ampligen, HRG214, Cytolin, VGX-410, KD-247, AMZ0026, CYT99007A-221HIV, DEBIO-025, BAY50-4798, MDX010 (ipilimumab), PBS119, ALG889, and PA-1050040 (PA-040);

13) interferons, for example pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta;

14) ribavirin analogs, for example rebetol, copegus, and viramidine (taribavirin);

15) NS5b polymerase inhibitors, for example NM-283, valopicitabine, R1626, PSI-6130 (R1656), HCV-796, BILB1941, XTL-2125, MK-0608, NM-107, R7128 (R4048), VCH-759, PF-868554, and GSK625433;

16) NS3 protease inhibitors, for example SCH-503034 (SCH-7), VX-950 (telaprevir), BILN-2065, BMS-605339, and ITMN-191;

17) alpha-glucosidase 1 inhibitors, for example MX-3253 (celgosivir) and UT-231B;

18) hepatoprotectants, for example IDN-6556, ME3738, LB-84451, and MitoQ;

19) non-nucleoside inhibitors of HCV, for example benzimidazole derivatives, benzo-1,2,4-thiadiazine derivatives, phenylalanine derivatives, A-831, GS-9190 and A-689; and 20) other drugs for treating HCV, for example zadaxin, nitazoxanide, BIVN-401 (virostat), PYN-17 (altirex), KPE02003002, actilon, KRN-7000, civacir, GI-5005, ANA-975, XTL-6856, ANA971, NOV-205, tarvacin, EHC-18, NIM811, DEBIO-025, VGX-410C, EMZ-702, AVI4065, Bavituximab, Oglufanide, and VX-497 (merimepodib).

Those other active agents can be administered separately from the composition containing the compound disclosed herein as part of a multiple-dose regimen. Alternatively, those active agents may be part of a single dosage form, mixed with the compound disclosed herein in a single composition. f administered as part of a multiple dosing regimen, the two active agents can be provided simultaneously, sequentially, or separated from each other for a period of time (usually within 5 hours of each other).

Treatment

The present disclosure provides a method of treating and/or preventing viral infections or a method of treating diseases, which comprises the steps of: administering to a subject in need of such treatment the compound disclosed herein, or a pharmaceutically acceptable salt, a stereoisomer, a solvate, a hydrate, a polymorph, a prodrug or an isotopic derivatives thereof, or pharmaceutical composition disclosed herein.

The compound disclosed herein can treat and/or prevent viral infections, including, but are not limited to human immunodeficiency virus (HIV) infection, hepatitis B virus (HBV) infection.

EXAMPLES

The following examples aim to provide those skilled in the art with a complete disclosure and description of how to perform, prepare, and evaluate the methods and compounds herein, and are intended to merely exemplify the invention and not to limit the scope of the invention as deemed by the inventor.

The Method of Synthesis

The compound disclosed herein can be prepared according to conventional methods in the art, using suitable reagents, raw materials, and purification methods known to those skilled in the art.

The preparation method of the compound of formula (I) disclosed herein is described in more detail below, but these specific methods do not constitute any limitation to the present invention. The compound disclosed herein can also be conveniently prepared by optionally combining various synthetic methods described in this specification or known in the art, and such combinations can be easily performed by those skilled in the art.

Generally, in the preparation, each reaction is usually carried out in an inert solvent at room temperature to reflux temperature (such as 0° C. to 100° C., preferably 0° C. to 80° C.). The reaction time is usually 0.1 hour to 60 hours, preferably 0.5 to 24 hours.

Example 1

(R)-9-{2-[(dodecyldisulfanylethyl)(isopropylcarbonatemethyl)phosphorylmethoxy]propyl}adenine (Compound T-1)

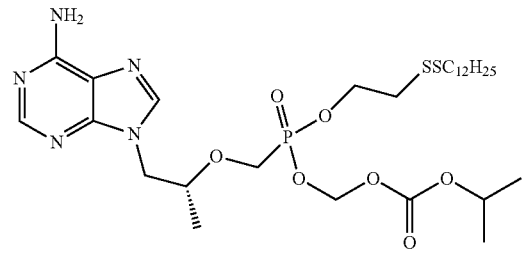

The following synthetic route was used for the synthesis:

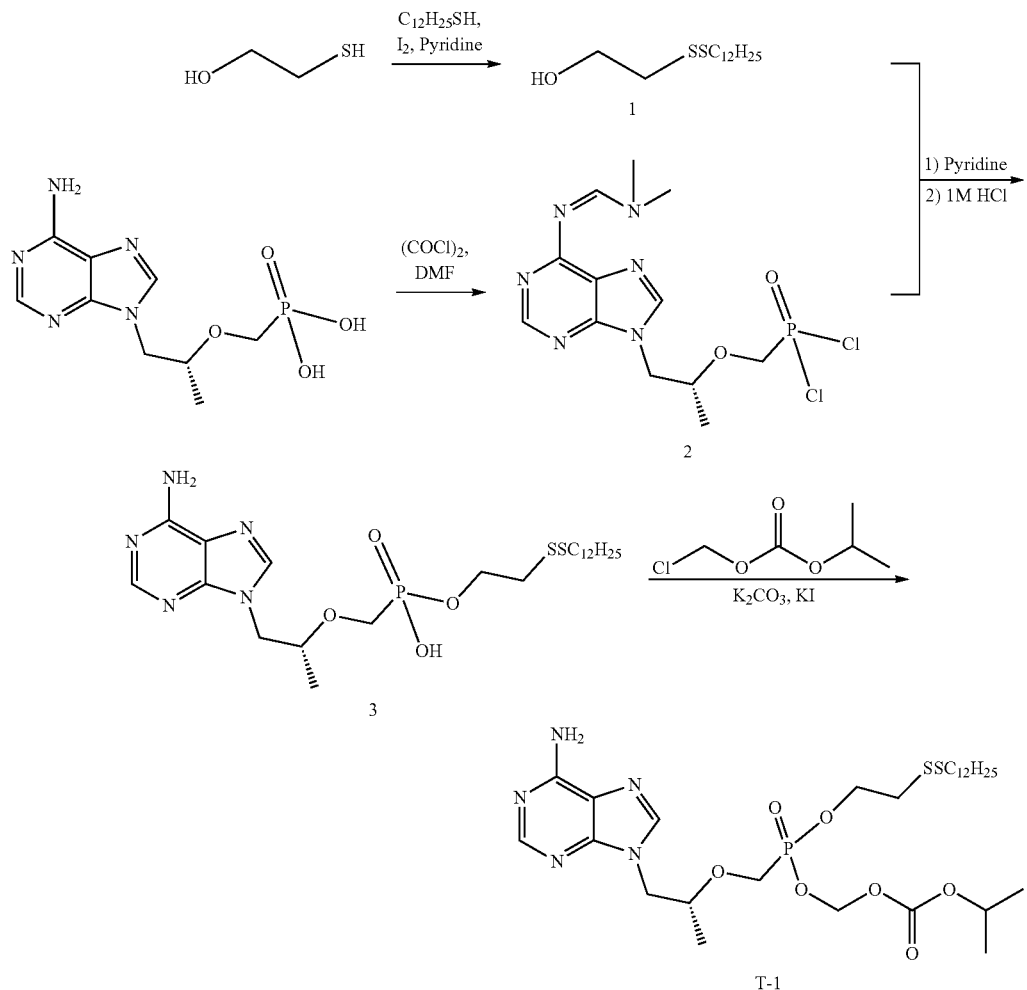

Step 1: Synthesis of 2-(dodecyldisulfanyl)ethanol (Compound 1)

To a reaction flask were added 2-mercaptoethanol (780 mg, 10 mmol), and n-dodecanethiol (2.02 g, 10 mmol), which were dissolved in 35 ml anhydrous methanol and 35 ml anhydrous dichloromethane. Pyridine (1.58 g, 20 mmol) was added to the mixture. Under the nitrogen protection, elemental iodine (2.54 g, 10 mmol) was added to the mixture in portions, and the reaction was stirred at room temperature for 2-5 hours after the addition was completed. Insoluble material was filtered off upon TLC detection showed the reaction was completed, and the filtrate was concentrated to dryness. The residue was dissolved in a small amount of dichloromethane, washed with saturated brine, concentrated, purified by column chromatography, and dried in vacuo to afford 1.13 g of a product in a yield of 40.6%.

Step 2: Synthesis of (R)-(1-(6-((dimethylamino)methyleneamino)-9H-purin-9-yl)propan-2-yloxy)methylphosphonic dichloride (Compound 2)

To a reaction flask were added (R)-(1-(6-((dimethylamino)methyleneamino)-9H-purin-9-yl)propan-2-yloxy)methylphosphonic acid (tenofovir, 500 mg, 1.74 mmol) and anhydrous DMF (153 mg, 2.1 mmol), which were dissolved by adding 10 ml anhydrous dichloromethane. Under the nitrogen protection, 2 M oxalyl chloride (4.35 ml, 8.7 mmol) was added dropwise at room temperature. After the addition, the reaction was stirred for 3 hours until the reaction became clear, which was concentrated to remove the solvent and excess oxalyl chloride to afford 658 mg of a product in a yield of 100%, which was used in the next step directly without purification.

Step 3: Synthesis of (R)-9-{2-[(dodecyldithioethyl)phosphorylmethoxy]propyl}adenine (Compound 3)

To a reaction flask was added Compound 2 (658 mg, 1.74 mmol), which was dissolved by adding 10 ml anhydrous dichloromethane. Under the nitrogen protection, the reaction was cooled to 0° C., and Compound 1 (584.2 mg, 2.1 mmol) and pyridine (826 mg, 10.44 mmol) in anhydrous dichloromethane was slowly added to the mixture dropwise. After the addition, the reaction was reacted at the low temperature for 10 minutes and warmed to rt and reacted for 2 hours.

Upon MS monitoring showed the reaction was completed, the reaction was quenched by adding 1 M dilute hydrochloric acid (10 ml), and stirred overnight at room temperature. The organic phase was separated upon MS monitoring showed the reaction was completed. The aqueous phase was extracted 2-3 times with dichloromethane. The organic phase was combined, washed with saturated brine, concentrated, and purified by silica gel column chromatography to afford 758 mg of product in a yield of 79.6%. LC-MS (APCI): m/z=548.3 (M+1)$^+$.

Step 4: Synthesis of (R)-9-{2-[(dodecyldisulfanyl-ethyl)(isopropylcarbonatemethyl)phosphoryl-methoxy]propyl}adenine (Compound T-1)

To a reaction flask were added Compound 3 (228 mg, 0.417 mmol), chloromethyl isopropyl carbonate (316.7 mg, 2.08 mmol), potassium carbonate (287.5 mg, 2.08 mmol) and potassium iodide (34.8 mg, 0.21 mmol). 8 ml DMF was added into the mixture, which was heated to 60° C. overnight. The reaction was cooled to rt upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 103 mg of product in a yield of 37.2%. LC-MS(APCI): m/z=664.3 (M+1)$^+$. $^1$H NMR (400 MHz, CDCl$_3$) δ 8.33 (s, 1H), 8.01 (s, 1H), 6.03 (s, 2H), 5.61 (m, 2H), 4.92 (m, 1H), 4.40-4.12 (m, 4H), 3.92 (m, 2H), 3.68 (t, J=10.0 Hz, 1H), 2.85 (dt, J=19.2, 6.7 Hz, 2H), 2.65 (dd, J=11.8, 7.0 Hz, 2H), 1.64 (s, 2H), 1.33-1.22 (m, 27H), 0.84 (t, J=6.6 Hz, 3H).

Example 2

(R)-9-{2-[(tetradecyldisulfanylethyl)(isopropylcarbonatemethyl)phosphorylmethoxy]propyl}adenine (Compound T-2)

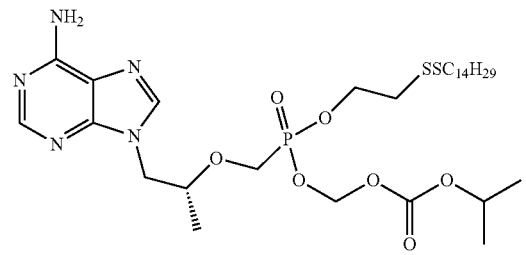

The following synthetic route was used for the synthesis:

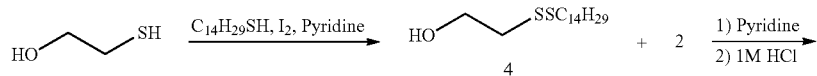

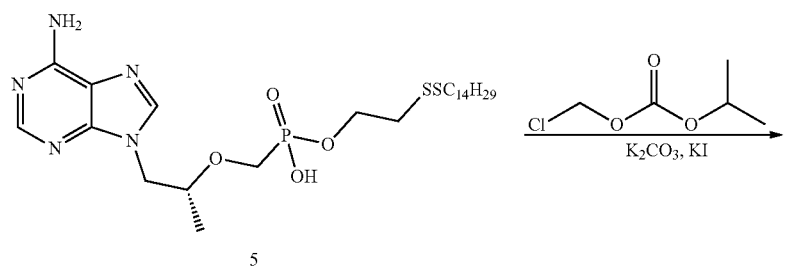

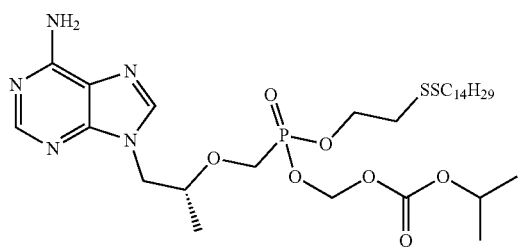

Step 1: Synthesis of 2-(tetradecyldisulfanyl)ethanol (Compound 4)

To a reaction flask were added 2-mercaptoethanol (780 mg, 10 mmol), and n-tetradecanethiol (2.3 g, 10 mmol), which were dissolved in 35 ml anhydrous methanol and 35 ml anhydrous dichloromethane. Pyridine (1.58 g, 20 mmol) was added to the mixture. Under the nitrogen protection, elemental iodine (2.54 g, 10 mmol) was added to the mixture in portions, and the reaction was stirred at room temperature for 2-5 hours after the addition was completed. Insoluble material was filtered off upon TLC detection showed the reaction was completed, and the filtrate was concentrated to dryness. The residue was dissolved in a small amount of dichloromethane, washed with saturated brine, concentrated, purified by column chromatography, and dried in vacuo to afford product 1.55 g in a yield of 50.6%.

Step 2: Synthesis of (R)-9-{2-[(tetradecyldisulfanylethyl)phosphorylmethoxy]propyl}adenine (Compound 5)

To a reaction flask was added Compound 2 (658 mg, 1.74 mmol), which was dissolved in 10 ml anhydrous dichloromethane Under the nitrogen protection, the reaction was cooled to 0° C., and a solution of Compound 4 (643 mg, 2.1 mmol) and pyridine (826 mg, 10.44 mmol) in anhydrous dichloromethane was slowly added to the mixture dropwise. After the addition, the reaction was reacted at the low temperature for 10 minutes and warmed to rt and reacted for 2 hours. Upon MS monitoring showed the reaction was completed, 1 M dilute hydrochloric acid (10 ml) was added to quench the reaction, which was stirred at room temperature overnight. The organic phase was separated upon MS monitoring showed the reaction was completed. The aqueous phase was extracted 2-3 times with dichloromethane. The organic phase was combined, washed with saturated brine, concentrated, and purified by silica gel column chromatography to afford 732 mg of product in a yield of 73.1%. LC-MS(APCI): m/z=576.2 (M+1)$^+$.

Step 3: Synthesis of (R)-9-{2-[(tetradecyldisulfanylethyl)(isopropylcarbonatemethyl)phosphorylmethoxy]propyl}adenine (Compound T-2)

To a reaction flask were added Compound 5 (300 mg, 0.52 mmol), chloromethyl isopropyl carbonate (395.3 mg, 2.6 mmol), potassium carbonate (359.3 mg, 2.6 mmol) and potassium iodide (43.2 mg, 0.26 mmol). 10 ml DMF was added to the mixture. The reaction was heated to 60° C. and reacted overnight, and cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 124 mg of product in a yield of 34.5%. LC-MS(APCI): m/z=692.7 (M+1)$^+$. $^1$H NMR (400 MHz, CDCl$_3$) δ 8.36 (s, 1H), 8.04 (s, 1H), 6.06 (s, 2H), 5.65 (dd, J=28.2, 8.9 Hz, 2H), 4.92 (m, 1H), 4.40-4.12 (m, 4H), 3.96 (m, 2H), 3.68 (t, J=10.0 Hz, 1H), 2.89 (dt, J=19.2, 6.7 Hz, 2H), 2.67 (dd, J=11.8, 7.0 Hz, 2H), 1.64 (s, 2H), 1.33-1.25 (m, 31H), 0.87 (t, J=6.6 Hz, 3H).

Example 3

(R)-9-{2-[(hexadecyldisulfanylethyl)(isopropylcarbonatemethyl)phosphorylmethoxy]propyl}adenine (Compound T-3)

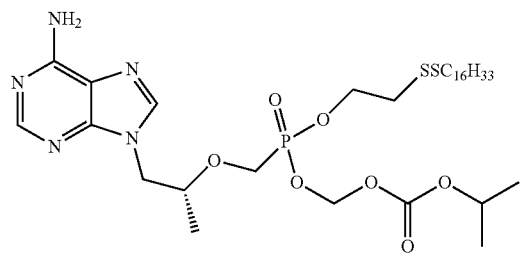

T-3

The following synthetic route was used for the synthesis:

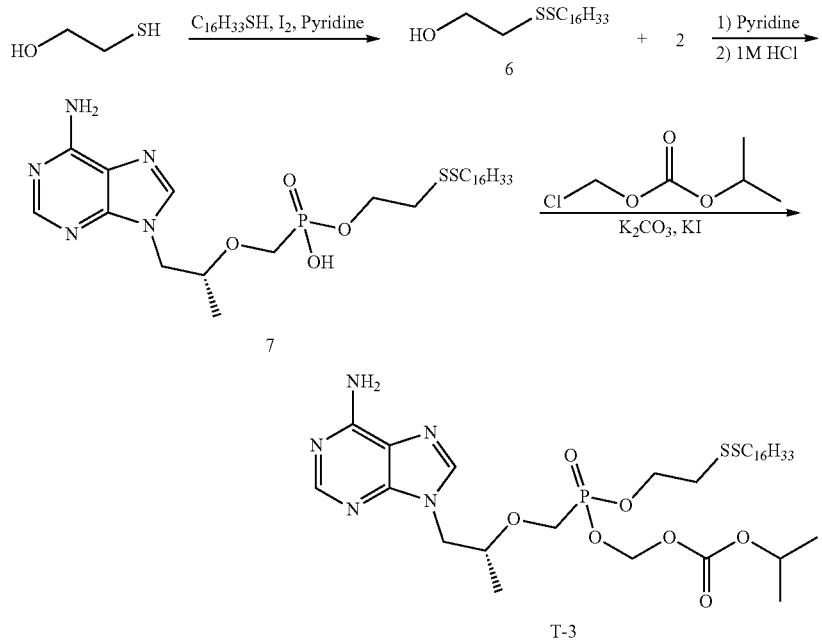

Step 1: Synthesis of 2-(hexadecyldisulfanyl)ethanol (Compound 6)

To a reaction flask were added 2-mercaptoethanol (780 mg, 10 mmol), and n-hexadecanethiol (2.58 g, 10 mmol), which were dissolved in 35 ml anhydrous methanol and 35 ml anhydrous dichloromethane. Pyridine (1.58 g, 20 mmol) was added to the mixture. Under the nitrogen protection, elemental iodine (2.54 g, 10 mmol) was added to the mixture in portions, and the reaction was stirred at room temperature for 2-5 hours after the addition was completed. Insoluble material was filtered off upon TLC detection showed the reaction was completed, and the filtrate was concentrated to dryness. The residue was dissolved in a small amount of dichloromethane, washed with saturated brine, concentrated, purified by column chromatography, and dried in vacuo to afford product 1.89 g in a yield of 56.6%.

Step 2: Synthesis of (R)-9-{2-[(hexadecyldisulfanylethyl)phosphorylmethoxy]propyl}adenine (Compound 7)

To a reaction flask was added Compound 2 (658 mg, 1.74 mmol), which was dissolved in 10 ml anhydrous dichloromethane Under the nitrogen protection, the reaction was cooled to 0° C., and a solution of Compound 6 (701.9 mg, 2.1 mmol) and pyridine (826 mg, 10.44 mmol) in anhydrous dichloromethane was added to the reaction dropwise. After the addition, the reaction was reacted at the low temperature for 10 minutes and warmed to rt and reacted for 2 hours. Upon MS monitoring showed the reaction was completed, 1 M dilute hydrochloric acid (10 ml) was added to quench the reaction, which was stirred at room temperature overnight. The organic phase was separated upon MS monitoring showed the reaction was completed, and the aqueous phase was extracted 2-3 times with dichloromethane. The organic phase was combined, washed with saturated brine, concentrated, and purified by silica gel column chromatography to afford 895 mg of product in a yield of 85.2%. LC-MS (APCI): m/z=604.5 (M+1)+.

Step 3: Synthesis of (R)-9-{2-[(hexadecyldisulfanylethyl)(isopropylcarbonatemethyl)phosphorylmethoxy]propyl}adenine (Compound T-3)

To a reaction flask were added Compound 7 (140 mg, 0.23 mmol), chloromethyl isopropyl carbonate (176.4 mg, 1.16 mmol), potassium carbonate (160.3 mg, 1.16 mmol) and potassium iodide (19.9 mg, 0.12 mmol). 5 ml DMF was added to the mixture. The reaction was heated to 60° C. and reacted overnight, and cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 45 mg of product in a yield of 27.2%. LC-MS(APCI): m/z=720.3 (M+1)+. $^1$H NMR (400 MHz, CDCl$_3$) δ 8.34 (s, 1H), 8.03 (s, 1H), 6.06 (s, 2H), 5.61 (dd, J=28.2, 8.9 Hz, 2H), 4.92 (m, 1H), 4.40-4.12 (m, 4H), 3.92 (m, 2H), 3.68 (t, J=10.0 Hz, 1H), 2.87 (dt, J=19.2, 6.7 Hz, 2H), 2.67 (dd, J=11.8, 7.0 Hz, 2H), 1.64 (s, 2H), 1.33-1.22 (m, 35H), 0.87 (t, J=6.6 Hz, 3H).

Example 4

(R)-9-{2-[(R)-(hexadecyldisulfanylethyl)(isopropylcarbonatemethyl)phosphorylmethoxy]propyl}adenine (Compound T-3-1)

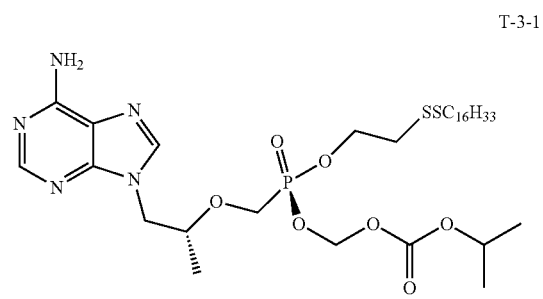

T-3-1

Compound T-3-1 was prepared according to the method described in Example 3, and was obtained by chiral column separation.

Example 5

(R)-9-{2-[(S)-(hexadecyldisulfanylethyl)(isopropylcarbonatemethyl)phosphorylmethoxy]propyl}adenine (Compound T-3-2)

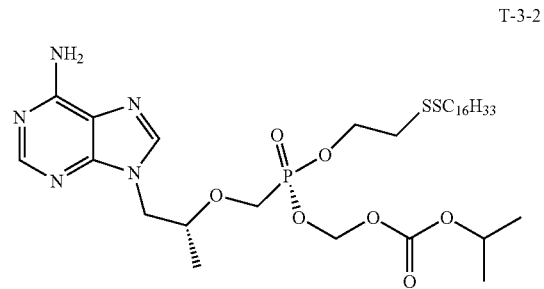

T-3-2

Compound T-3-2 was prepared according to the method described in Example 3, and was obtained by chiral column separation.

Example 6

(R)-9-{2-[(octadecyldisulfanylethyl)(isopropylcarbonatemethyl)phosphorylmethoxy]propyl}adenine (Compound T-4

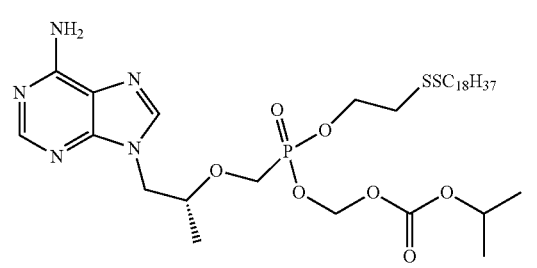

T-4

The following synthetic route was used for the synthesis:

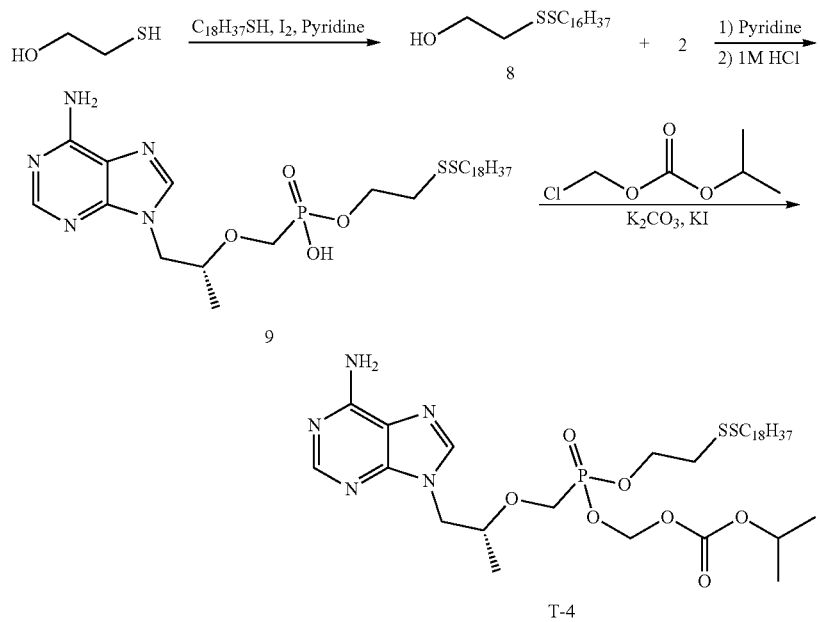

Step 1: Synthesis of 2-(octadecyldisulfanyl)ethanol (Compound 8)

To a reaction flask were added 2-mercaptoethanol (780 mg, 10 mmol), and n-octadecanethiol (2.86 g, 10 mmol), which were dissolved in 35 ml anhydrous methanol and 35 ml anhydrous dichloromethane. Pyridine (1.58 g, 20 mmol) was added to the mixture. Under the nitrogen protection, elemental iodine (2.54 g, 10 mmol) was added to the mixture in portions, and the reaction was stirred at room temperature for 2-5 hours after the addition was completed. Insoluble material was filtered off upon TLC detection showed the reaction was completed, and the filtrate was concentrated to dryness. The residue was dissolved in a small amount of dichloromethane, washed with saturated brine, concentrated, purified by column chromatography, and dried in vacuo to afford product 2.38 g in a yield of 65.7%.

Step 2: Synthesis of (R)-9-{2-[(octadecyldisulfanylethyl)phosphorylmethoxy]propyl}adenine (Compound 9)

To a reaction flask was added Compound 2 (658 mg, 1.74 mmol), which was dissolved in 10 ml anhydrous dichloromethane Under the nitrogen protection, the reaction was cooled to 0° C., and a solution of Compound 8 (761 mg, 2.1 mmol) and pyridine (826 mg, 10.44 mmol) in anhydrous dichloromethane was slowly added to the mixture dropwise. After the addition, the reaction was reacted at the low temperature for 10 minutes and warmed to rt and reacted for 2 hours. Upon MS monitoring showed the reaction was completed, and 1 M dilute hydrochloric acid (10 ml) was added to quench the reaction, which was stirred at room temperature overnight. The organic phase was separated upon MS monitoring showed the reaction was completed. The aqueous phase was extracted 2-3 times with dichloromethane. The organic phase was combined, washed with saturated brine, concentrated, and purified by silica gel column chromatography to afford 1.02 g of product in a yield of 92.9%. LC-MS(APCI): m/z=632.8 (M+1)$^+$.

Step 3: Synthesis of (R)-9-{2-[(octadecyldisulfanylethyl)(isopropylcarbonatemethyl)phosphorylmethoxy]propyl}adenine (Compound T-4)

To a reaction flask were added Compound 9 (640 mg, 1.01 mmol), chloromethyl isopropyl carbonate (770.5 mg, 5.07 mmol), potassium carbonate (700.7 mg, 5.07 mmol) and potassium iodide (84.6 mg, 0.51 mmol) 15 ml DMF was added to the mixture. The reaction was heated to 60° C. and reacted overnight, and cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 239 mg of product in a yield of 31.7%. LC-MS(APCI): m/z=748.6 (M+1)$^+$. $^1$H NMR (400 MHz, CDCl$_3$) δ 8.36 (s, 1H), 8.05 (s, 1H), 6.06 (s, 2H), 5.61 (m, 2H), 4.92 (m, 1H), 4.40-4.12 (m, 4H), 3.92 (m, 2H), 3.68 (t, J=10.0 Hz, 1H), 2.89 (dt, J=19.2, 6.7 Hz, 2H), 2.67 (dd, J=11.8, 7.0 Hz, 2H), 1.66 (s, 2H), 1.33-1.22 (m, 39H), 0.89 (t, J=6.6 Hz, 3H).

Example 7

(R)-9-{2-[(hexadecyldisulfanylethyl)(methylcarbonatemethyl)phosphorylmethoxy]propyl}adenine (Compound T-5)

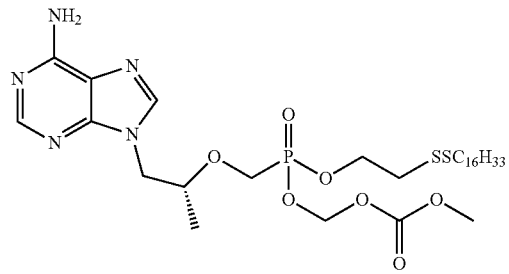

T-5

The following synthetic route was used for the synthesis:

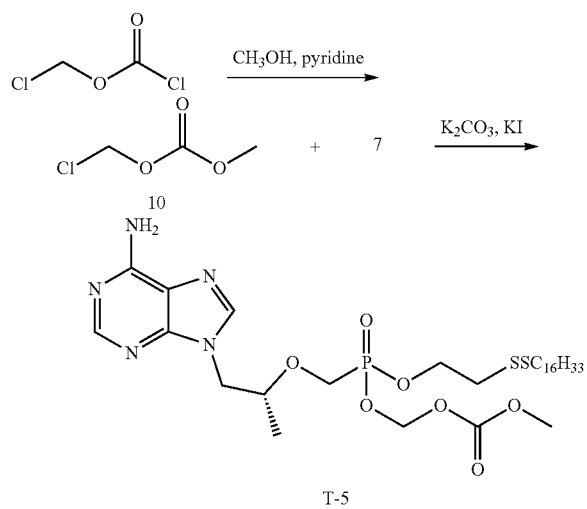

Step 1: Synthesis of Chloromethyl Methyl Carbonate (Compound 10)

To a reaction flask were added chloromethyl chloroformate (1.5 g, 11.72 mmol) and methanol (375 mg, 11.72 mmol), which were dissolved in 10 ml anhydrous ether. The reaction was cooled to 0° C., and pyridine (0.93 g, 11.72 mmol) was added to the reaction dropwise slowly. After the addition, the reaction was warmed to rt and stirred overnight. The mixture was diluted with water, washed three times with 1% citric acid, saturated sodium bicarbonate and saturated brine, dried over anhydrous sodium sulfate, filtered and concentrated to afford the product 1.32 g in a yield of 90.8%.

Step 2: Synthesis of (R)-9-{2-[(hexadecyldisulfanylethyl)(methylcarbonatemethyl)phosphorylmethoxy]propyl}adenine (Compound T-5)

To a reaction flask were added Compound 7 (500 mg, 0.83 mmol), Compound 10 (513.8 mg, 4.14 mmol), potassium carbonate (572.7 mg, 4.14 mmol) and potassium iodide (68.1 mg, 0.41 mmol). 10 ml DMF was added to the mixture. The reaction was heated to 60° C. and reacted overnight, and cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 83 mg of product in a yield of 14.5%. LC-MS(APCI): m/z=692.1 (M+1)$^+$. $^1$H NMR (400 MHz, CDCl$_3$) δ 8.34 (s, 1H), 8.03 (s, 1H), 6.06 (s, 2H), 5.63 (dd, J=28.2, 8.9 Hz, 2H), 4.92 (m, 1H), 4.40-4.12 (m, 3H), 3.92 (m, 2H), 3.84 (s, 3H), 3.68 (t, J=10.0 Hz, 1H), 2.86 (dt, J=19.2, 6.7 Hz, 2H), 2.64 (dd, J=11.8, 7.0 Hz, 2H), 1.64 (s, 2H), 1.33-1.22 (m, 29H), 0.87 (t, J=6.6 Hz, 3H).

Example 8

(R)-9-{2-[(hexadecyldisulfanylethyl)(ethylcarbonatemethyl)phosphorylmethoxy]propyl}adenine (Compound T-6)

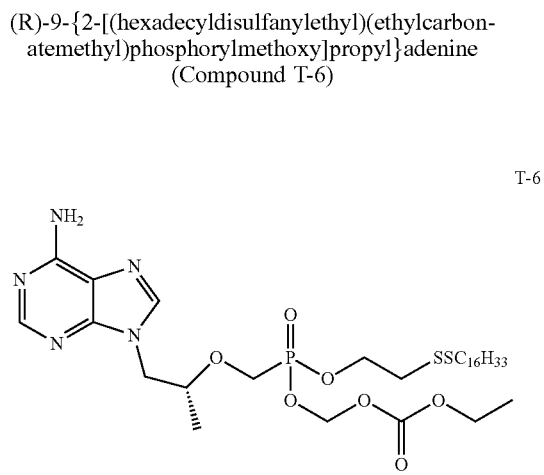

The following synthetic route was used for the synthesis:

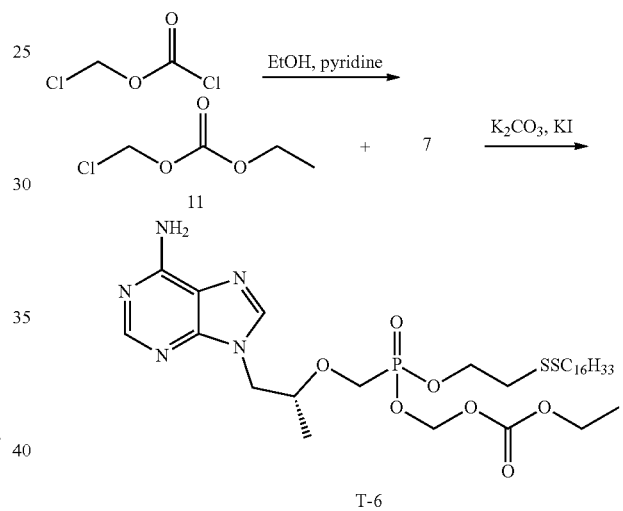

Step 1: Synthesis of Chloromethyl Ethyl Carbonate (Compound 11)

To a reaction flask were added chloromethyl chloroformate (3.0 g, 23.45 mmol) and ethanol (1.08 g, 23.45 mmol), which were dissolved in 20 ml anhydrous ether. The reaction was cooled to 0° C., and pyridine (1.85 g, 23.45 mmol) was slowly added to the reaction dropwise. After the addition, the reaction was warmed to rt and stirred overnight. The mixture was diluted with water, washed three times with 1% citric acid, saturated sodium bicarbonate and saturated brine, dried over anhydrous sodium sulfate, filtered and concentrated to afford the product 2.51 g in a yield of 77.5%.

Step 2: Synthesis of (R)-9-{2-[(hexadecyldisulfanylethyl)(ethylcarbonatemethyl)phosphorylmethoxy]propyl}adenine (Compound T-6)

To a reaction flask were added Compound 7 (500 mg, 0.83 mmol), Compound 11 (571.9 mg, 4.14 mmol), potassium carbonate (572.7 mg, 4.14 mmol) and potassium iodide (68.1 mg, 0.41 mmol). 10 ml DMF was added to the mixture. The reaction was heated to 60° C. and reacted overnight, and cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 99 mg of product in a yield of 16.9%. LC-MS(APCI): m/z=706.4 (M+1)$^+$. $^1$H NMR (400 MHz, CDCl$_3$) δ 8.32 (s, 1H), 8.01 (s, 1H), 6.06 (s, 2H), 5.61 (dd, J=28.2, 8.9 Hz, 2H), 4.91 (m, 1H), 4.40-4.12 (m, 4H), 3.92 (m, 3H), 3.68 (t, J=10.0 Hz, 1H), 2.88 (dt, J=19.2, 6.7 Hz, 2H), 2.67 (dd, J=11.8, 7.0 Hz, 2H), 1.68 (t, J=9.5 Hz, 3H), 1.64 (s, 2H), 1.33-1.22 (m, 29H), 0.86 (t, J=6.6 Hz, 3H).

Example 9

(R)-9-{2-[(hexadecyldisulfanylethyl)(propylcarbonatemethyl)phosphorylmethoxy]propyl}adenine (Compound T-7)

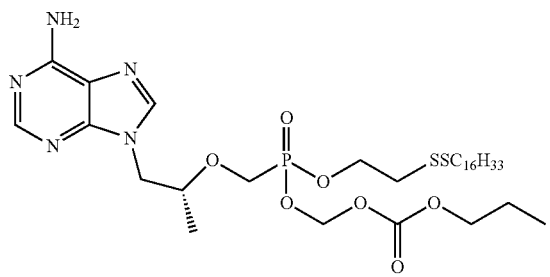

T-7

The following synthetic route was used for the synthesis:

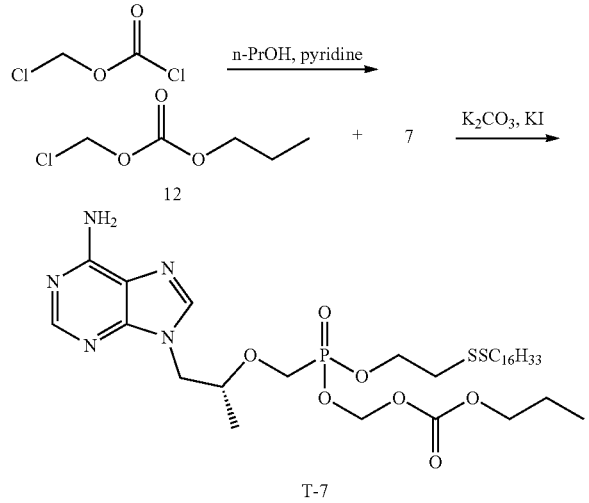

Step 1: Synthesis of Chloromethyl Propyl Carbonate (Compound 12)

To a reaction flask were added chloromethyl chloroformate (3.0 g, 23.45 mmol) and n-propanol (1.41 g, 23.45 mmol), which were dissolved in 20 ml anhydrous ether. The reaction was cooled to 0° C., and pyridine (1.85 g, 23.45 mmol) was slowly added to the mixture dropwise. After the addition, the reaction was warmed to rt and stirred overnight. The mixture was diluted with water, washed three times with 1% citric acid, saturated sodium bicarbonate and saturated brine, dried over anhydrous sodium sulfate, filtered and concentrated to afford the product 2.86 g in a yield of 80.2%.

Step 2: Synthesis of (R)-9-{2-[(hexadecyldisulfanylethyl)(propylcarbonatemethyl)phosphorylmethoxy]propyl}adenine (Compound T-7)

To a reaction flask were added Compound 7 (500 mg, 0.83 mmol), Compound 12 (630 mg, 4.14 mmol), potassium carbonate (572.7 mg, 4.14 mmol) and potassium iodide (68.1 mg, 0.41 mmol), and 10 ml DMF. The reaction was heated to 60° C. and reacted overnight, then cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 127 mg of product in a yield of 21.3%. LC-MS(APCI): m/z=720.5 (M+1)$^+$. $^1$H NMR (400 MHz, CDCl$_3$) δ 8.33 (s, 1H), 8.02 (s, 1H), 6.06 (s, 2H), 5.61 (dd, J=28.2, 8.9 Hz, 2H), 4.91 (m, 1H), 4.40-4.12 (m, 4H), 3.94 (m, 3H), 3.68 (t, J=10.0 Hz, 1H), 2.89 (dt, J=19.2, 6.7 Hz, 2H), 2.67 (dd, J=11.8, 7.0 Hz, 2H), 1.69 (m, 2H), 1.64 (s, 2H), 1.33-1.22 (m, 32H), 0.86 (t, J=6.6 Hz, 3H).

Example 10

(R)-9-{2-[(hexadecyldisulfanylethyl)(n-butylcarbonatemethyl)phosphorylmethoxy]propyl}adenine (Compound T-8)

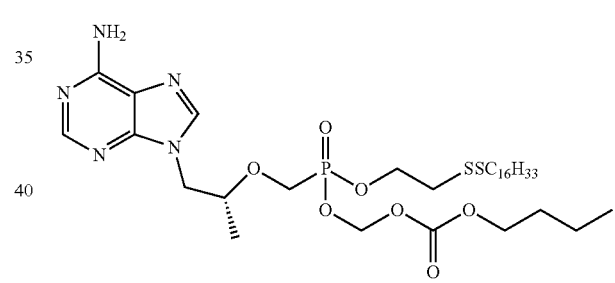

T-8

The following synthetic route was used for the synthesis:

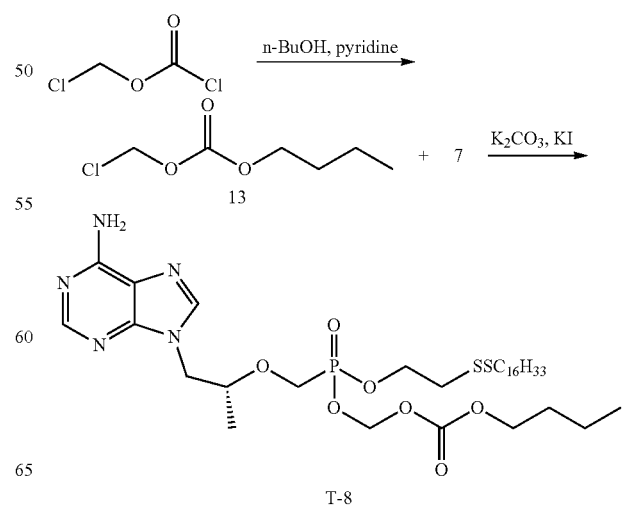

Step 1: Synthesis of Chloromethyl Butyl Carbonate (Compound 13)

To a reaction flask were added chloromethyl chloroformate (3.0 g, 23.45 mmol) and n-butanol (1.74 g, 23.45 mmol), which were dissolved in 20 ml anhydrous ether. The reaction was cooled to 0° C., and pyridine (1.85 g, 23.45 mmol) was slowly added to the mixture dropwise. After the addition, the reaction was warmed to rt and stirred overnight. The mixture was diluted with water, washed three times with 1% citric acid, saturated sodium bicarbonate and saturated brine, dried over anhydrous sodium sulfate, filtered and concentrated to afford the product 2.94 g in a yield of 75.6%.

Step 2: Synthesis of (R)-9-{2-[(hexadecyldisulfanylethyl)(butylcarbonatemethyl)phosphorylmethoxy]propyl}adenine (Compound T-8)

To a reaction flask were added Compound 7 (500 mg, 0.83 mmol), Compound 13 (688 mg, 4.14 mmol), potassium carbonate (572.7 mg, 4.14 mmol) and potassium iodide (68.1 mg, 0.41 mmol). 10 ml DMF was added to the mixture. The reaction was heated to 60° C. and reacted overnight, and cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 119 mg of product in a yield of 19.6%. LC-MS(APCI): m/z=734.2 (M+1)$^+$. $^1$H NMR (400 MHz, CDCl$_3$) δ 8.33 (s, 1H), 8.02 (s, 1H), 6.06 (s, 2H), 5.61 (dd, J=28.2, 8.9 Hz, 2H), 4.91 (m, 1), 4.40-4.12 (m, 4H), 3.94 (m, 3H), 3.68 (t, J=10.0 Hz, 1H), 2.89 (dt, J=19.2, 6.7 Hz, 2H), 2.67 (dd, J=11.8, 7.0 Hz, 2H), 1.69 (m 2H), 1.64 (s, 2H), 1.33-1.22 (m, 34H), 0.86 (t, J=6.6 Hz, 3H).

Example 11

(R)-9-{2-[(hexadecyldisulfanylethyl)(isobutylcarbonatemethyl)phosphorylmethoxy]propyl}adenine (Compound T-9)

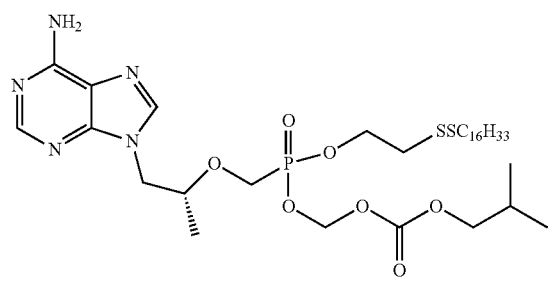

The following synthetic route was used for the synthesis:

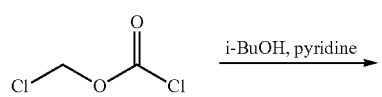

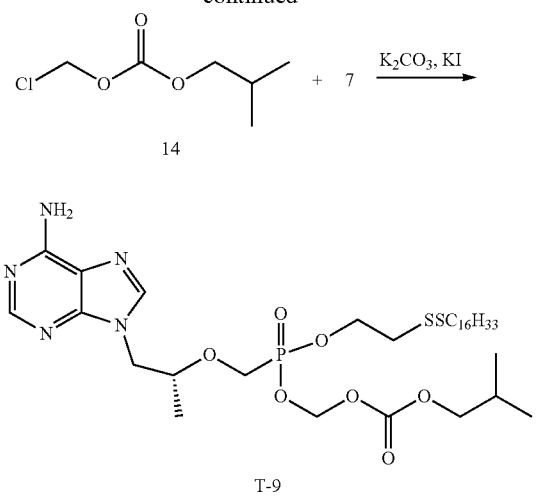

Step 1: Synthesis of Isobutyl Chloromethyl Carbonate (Compound 14)

To a reaction flask were added chloromethyl chloroformate (3.0 g, 23.45 mmol) and isobutanol (1.74 g, 23.45 mmol), which were dissolved in 20 ml anhydrous ether. The reaction was cooled to 0° C., and pyridine (1.85 g, 23.45 mmol) was slowly added the mixture dropwise. After the addition, the reaction was warmed to rt and stirred overnight. The mixture was diluted with water, washed three times with 1% citric acid, saturated sodium bicarbonate and saturated brine, dried over anhydrous sodium sulfate, filtered and concentrated to afford the product 3.06 g in a yield of 78.7%.

Step 2: Synthesis of (R)-9-{2-[(hexadecyldisulfanylethyl)(isobutylcarbonatemethyl)phosphorylmethoxy]propyl}adenine (Compound T-9)

To a reaction flask were added Compound 7 (500 mg, 0.83 mmol), Compound 14 (688 mg, 4.14 mmol), potassium carbonate (572.7 mg, 4.14 mmol) and potassium iodide (68.1 mg, 0.41 mmol). 10 ml DMF was added to the mixture. The reaction was heated to 60° C. and reacted overnight, and cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 134 mg of product in a yield of 22.0%. LC-MS(APCI): m/z=734.2 (M+1)$^+$. $^1$H NMR (400 MHz, CDCl$_3$) δ 8.34 (s, 1H), 8.03 (s, 1H), 6.06 (s, 2H), 5.61 (dd, J=28.2, 8.9 Hz, 2H), 4.91 (m, 1H), 4.40-4.12 (m, 4H), 3.94 (m, 3H), 3.68 (t, J=10.0 Hz, 1H), 2.89 (dt, J=19.2, 6.7 Hz, 2H), 2.67 (dd, J=11.8, 7.0 Hz, 2H), 1.69 (m 1H), 1.64 (s, 2H), 1.33-1.22 (m, 35H), 0.86 (t, J=6.6 Hz, 3H).

Example 12

(R)-9-{2-[(hexadecyldisulfanylethyl)(s-butylcarbonatemethyl)phosphorylmethoxy]propyl}adenine (Compound T-10)

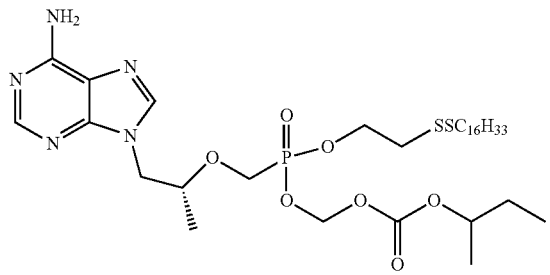

The following synthetic route was used for the synthesis:

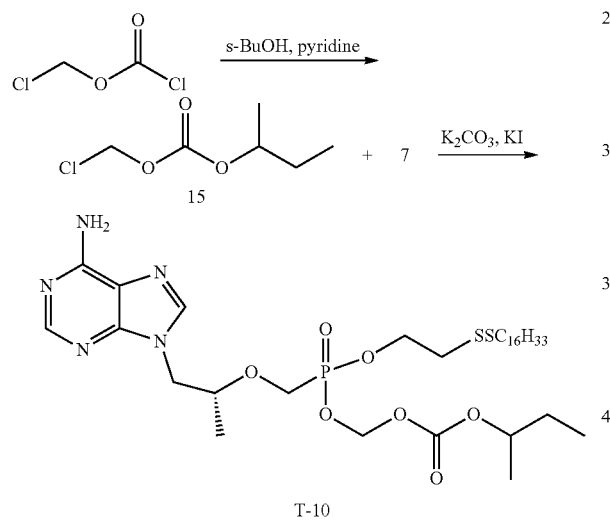

Step 1: Synthesis of Sec-Butyl Chloromethyl Carbonate (Compound 15)

To a reaction flask were added chloromethyl chloroformate (3.0 g, 23.45 mmol) and sec-butanol (1.74 g, 23.45 mmol), which was dissolved in 20 ml anhydrous ether. The reaction was cooled to 0° C., and pyridine (1.85 g, 23.45 mmol) was slowly added the mixture dropwise. After the addition, the reaction was warmed to rt and stirred overnight. The mixture was diluted with water, washed three times with 1% citric acid, saturated sodium bicarbonate and saturated brine, dried over anhydrous sodium sulfate, filtered and concentrated to afford the product 2.99 g in a yield of 76.8%.

Step 2: Synthesis of (R)-9-{2-[(hexadecyldisulfanylethyl)(s-butylcarbonatemethyl)phosphorylmethoxy]propyl}adenine (Compound T-10)

To a reaction flask were added Compound 7 (500 mg, 0.83 mmol), Compound 15 (688 mg, 4.14 mmol), potassium carbonate (572.7 mg, 4.14 mmol) and potassium iodide (68.1 mg, 0.41 mmol). 10 ml DMF was added to the mixture. The reaction was heated to 60° C. and reacted overnight, and cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 112 mg of product in a yield of 18.4%. LC-MS(APCI): m/z=734.2 (M+1)$^+$. $^1$H NMR (400 MHz, CDCl$_3$) δ 8.31 (s, 1H), 8.01 (s, 1H), 6.06 (s, 2H), 5.62 (m, 2H), 4.93 (m, 1H), 4.40-4.12 (m, 4H), 3.94 (m, 2H), 3.68 (t, J=10.0 Hz, 1H), 2.92 (dt, J=19.2, 6.7 Hz, 2H), 2.67 (dd, J=11.8, 7.0 Hz, 2H), 1.69 (m 1H), 1.64 (s, 2H), 1.33-1.22 (m, 36H), 0.88 (t, J=6.6 Hz, 3H).

Example 13

(R)-9-{2-[(hexadecyldisulfanylethyl)(t-butylcarbonatemethyl)phosphorylmethoxy]propyl}adenine (Compound T-11)

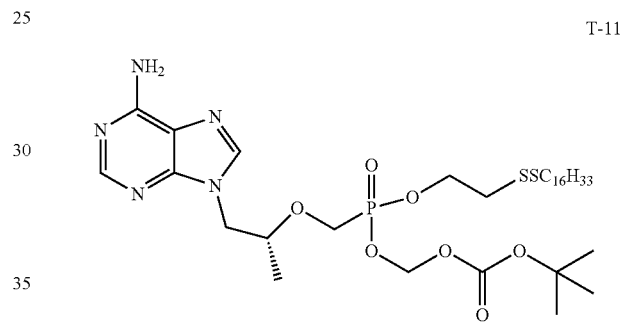

The following synthetic route was used for the synthesis:

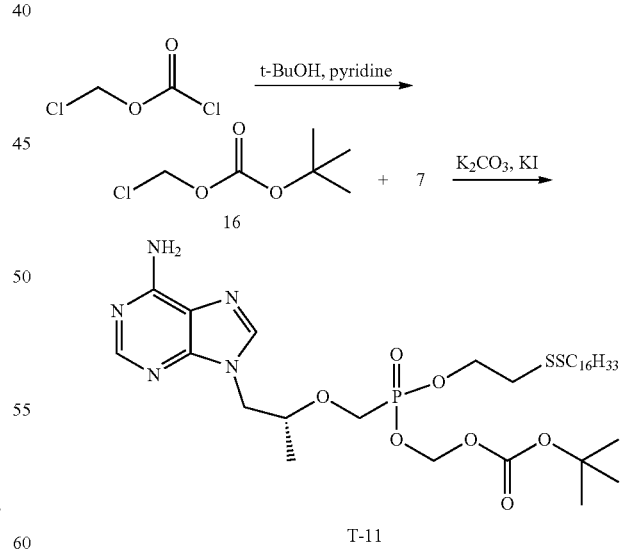

Step 1: Synthesis of Tert-Butyl Chloromethyl Carbonate (Compound 16)

To a reaction flask were added chloromethyl chloroformate (3.0 g, 23.45 mmol) and tert-butanol (1.74 g, 23.45 mmol), which were dissolved in 20 ml anhydrous ether. The reaction was cooled to 0° C., and pyridine (1.85 g, 23.45 mmol) was slowly added to the mixture dropwise. After the addition, the reaction was warmed to rt and stirred overnight. The mixture was diluted with water, washed three times with 1% citric acid, saturated sodium bicarbonate and saturated brine, dried over anhydrous sodium sulfate, filtered and concentrated to afford the product 3.25 g in a yield of 83.5%.

Step 2: Synthesis of (R)-9-{2-[(hexadecyldisulfanylethyl)(t-butylcarbonatemethyl)phosphorylmethoxy]propyl}adenine (Compound T-11)

To a reaction flask were added Compound 7 (500 mg, 0.83 mmol), Compound 16 (688 mg, 4.14 mmol), potassium carbonate (572.7 mg, 4.14 mmol) and potassium iodide (68.1 mg, 0.41 mmol). 10 ml DMF was added to the mixture. The reaction was heated to 60° C. and reacted overnight, and cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 134 mg of product in a yield of 22.0%. LC-MS(APCI): m/z=734.2 (M+1)$^+$. $^1$H NMR (400 MHz, CDCl$_3$) δ 8.34 (s, 1H), 8.03 (s, 1H), 6.06 (s, 2H), 5.61 (m, 2H), 4.92 (dd, J=13.2, 6.6 Hz, 1H), 4.40-4.12 (m, 3H), 3.92 (dd, J=11.5, 7.1 Hz, 2H), 3.68 (t, J=10.0 Hz, 1H), 2.87 (dt, J=19.2, 6.7 Hz, 2H), 2.67 (dd, J=11.8, 7.0 Hz, 2H), 1.64 (s, 2H), 1.33-1.22 (m, 38H), 0.87 (t, J=6.6 Hz, 3H).

Example 14

(R)-9-{2-[(hexadecyldisulfanylethyl)(neopentylcarbonatemethyl)phosphorylmethoxy]propyl}adenine (Compound T-12)

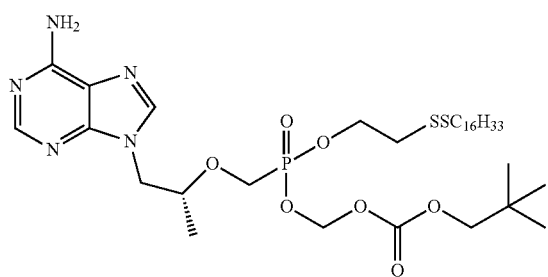

The following synthetic route was used for the synthesis:

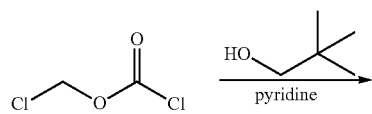

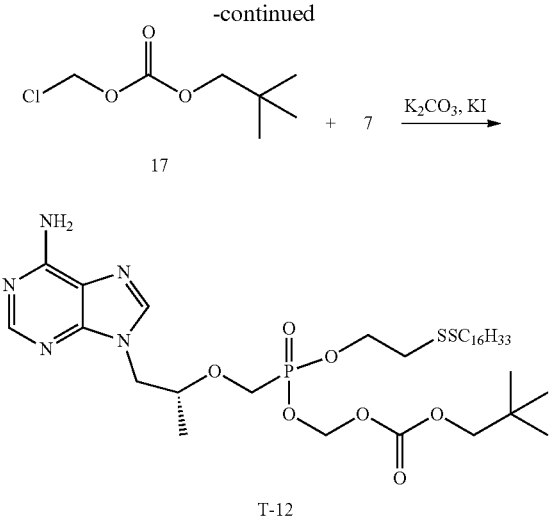

Step 1: Synthesis of Neopentyl Chloromethyl Carbonate (Compound 17)

To a reaction flask were added chloromethyl chloroformate (3.0 g, 23.45 mmol) and neopentyl alcohol (2.07 g, 23.45 mmol), which were dissolved in 20 ml anhydrous ether. The reaction was cooled to 0° C., and pyridine (1.85 g, 23.45 mmol) was slowly added to the mixture dropwise. After the addition, the reaction was warmed to rt and stirred overnight. The mixture was diluted with water, washed three times with 1% citric acid, saturated sodium bicarbonate and saturated brine, dried over anhydrous sodium sulfate, filtered and concentrated to afford the product 3.58 g in a yield of 84.8%.

Step 2: Synthesis of (R)-9-{2-[(hexadecyldisulfanylethyl)(neopentylcarbonatemethyl)phosphorylmethoxy]propyl}adenine (Compound T-12)

To a reaction flask were added Compound 7 (500 mg, 0.83 mmol), Compound 17 (746 mg, 4.14 mmol), potassium carbonate (572.7 mg, 4.14 mmol) and potassium iodide (68.1 mg, 0.41 mmol). 10 ml DMF was added to the mixture. The reaction was heated to 60° C. and reacted overnight, and cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 98 mg of product in a yield of 15.8%. LC-MS(APCI): m/z=748.6 (M+1)$^+$. $^1$H NMR (400 MHz, CDCl$_3$) δ 8.34 (s, 1H), 8.03 (s, 1H), 6.06 (s, 2H), 5.61 (m, 2H), 4.92 (dd, J=13.2, 6.6 Hz, 1H), 4.40-4.12 (m, 4H), 3.92 (dd, J=11.5, 7.1 Hz, 3H), 3.68 (t, J=10.0 Hz, 1H), 2.87 (dt, J=19.2, 6.7 Hz, 2H), 2.67 (dd, J=11.8, 7.0 Hz, 2H), 1.64 (s, 2H), 1.33-1.22 (m, 38H), 0.87 (t, J=6.6 Hz, 3H).

Example 15

(R)-9-{2-[(hexadecyldisulfanylethyl)(cyclopentyl-carbonatemethyl)phosphorylmethoxy]propyl}adenine (Compound T-13)

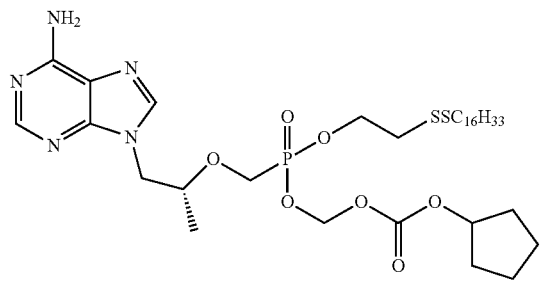

The following synthetic route was used for the synthesis:

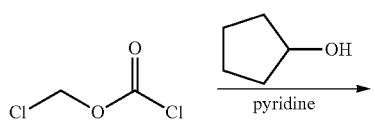

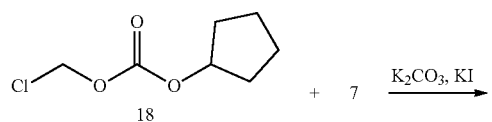

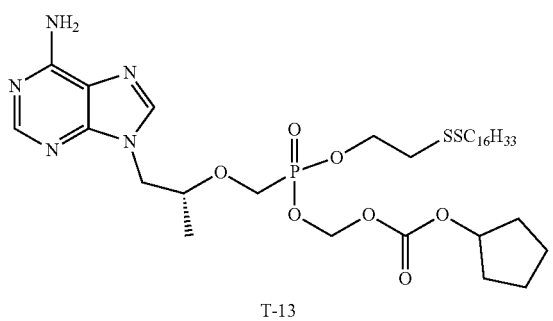

Step 1: Synthesis of Cyclopentyl Chloromethyl Carbonate (Compound 18)

To a reaction flask were added chloromethyl chloroformate (3.0 g, 23.45 mmol) and cyclopentanol (2.02 g, 23.45 mmol), which were dissolved with 20 ml anhydrous ether. The reaction was cooled to 0° C., and pyridine (1.85 g, 23.45 mmol) was slowly added dropwise. After the addition, the reaction was warmed to rt and stirred overnight. The reaction was diluted with water, washed three times with 1% citric acid, saturated sodium bicarbonate and saturated brine, which was dried over anhydrous sodium sulfate, filtered and concentrated to afford the product 3.27 g in a yield of 78.4%.

Step 2: Synthesis of (R)-9-{2-[(hexadecyldisulfanylethyl)(cyclopentylcarbonatemethyl)phosphorylmethoxy]propyl}adenine (Compound T-13)

To a reaction flask were added Compound 7 (500 mg, 0.83 mmol), Compound 18 (737.8 mg, 4.14 mmol), potassium carbonate (572.7 mg, 4.14 mmol) and potassium iodide (68.1 mg, 0.41 mmol). 10 ml DMF was added to the mixture. The reaction was heated to 60° C. and reacted overnight, and cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 114 mg of product in a yield of 18.4%. LC-MS(APCI): m/z=746.8 (M+1)$^+$. $^1$H NMR (400 MHz, CDCl$_3$) δ 8.34 (s, 1H), 8.03 (s, 1H), 6.06 (s, 2H), 5.61 (m, 2H), 4.92 (dd, J=13.2, 6.6 Hz, 1H), 4.40-4.12 (m, 4H), 3.92 (dd, J=11.5, 7.1 Hz, 2H), 3.68 (t, J=10.0 Hz, 1H), 2.87 (dt, J=19.2, 6.7 Hz, 2H), 2.67 (dd, J=11.8, 7.0 Hz, 2H), 1.64-1.57 (m, 6H), 1.33-1.22 (m, 33H), 0.87 (t, J=6.6 Hz, 3H).

Example 16

(R)-9-{2-[(hexadecyldisulfanylethyl)(cyclohexylcarbonatemethyl)phosphorylmethoxy]propyl}adenine (Compound T-14)

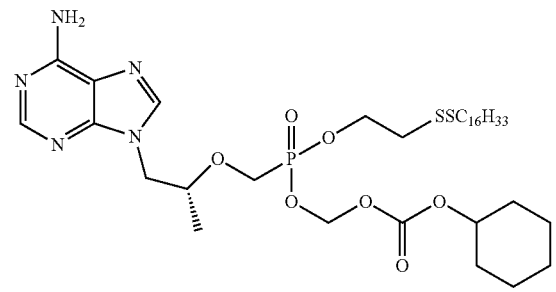

The following synthetic route was used for the synthesis:

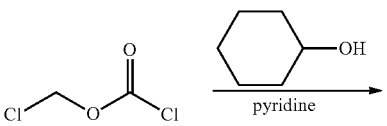

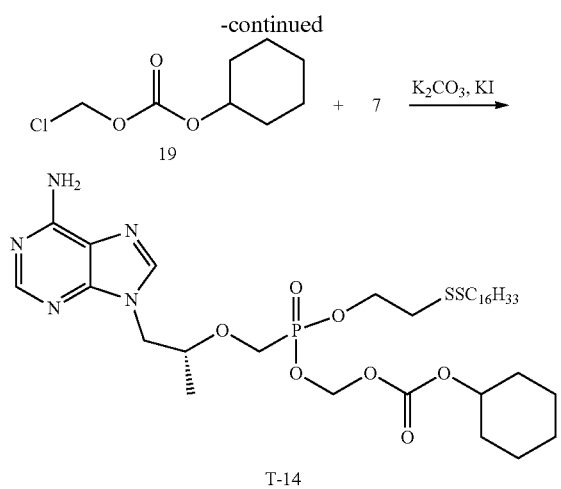

T-14

Step 1: Synthesis of Cyclohexyl Chloromethyl Carbonate (Compound 19)

To a reaction flask were added chloromethyl chloroformate (3.0 g, 23.45 mmol) and cyclohexanol (2.35 g, 23.45 mmol), which was dissolved in 20 ml anhydrous ether. The reaction was cooled to 0° C., and pyridine (1.85 g, 23.45 mmol) was slowly added to the mixture dropwise. After the addition, the reaction was warmed to rt and stirred overnight. The mixture was diluted with water, washed three times with 1% citric acid, saturated sodium bicarbonate and saturated brine, dried over anhydrous sodium sulfate, filtered and concentrated to afford the product 3.47 g in a yield of 77.1%.

Step 2: Synthesis of (R)-9-{2-[(hexadecyldisulfanylethyl)(cyclohexylcarbonatemethyl)phosphorylmethoxy]propyl}adenine (Compound T-14)

To a reaction flask were added Compound 7 (500 mg, 0.83 mmol), Compound 19 (796 mg, 4.14 mmol), potassium carbonate (572.7 mg, 4.14 mmol) and potassium iodide (68.1 mg, 0.41 mmol). 10 ml DMF was added to the mixture. The reaction was heated to 60° C. and reacted overnight. The reaction was cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 147 mg of product in a yield of 23.3%. LC-MS(APCI): m/z=760.9 (M+1)$^+$. $^1$H NMR (400 MHz, CDCl$_3$) δ 8.34 (s, 1H), 8.03 (s, 1H), 6.06 (s, 2H), 5.61 (m, 2H), 4.92 (dd, J=13.2, 6.6 Hz, 1H), 4.40-4.12 (m, 4H), 3.92 (dd, J=11.5, 7.1 Hz, 2H), 3.68 (t, J=10.0 Hz, 1H), 2.87 (m, 2H), 2.67 (dd, J=11.8, 7.0 Hz, 2H), 1.66-1.58 (m, 6H), 1.33-1.22 (m, 35H), 0.87 (t, J=6.6 Hz, 3H).

Example 17

(2'R,1'S)-9-{2-[(dodecyldisulfanylethyl)(isopropoxycarbonyl-1-ylethylamino)phosphorylmethoxy]propyl}adenine (Compound T-15)

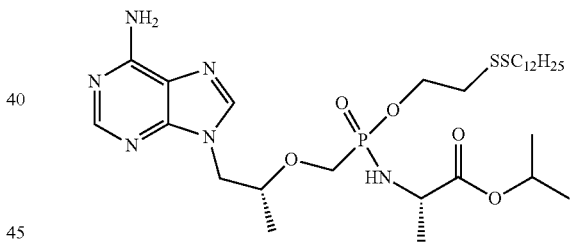

The following synthetic route was used for the synthesis:

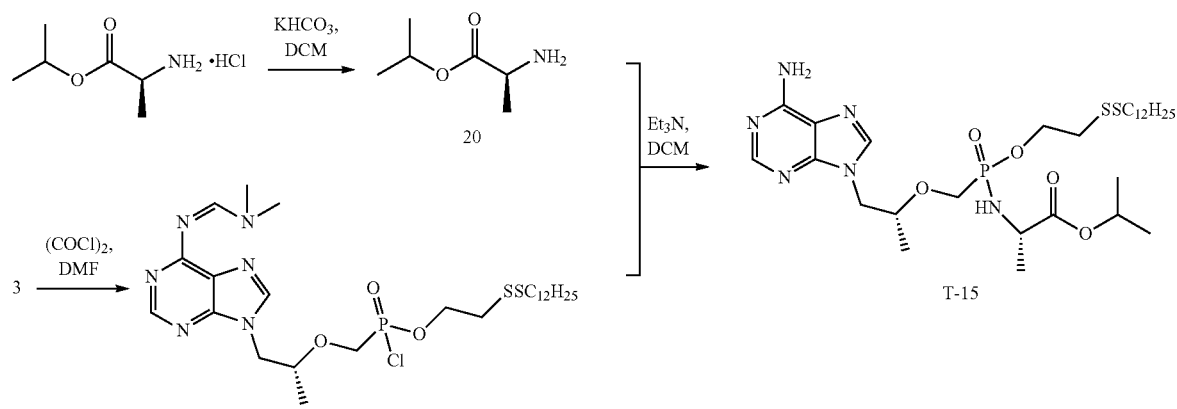

Step 1: Synthesis of L-Isopropyl Alanine (Compound 20)

To a reaction flask was added L-isopropyl alanine hydrochloride (10.0 g, 59.9 mmol), which was dissolved in 40 ml anhydrous dichloromethane. Sodium bicarbonate (15.0 g, 149.7 mmol) was added to the mixture, and gas was released. The reaction was stirred at room temperature overnight. Insoluble material was filtered off. The organic phase was washed 3 times with saturated brine, dried over anhydrous sodium sulfate, and concentrated to afford the product 7.54 g in a yield of 96.0%.

Step 2: Synthesis of (2'R,1'S)-9-{2-[(dodecyldisulfanylethyl)(isopropoxycarbonyl-1-ylethylamino)phosphorylmethoxy]propyl}adenine (Compound T-15)

To a reaction flask were added Compound 3 (1.5 g, 2.74 mmol) and anhydrous DMF (240 mg, 3.29 mmol), which were dissolved in 30 ml anhydrous dichloromethane. Oxalyl chloride (6.85 ml, 13.7 mmol) was slowly added to the mixture dropwise at room temperature. After the addition, the reaction was stirred for 2-3 hours under the nitrogen protection. The reaction was concentrated to remove the solvent and excess oxalyl chloride. The residue was dissolved in 20 ml anhydrous dichloromethane, which was cooled to 0° C. Under the nitrogen protection, a solution of Compound 20 (1.8 g, 13.7 mmol) and triethylamine (1.39 g, 13.7 mmol) in dichloromethane was slowly added to the mixture dropwise. After the addition, the reaction was warmed to rt and reacted for 1 hour. Upon TLC detection showed the reaction was completed, 2 ml ethanolamine was added to the mixture and the mixture was stirred overnight. The mixture was diluted with a small amount of water. The organic phase was separated, washed 3 times with saturated brine, concentrated, and purified by silica gel column chromatography to afford 315 mg of product in a yield of 17.4%. LC-MS(APCI): m/z=661.1 (M+1)$^+$. $^1$H NMR (400 MHz, CDCl$_3$) δ 8.34 (d, J=4.3 Hz, 1H), 8.01 (d, J=14.2 Hz, 1H), 5.87 (s, 2H), 4.97 (ddt, J=43.9, 12.5, 6.2 Hz, 1H), 4.44-4.30 (m, 1H), 4.27-4.08 (m, 3H), 3.96 (ddd, J=19.1, 10.8, 3.5 Hz, 2H), 3.87-3.76 (m, 1H), 3.56 (ddd, J=13.1, 10.1, 6.9 Hz, 1H), 2.87 (ddd, J=19.6, 10.9, 6.5 Hz, 2H), 2.68 (td, J=7.3, 5.3 Hz, 2H), 1.69-1.60 (m, 2H), 1.41-1.31 (m, 6H), 1.30-1.20 (m, 24H), 0.87 (t, J=6.8 Hz, 3H).

Example 18

(2'R,1'S)-9-{2-[(tetradecyldisulfanylethyl)(isopropoxycarbonyl-1-ylethylamino)phosphorylmethoxy]propyl}adenine (Compound T-16)

The following synthetic route was used for the synthesis:

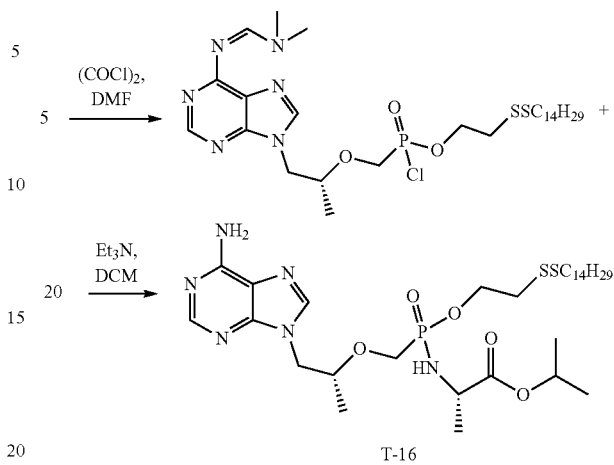

To a reaction flask were added Compound 5 (979 mg, 1.7 mmol) and anhydrous DMF (150 mg, 2.04 mmol), which was dissolved in 20 ml anhydrous dichloromethane. Oxalyl chloride (4.25 ml, 8.51 mmol) was slowly added to the mixture dropwise at room temperature. After the addition, the reaction was stirred for 2-3 hours under the nitrogen protection. The mixture was concentrated to remove the solvent and excess oxalyl chloride. The residue was dissolved in 20 ml anhydrous dichloromethane, and the reaction was cooled to 0° C. Under the nitrogen protection, a solution of Compound 20 (1.11 g, 8.5 mmol) and triethylamine (861.1 mg, 8.5 mmol) in dichloromethane was slowly added to the mixture dropwise. After the addition, the reaction was warmed to rt and reacted for 1 hour. Upon TLC detection showed the reaction was completed, 2 ml ethanolamine was added to the mixture and the mixture was stirred overnight. The mixture was diluted with a small amount of water. The organic phase was separated, washed 3 times with saturated brine, concentrated, and purified by silica gel column chromatography to afford 146 mg of product in a yield of 12.5%. LC-MS(APCI): m/z=689.5 (M+1)$^+$. $^1$H NMR (400 MHz, CDCl$_3$) δ 8.34 (d, J=4.3 Hz, 1H), 8.00 (d, J=13.1 Hz, 1H), 5.79 (s, 2H), 4.98 (dtd, J=44.5, 12.5, 6.2 Hz, 1H), 4.38 (ddd, J=19.6, 14.4, 3.0 Hz, 1H), 4.26-4.06 (m, 3H), 3.96 (tdd, J=18.1, 10.3, 3.3 Hz, 2H), 3.87-3.75 (m, 1H), 3.61-3.51 (m, 1H), 2.92-2.80 (m, 2H), 2.67 (dt, J=12.4, 7.2 Hz, 2H), 1.65 (dd, J=13.1, 7.0 Hz, 2H), 1.38-1.20 (m, 34H), 0.87 (t, J=6.8 Hz, 3H).

Example 19

(2'R,1'S)-9-{2-[(hexadecyldisulfanylethyl)(isopropoxycarbonyl-1-ylethylamino)phosphorylmethoxy]propyl}adenine (Compound T-17)

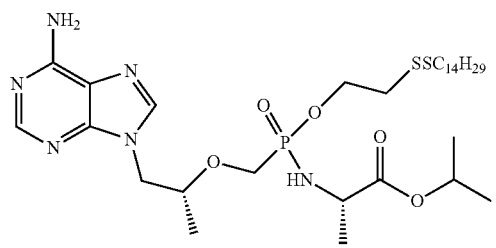

T-16

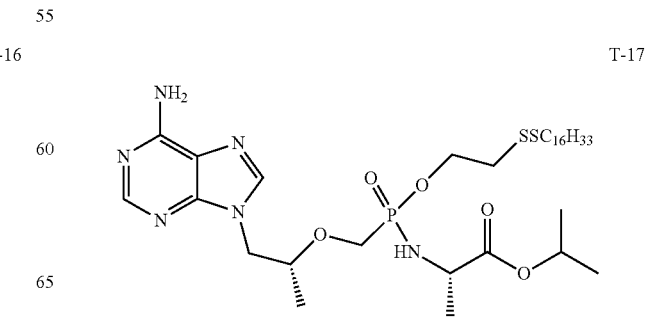

T-17

The following synthetic route was used for the synthesis:

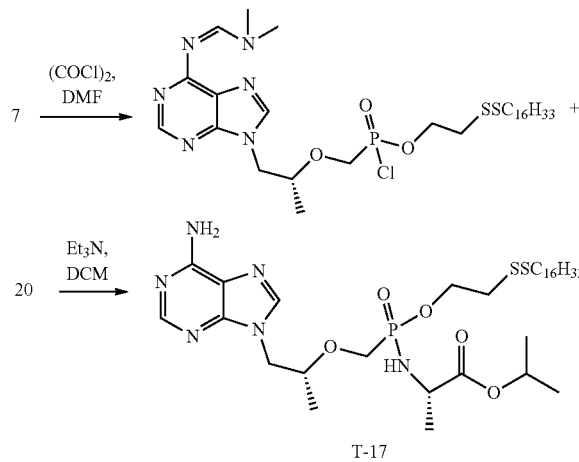

To a reaction flask were added Compound 7 (800 mg, 1.33 mmol) and anhydrous DMF (194.5 mg, 2.66 mmol), which were dissolved in 15 ml anhydrous dichloromethane. Oxalyl chloride (3.32 ml, 6.63 mmol) was added dropwise to the mixture slowly at room temperature. After the addition, the reaction was stirred for 2-3 hours under the nitrogen protection. The reaction was concentrated to remove the solvent and excess oxalyl chloride, which were dissolved in 15 ml anhydrous dichloromethane. The reaction was cooled to 0° C., and a solution of Compound 20 (698 mg, 5.32 mmol) and triethylamine (671 mg, 6.63 mmol) in dichloromethane was slowly added to the mixture dropwise under the nitrogen protection. After the addition, the reaction was warmed to rt and reacted for 1 hour. Upon TLC detection showed the reaction was completed, 2 ml ethanolamine was added to the mixture and the mixture was stirred overnight. The mixture was diluted with a small amount of water. The organic phase was separated, washed 3 times with saturated brine, concentrated, and purified by silica gel column chromatography to afford 127 mg of product in a yield of 13.3%. LC-MS (APCI): m/z=717.4 (M+1)$^+$. $^1$H NMR (400 MHz, CDCl$_3$) δ 8.34 (d, J=4.4 Hz, 1H), 7.99 (d, J=12.2 Hz, 1H), 5.76 (d, J=7.0 Hz, 2H), 4.97 (ddt, J=44.7, 12.5, 6.3 Hz, 1H), 4.38 (ddd, J=19.6, 14.4, 3.0 Hz, 1H), 4.26-4.07 (m, 3H), 4.02-3.90 (m, 2H), 3.86-3.76 (m, 1H), 3.56 (ddd, J=13.2, 10.1, 7.6 Hz, 1H), 2.87 (ddd, J=20.3, 10.2, 5.7 Hz, 2H), 2.72-2.62 (m, 2H), 1.69-1.59 (m, 2H), 1.35 (dd, J=9.3, 7.2 Hz, 6H), 1.29-1.20 (m, 32H), 0.87 (t, J=6.8 Hz, 3H).

Example 20

(2'R,1'S)-9-{2-[(octadecyldisulfanylethyl)(isopropoxycarbonyl-1-ylethylamino)phosphorylmethoxy]propyl}adenine (Compound T-18)

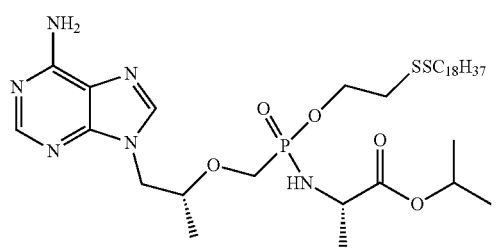

The following synthetic route was used for the synthesis:

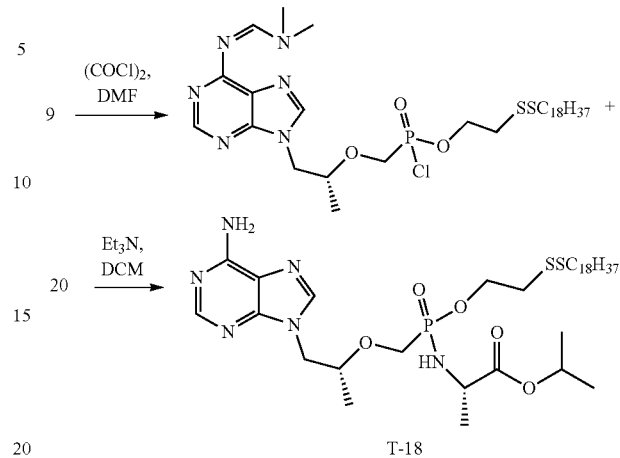

To a reaction flask were added Compound 9 (800 mg, 1.27 mmol) and anhydrous DMF (111 mg, 1.52 mmol), which were dissolved in 15 ml anhydrous dichloromethane. Oxalyl chloride (3.17 ml, 6.33 mmol) was slowly added to the mixture dropwise at room temperature. After the addition, the reaction was stirred for 2-3 hours under the nitrogen protection. The reaction was concentrated to remove the solvent and excess oxalyl chloride. The residue was dissolved in 15 ml anhydrous dichloromethane, and the reaction was cooled to 0° C. Under the nitrogen protection, a solution of Compound 20 (665 mg, 5.07 mmol) and triethylamine (640 mg, 6.33 mmol) in dichloromethane was slowly added to the mixture dropwise. After the addition, the reaction was warmed to rt and reacted for 1 hour. Upon TLC detection showed the reaction was completed, 2 ml ethanolamine was added to the mixture and the mixture was stirred overnight. The mixture was diluted with a small amount of water. The organic phase was separated, washed 3 times with saturated brine, concentrated, and purified by silica gel column chromatography to afford 136 mg of product in a yield of 13.3%. LC-MS(APCI): m/z=745.7 (M+1)$^+$. $^1$H NMR (400 MHz, CDCl$_3$) δ 8.34 (d, J=4.3 Hz, 1H), 7.99 (d, J=12.8 Hz, 1H), 5.79 (d, J=6.0 Hz, 2H), 4.97 (ddt, J=44.0, 12.5, 6.3 Hz, 1H), 4.44-4.31 (m, 1H), 4.17 (dddd, J=23.9, 22.1, 10.8, 6.5 Hz, 3H), 3.96 (tdd, J=18.5, 10.5, 3.6 Hz, 2H), 3.86-3.74 (m, 1H), 3.56 (ddd, J=13.1, 10.1, 6.9 Hz, 1H), 2.93-2.80 (m, 2H), 2.68 (td, J=7.3, 5.4 Hz, 2H), 1.65 (dq, J=14.4, 7.0 Hz, 2H), 1.35 (dd, J=8.8, 7.3 Hz, 6H), 1.30-1.20 (m, 36H), 0.87 (t, J=6.8 Hz, 3H).

Example 21

(R)-9-{2-[(hexadecyldisulfanylpropyl)(isopropylcarbonatemethyl)phosphorylmethoxy]propyl}adenine (Compound T-19)

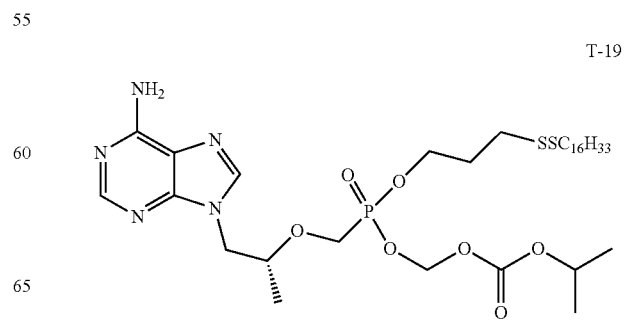

The following synthetic route was used for the synthesis:

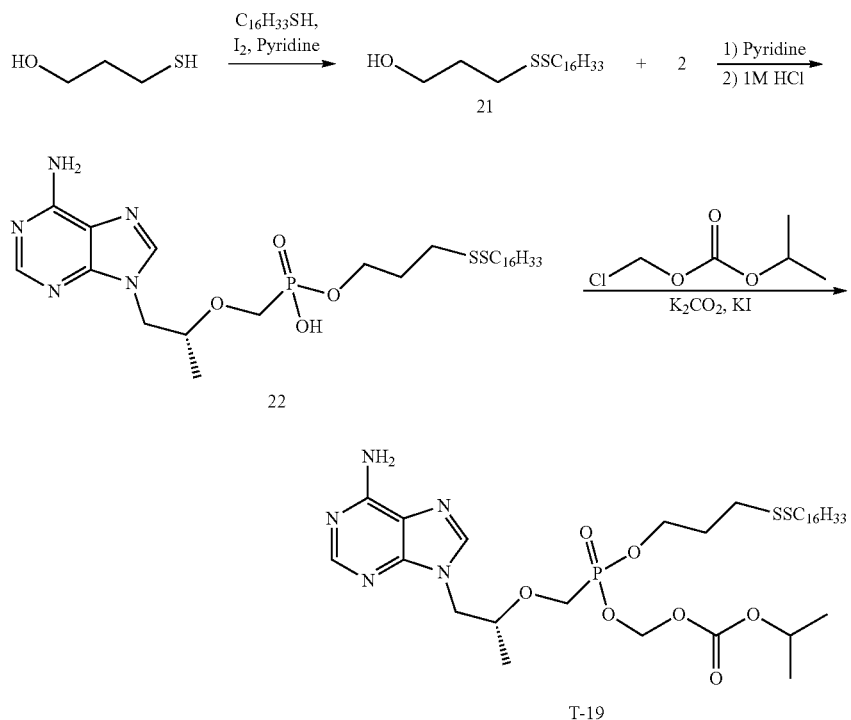

Step 1: Synthesis of 3-(hexadecyldisulfanyl)propanol (Compound 21)

To a reaction flask were added 3-mercaptopropanol (2.76 g, 30 mmol), and n-hexadecanethiol (7.75 g, 30 mmol), which were dissolved in 105 ml anhydrous methanol and 105 ml anhydrous dichloromethane. Pyridine (4.74 g, 60 mmol) was added to the mixture. Under the nitrogen protection, elemental iodine (7.61 g, 30 mmol) was added to the mixture in portions. After the addition, the reaction was stirred at room temperature for 2-5 hours. Insoluble material was filtered off upon TLC detection showed the reaction was completed, and the filtrate was concentrated to dryness. The residue was dissolved in a small amount of dichloromethane, washed with saturated brine, concentrated, purified by column chromatography, and dried in vacuo to afford product 3.42 g in a yield of 32.7%.

Step 2: Synthesis of (R)-9-{2-[(hexadecyldisulfanylpropyl)phosphorylmethoxy]propyl}adenine (Compound 22)

To a reaction flask was added Compound 2 (2.43 g, 6.44 mmol), which was dissolved in 20 ml anhydrous dichloromethane. Under the nitrogen protection, the reaction was cooled to 0° C., and a solution of Compound 21 (2.69 g, 7.73 mmol) and pyridine (3.05 g, 38.64 mmol) in anhydrous dichloromethane was slowly added to the mixture dropwise. After the addition, the reaction was reacted at the low temperature for 10 minutes and warmed to rt and reacted for 2 hours. Upon MS monitoring showed the reaction was completed, 1 M dilute hydrochloric acid (30 ml) was added to quench the reaction, and the reaction was stirred at room temperature overnight. The organic phase was separated upon MS monitoring showed the reaction was completed. The aqueous phase was extracted 2-3 times with dichloromethane. The organic phase was combined, washed with saturated brine, concentrated, and purified by silica gel column chromatography to afford 2.67 g of product in a yield of 67.2%. LC-MS(APCI): m/z=618.5 $(M+1)^+$.

Step 3: Synthesis of (R)-9-{2-[(hexadecyldisulfanylpropyl)(isopropylcarbonatemethyl)phosphorylmethoxy]propyl}adenine (Compound T-19)

To a reaction flask were added Compound 22 (1.0 g, 1.62 mmol), chloromethyl isopropyl carbonate (1.23 g, 8.1 mmol), potassium carbonate (1.12 g, 8.1 mmol) and potassium iodide (134.5 mg, 0.81 mmol). 15 ml DMF was added to the mixture. The reaction was heated to 60° C. and reacted overnight. The reaction was cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 163 mg of product in a yield of 13.7%. LC-MS(APCI): m/z=734.1 $(M+1)^+$. $^1$H NMR (400 MHz, CDCl$_3$) δ 8.34 (s, 1H), 8.03 (s, 1H), 6.06 (s, 2H), 5.61 (m, 2H), 4.92 (dd, J=13.2, 6.6 Hz, 1H), 4.40-4.12 (m, 4H), 3.92 (dd, J=11.5, 7.1 Hz, 2H), 3.68 (t, J=10.0 Hz, 1H), 2.87 (dt, J=19.2, 6.7 Hz, 2H), 2.67 (dd, J=11.8, 7.0 Hz, 2H), 1.82-1.64 (m, 4H), 1.33-1.22 (m, 35H), 0.87 (t, J=6.6 Hz, 3H).

Example 22

(2'R,1'S)-9-{2-[(hexadecyldisulfanylpropyl)(isopropoxycarbonyl-1-ylethylamino)phosphorylmethoxy]propyl}adenine (Compound T-20)

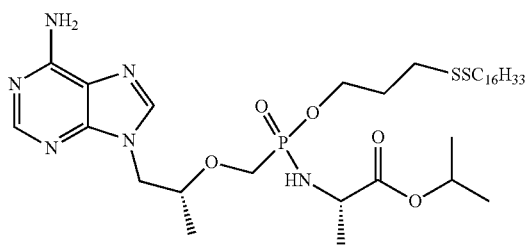

The following synthetic route was used for the synthesis:

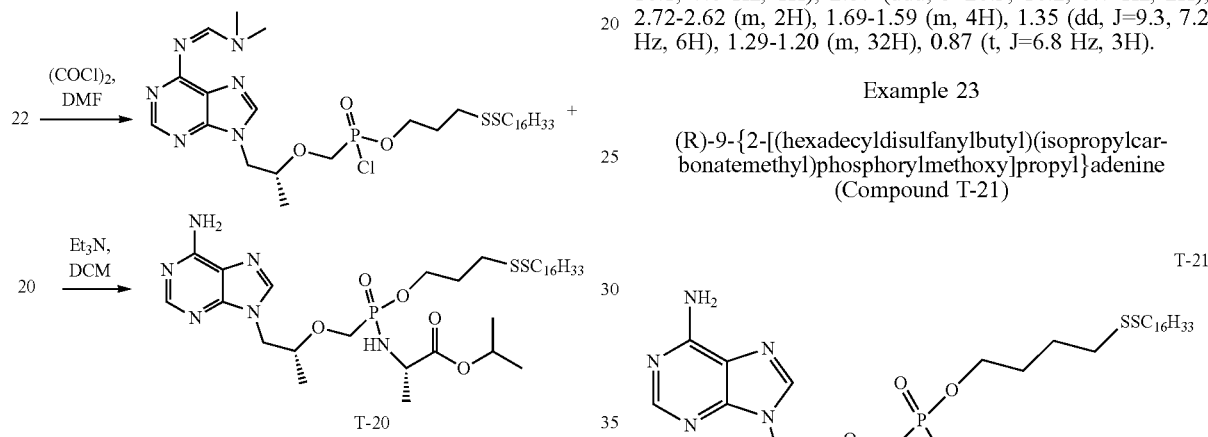

To a reaction flask were added Compound 22 (1.02 g, 1.66 mmol) and anhydrous DMF (145.6 mg, 1.99 mmol), which were dissolved in 20 ml anhydrous dichloromethane. Oxalyl chloride (4.14 ml, 8.28 mmol) was slowly added to the mixture dropwise at room temperature. After the addition, the reaction was stirred for 2-3 hours under the nitrogen protection. The reaction was concentrated to remove the solvent and excess oxalyl chloride, which were dissolved in 20 ml anhydrous dichloromethane. The reaction was cooled to 0° C. Under the nitrogen protection, a solution of Compound 20 (871 mg, 6.64 mmol) and triethylamine (837.8 mg, 8.28 mmol) in dichloromethane was slowly added to the mixture dropwise. After the addition, the reaction was warmed to rt and reacted for 1 hour. Upon TLC detection showed the reaction was completed, 3 ml ethanolamine was added to the mixture, which was stirred overnight. The mixture was diluted with a small amount of water. The organic phase was separated, washed 3 times with saturated brine, concentrated, and purified by silica gel column chromatography to afford 167 mg of product in a yield of 13.8%. LC-MS(APCI): m/z=731.7 (M+1)$^+$. $^1$H NMR (400 MHz, CDCl$_3$) δ 8.34 (d, J=4.4 Hz, 1H), 7.99 (d, J=12.2 Hz, 1H), 5.76 (d, J=7.0 Hz, 2H), 4.97 (ddt, J=44.7, 12.5, 6.3 Hz, 1H), 4.38 (ddd, J=19.6, 14.4, 3.0 Hz, 1H), 4.26-4.07 (m, 3H), 4.02-3.90 (m, 2H), 3.86-3.76 (m, 1H), 3.56 (ddd, J=13.2, 10.1, 7.6 Hz, 1H), 2.87 (ddd, J=20.3, 10.2, 5.7 Hz, 2H), 2.72-2.62 (m, 2H), 1.69-1.59 (m, 4H), 1.35 (dd, J=9.3, 7.2 Hz, 6H), 1.29-1.20 (m, 32H), 0.87 (t, J=6.8 Hz, 3H).

Example 23

(R)-9-{2-[(hexadecyldisulfanylbutyl)(isopropylcarbonatemethyl)phosphorylmethoxy]propyl}adenine (Compound T-21)

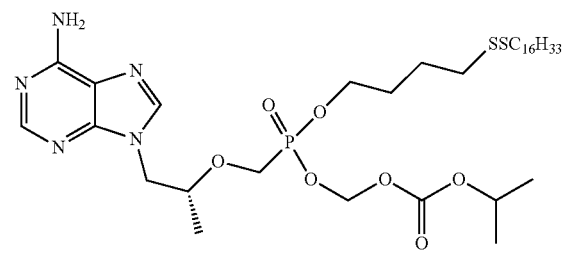

The following synthetic route was used for the synthesis:

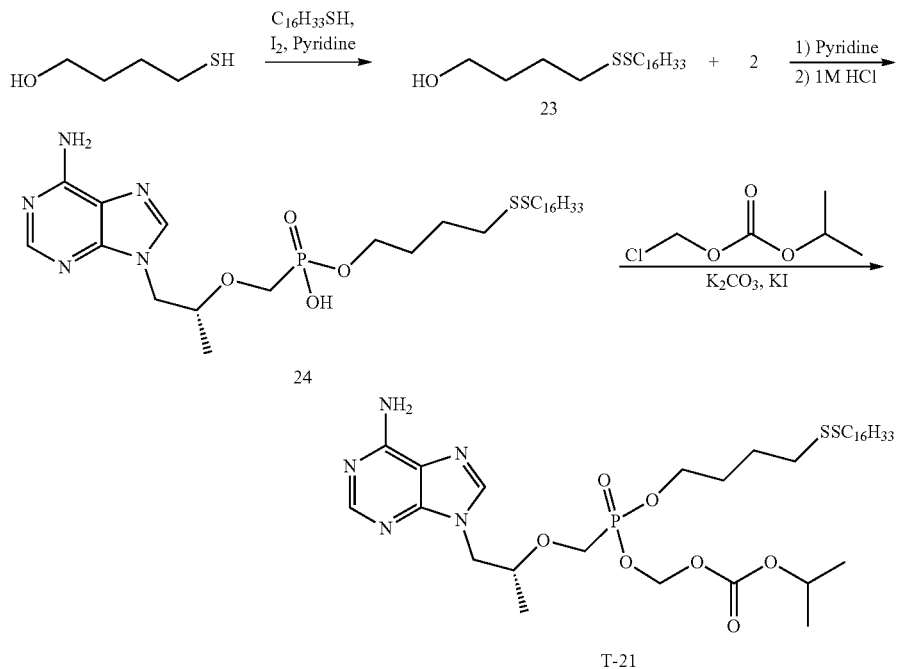

Step 1: Synthesis of 4-(hexadecyldisulfanyl)butanol (Compound 23)

To a reaction flask were added 4-mercaptobutanol (2.12 g, 20 mmol), and n-hexadecanethiol (5.16 g, 20 mmol), which were dissolved in 70 ml anhydrous methanol and 70 ml anhydrous dichloromethane. Pyridine (3.16 g, 40 mmol) was added. Under the nitrogen protection, elemental iodine (5.08 g, 20 mmol) was added to the mixture in portions. After the addition, the reaction was stirred at room temperature for 2-5 hours. Insoluble material was filtered off upon TLC detection showed the reaction was completed, and the filtrate was concentrated to dryness. The residue was dissolved in a small amount of dichloromethane, washed with saturated brine, concentrated, purified by column chromatography, and dried in vacuo to afford product 2.8 g in a yield of 38.7%.

Step 2: Synthesis of (R)-9-{2-[(hexadecyldisulfanylbutyl)phosphorylmethoxy]propyl}adenine (Compound 24)

To a reaction flask was added Compound 2 (2.43 g, 6.44 mmol), which was dissolved in 20 ml anhydrous dichloromethane. Under the nitrogen protection, the reaction was cooled to 0° C., and a solution of Compound 23 (2.8 g, 7.73 mmol) and pyridine (3.05 g, 38.64 mmol) in anhydrous dichloromethane was slowly added to the mixture dropwise. After the addition, the reaction was reacted at the low temperature for 10 minutes and warmed to rt and reacted for 2 hours. Upon MS monitoring showed the reaction was completed, 1 M dilute hydrochloric acid (30 ml) was added to quench the reaction, and the mixture was stirred at room temperature overnight. Upon MS monitoring showed the reaction was completed, the organic phase was separated. The aqueous phase was extracted 2-3 times with dichloromethane. The organic phase was combined, washed with saturated brine, concentrated, and purified by silica gel column chromatography to afford 2.99 g of product in a yield of 73.6%. LC-MS(APCI): m/z=632.6 (M+1)$^+$.

Step 3: Synthesis of (R)-9-{2-[(hexadecyldisulfanylbutyl)(isopropylcarbonatemethyl)phosphorylmethoxy]propyl}adenine (Compound T-21)

To a reaction flask were added Compound 24 (500 mg, 0.79 mmol), chloromethyl isopropyl carbonate (602 mg, 3.96 mmol), potassium carbonate (547.3 mg, 3.96 mmol) and potassium iodide (65.7 mg, 0.4 mmol). 10 ml DMF was added to the mixture. The reaction was heated to 60° C. and reacted overnight, and cooled to room temperature upon TLC detection showed the reaction was completed. The mixture was diluted with excess amount of water, and extracted 3-4 times with ethyl acetate. The organic phase was combined, washed with saturated brine, concentrated, and purified by silica gel column chromatography to afford 103 mg of product in a yield of 17.4%. LC-MS(APCI): m/z=748.5 (M+1)$^+$. $^1$H NMR (400 MHz, CDCl$_3$) δ 8.34 (s, 1H), 8.03 (s, 1H), 6.06 (s, 2H), 5.61 (m, 2H), 4.92 (dd, J=13.2, 6.6 Hz, 1H), 4.40-4.12 (m, 4H), 3.92 (dd, J=11.5, 7.1 Hz, 2H), 3.68 (t, J=10.0 Hz, 1H), 2.87 (dt, J=19.2, 6.7 Hz, 2H), 2.67 (dd, J=11.8, 7.0 Hz, 2H), 1.75-1.62 (m, 6H), 1.33-1.22 (m, 35H), 0.87 (t, J=6.6 Hz, 3H).

Example 24

(2'R,1'S)-9-{2-[(hexadecyldisulfanylbutyl)(isopropoxycarbonyl-1-ylethylamino)phosphorylmethoxy]propyl}adenine (Compound T-22)

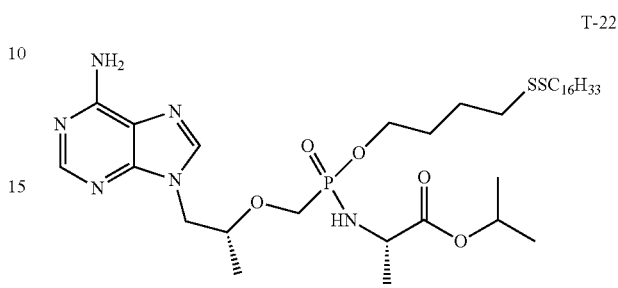

The following synthetic route was used for the synthesis:

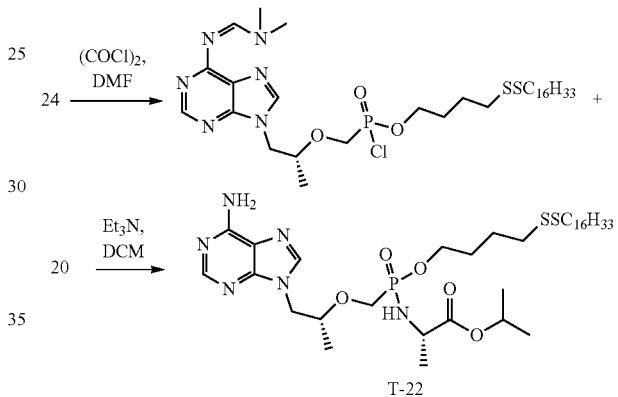

To a reaction flask were added Compound 24 (700 mg, 1.11 mmol) and anhydrous DMF (97.4 mg, 1.33 mmol), which were dissolved in 15 ml anhydrous dichloromethane. Oxalyl chloride (2.77 ml, 5.54 mmol) was slowly added to the mixture dropwise at room temperature. After the addition, the reaction was stirred for 2-3 hours under the nitrogen protection, and concentrated to remove the solvent and excess oxalyl chloride. The residue was dissolved in 15 ml anhydrous dichloromethane. The reaction was cooled to 0° C., and a solution of Compound 20 (726.7 mg, 5.54 mmol) and triethylamine (560.6 mg, 5.54 mmol) in dichloromethane was slowly added to the mixture dropwise under the nitrogen protection. After the addition, the reaction was warmed to rt and reacted for 1 hour. Upon TLC detection showed the reaction was completed, 2 ml ethanolamine was added to the mixture, which was stirred overnight. The mixture was diluted with a small amount of water. The organic phase was separated, washed 3 times with saturated brine, concentrated, and purified by silica gel column chromatography to afford 149 mg of product in a yield of 18.0%. LC-MS(APCI): m/z=745.1 (M+1)$^+$. $^1$H NMR (400 MHz, CDCl$_3$) δ 8.34 (d, J=4.4 Hz, 1H), 7.99 (d, J=12.2 Hz, 1H), 5.76 (d, J=7.0 Hz, 2H), 4.97 (ddt, J=44.7, 12.5, 6.3 Hz, 1H), 4.38 (ddd, J=19.6, 14.4, 3.0 Hz, 1H), 4.26-4.07 (m, 3H), 4.02-3.90 (m, 2H), 3.86-3.76 (m, 1H), 3.56 (ddd, J=13.2, 10.1, 7.6 Hz, 1H), 2.87 (ddd, J=20.3, 10.2, 5.7 Hz, 2H), 2.72-2.62 (m, 2H), 1.72-1.55 (m, 6H), 1.35 (dd, J=9.3, 7.2 Hz, 6H), 1.29-1.20 (m, 32H), 0.87 (t, J=6.8 Hz, 3H).

Biological Activity Test
(1) Detection of In Vitro Anti-HIV Activity of Compounds The data was analyzed by GraphPad Prism software, and the curve was fitted and $EC_{50}$ and $CC_{50}$ values were calculated. $EC_{50}$ refers to the effective concentration that inhibits 50% virus production, 50% virus infectivity, or 50% virus-induced cellular effects. $CC_{50}$ refers to the inhibitory concentration that reduces the cell growth or viability of uninfected cells by 50%.

Compound treatment: the test compounds and the reference compounds were 2-fold diluted with DMSO and added to the cell culture plate. The test compounds and the reference compounds were tested at 8 concentrations in duplicate.

Viral infection and cell treatment: HIV-1 and MT-4 cells were co-incubated at 37° C., in an incubator with 5% $CO_2$ for 1 h. The infected cells were then seeded in a cell culture plate at a certain density. The final concentration of DMSO in the cell culture medium was 0.5%. The cells were incubated at 37° C., in an incubator with 5% $CO_2$ for 5 days. The cells tested in the cytotoxicity assay were uninfected MT-4 cells, and other test conditions were with the same as that of the antiviral activity assay.

The activity assay of the cell: the cell viability was tested by using cell viability assay reagent CellTiter-glo (Promega). The raw data was used for calculating the anti-HIV-1 activity and cytotoxicity of the Compounds. Dose-response curves of compounds and their $EC_{50}$ and $CC_{50}$ values were obtained by analysis with GraphPad Prism software, where A represents $EC_{50} \leq 5$ nM, B represents 5 nM$<EC_{50} \leq 20$ nM, C represents 20 nM$<EC_{50} \leq 50$ nM; D represents 100 nM$<CC_{50} \leq 500$ nM, E represents 500 nM$<CC_{50} \leq 1000$ nM, F represents 1000 nM$<CC_{50} \leq 5000$ nM, and G represents $CC_{50} > 5000$ nM (as shown in Table 1 below).

(2) Detection of Anti-HBV Activity of Compounds In Vitro

Experimental method: anti-HBV activity of compounds was detected by Bright-Glo (Promega) luciferase. The data was analyzed by GraphPad Prism software, and the curve was fitted and $EC_{50}$ and $CC_{50}$ values were calculated. $EC_{50}$ refers to the effective concentration that inhibits 50% virus production, 50% virus infectivity, or 50% virus-induced cellular effects. $CC_{50}$ refers to the inhibitory concentration that reduces the cell growth or viability of uninfected cells by 50%.

Experimental Steps

Anti-cell viability assay: in vitro anti-hepatitis b virus activity of Example compounds was tested in HepG2.2.15 cells with TDF as a positive control compound. Cells were seeded into a 96-well plate on the first day; the compounds were added to treat the cells on the next day; and a new culture medium containing the compounds was replaced on the fifth day. On the eighth day, the supernatant was collected for DNA extraction. The content of HBV DNA was detected by quantitative PCR. Both test compound and TDF were subjected to a 3-fold serial dilution to get 8 concentration points in duplicate. The final concentration of DMSO in the culture medium was 0.5%. The formula for calculating the percentage of inhibition is as follows:

Inhibition rate=(1−copy number of HBV in sample/copy number of HBV in DMSO control group)×100%

$EC_{50}$ is analyzed by Graphpad Prism software (four parameter logistic equations), wherein I represents $EC_{50} \leq 15$ nM, II represents 15 nM$\leq EC_{50} \leq 50$ nM, III represents 50 nM$<EC_{50} \leq 100$ nM, IV represents 100 nM$<EC_{50} \leq 400$ nM (as shown in Table 1 below).

Cytotoxicity experiments: the arrangement of compounds on plate and compound-treatment process were the same as that of anti-HIV activity. Six days after the cells were treated by compounds, the cell activity was tested. Cell-titer Blue reagent was added to each well, the cells were incubated at 37° C. for 3 hours, and fluorescence values were read (560Ex/590 Em). The data were analyzed and the relative cell viability was calculated:

The percentage of cell viability was calculated using the following formula:

% cell viability=(fluorescence reading of sample−fluorescence reading of culture control)/(fluorescence reading of DMSO control−fluorescence reading of culture control)×100.

Finally, the $CC_{50}$ value of the compounds were calculated by the GraphPad Prism software. V represents 10000 nM$<CC_{50} \leq 50000$ nM, VI represents $CC_{50} > 50000$ nM (as shown in Table 1 below).

TABLE 1

HBV activity and HIV activity of example compounds

| Compound No. | HIV activity and cytotoxicity data | | HBV activity and cytotoxicity data | |
|---|---|---|---|---|
| | $EC_{50}$ (nM) | $CC_{50}$ (nM) | $EC_{50}$ (nM) | $CC_{50}$ (nM) |
| T-1 | C | F | IV | VI |
| T-2 | A | F | III | VI |
| T-3 | A | F | I | VI |
| T-3-1 | A | D | IV | VI |
| T-3-2 | A | D | IV | VI |
| T-4 | B | G | II | VI |
| T-5 | A | F | III | VI |
| T-6 | A | E | III | VI |
| T-7 | A | D | II | VI |
| T-8 | B | E | II | VI |
| T-9 | A | E | II | VI |
| T-10 | A | D | III | VI |
| T-11 | A | F | I | VI |
| T-12 | A | F | III | VI |
| T-13 | A | F | II | VI |
| T-14 | A | E | III | VI |
| T-15 | B | F | I | V |
| T-16 | B | F | I | VI |
| T-17 | B | E | I | VI |
| T-18 | C | F | IV | VI |
| T-19 | A | G | IV | VI |
| T-20 | B | F | II | V |
| T-21 | C | G | IV | VI |
| T-22 | B | G | I | V |

Experimental results show that the compounds disclosed herein have strong anti-HIV activity and anti-HBV activity (both in nanomolar levels). In addition, in the cell lines tested, the compounds disclosed herein do not show toxicity (the preferable $CC_{50} > 50000$ nM).

(3) Liver Microsomal Metabolism Experiment

Microsomal experiments: human liver microsomes: 0.5 mg/mL, Xenotech; rat liver microsomes: 0.5 mg/mL, Xenotech; coenzyme (NADPH/NADH): 1 mM, Sigma Life Science; magnesium chloride: 5 mM, 100 mM phosphate buffer (pH 7.4).

Preparation of stock solution: powder of Example compounds were precisely weighed and dissolved in DMSO to 5 mM.

Preparation of phosphate buffer (100 mm, pH 7.4): 0.5M pre-formulated potassium dihydrogen phosphate (150 ml) and 0.5M potassium hydrogen phosphate (700 ml) were mixed well. The pH of the mixture was then adjusted to 7.4 with 0.5M potassium hydrogen phosphate solution. The resulting solution was 5-fold diluted with ultrapure water before use, and magnesium chloride was added to the solution, affording a phosphate buffer (100 mm), containing potassium phosphate (100 mM), magnesium chloride (3.3 mM), pH 7.4.

A NADPH regeneration system solution (containing 6.5 mM NADP, 16.5 mM G-6-P, 3 U/mL G-6-P D, 3.3 mM magnesium chloride) was formulated, which was placed on wet ice before use.

Preparation of stop solution: 50 ng/mL of propranolol hydrochloride and 200 ng/mL of tolbutamide (internal standard) in acetonitrile. 25057.5 μL of phosphate buffer (pH 7.4) was placed to a 50 mL centrifuge tube, and 812.5 μL human liver microsomes were added to the tube, which were mixed well to give a protein concentration of 0.625 mg/mL liver microsomes diluent. 25057.5 μL of phosphate buffer (pH 7.4) was placed to a 50 ml centrifuge tube, and 812.5 μL SD rat liver microsomes were added to the tube, which were mixed well to give a protein concentration of 0.625 mg/mL liver microsomes diluent.

Incubation of the sample: the stock solution of the corresponding compounds was diluted to 0.25 mM with 70% acetonitrile in water as a working solution for later use. 398 μL of human liver microsomes dilution or rat liver microsomes dilution was added into 96-well incubation plate (N=2), and 2 μL of 0.25 mM working solution was added to the plate, which were mixed well.

Metabolic stability assay: 300 μL of pre-chilled stop solution was added to each well of a 96-well deep-well plate and the plate was placed on ice as a stop plate. The 96-well incubation plate and NADPH regeneration system were placed in a 37° C. water bath, shaked at 100 rpm, pre-incubated for 5 min. 80 μL of incubation solution was taken from each well of the incubation plate and was added to the stop plate, which were mixed well. 20 μL of NADPH regeneration system solution was supplemented into the mixture to form the 0 min sample. Then 80 μL of NADPH regeneration system solution was added to each well of the incubation plate to initiate the reaction and start timing. The reaction concentration of the corresponding compound was 1 μM, and the protein concentration was 0.5 mg/mL. At 10, 30, and 90 min, 100 μL of the reaction solution was added to the stop plate and vortexed for 3 min to quench the reaction. The stop plate was centrifuged at 5000×g at 4° C. for 10 min. 100 μL of supernatant was taken into a 96-well plate containing 100 μL of distilled water, which were mixed well. LC-MS/MS was used for sample analysis.

Data analysis: The peak area of the corresponding compounds and internal standard was detected by LC-MS/MS system, and the peak area ratio of compounds to internal standard was calculated. The slope was measured by plotting the natural log of the percentage of the remaining amount of the compounds versus time, and $t_{1/2}$ and $CL_{int}$ were calculated according to the following formula, where V/M is equal to 1/protein concentration.

$$t_{1/2} = -\frac{0.693}{\text{slope}}, \quad CL_{int} = \frac{0.693}{t_{1/2}} \cdot \frac{V}{M}$$

The compounds disclosed herein were tested in the above microsome experiment and it was found that the compounds disclosed herein have superior metabolic stability. The results of the human liver microsome experiment and the rat liver microsome experiment of representative examples are summarized in Table 2 below.

TABLE 2

Evaluation of liver microsome metabolism of Example compounds

| No. | Human liver microsome experiment | | Rat liver microsome experiment | |
|---|---|---|---|---|
| | $t_{1/2}$(min) | $CL_{int}$ (μL/min/mg) | $t_{1/2}$(min) | $CL_{int}$ (μL/min/mg) |
| T-2 | 37.3 | 37.2 | 43.6 | 31.8 |
| T-3 | 79.8 | 17.4 | 37.4 | 37.0 |
| T-3-2 | 19.5 | 71.0 | 25.5 | 54.4 |
| T-4 | | | 192.2 | 7.2 |
| T-5 | 19.1 | 72.6 | 16.8 | 82.3 |
| T-6 | 22.3 | 62.1 | 24.5 | 56.5 |
| T-7 | 26.8 | 51.7 | 49.3 | 28.1 |
| T-8 | 67.5 | 20.5 | 48.2 | 28.8 |
| T-9 | 124.2 | 11.2 | 103.9 | 13.3 |
| T-10 | 58.3 | 23.8 | 55.2 | 25.1 |
| T-11 | 175.4 | 7.9 | 78.9 | 17.6 |
| T-12 | 216.2 | 6.4 | 179.1 | 7.7 |
| T-13 | 108.0 | 12.8 | 77.8 | 17.8 |
| T-14 | 1509 | 0.92 | 241.1 | 5.7 |
| T-15 | 9.2 | 149.9 | 8.4 | 164.5 |
| T-16 | 11.5 | 120.6 | 12.5 | 110.8 |
| T-17 | 54.4 | 25.5 | 69.6 | 19.9 |
| T-18 | 627.6 | 2.2 | 1117 | 1.24 |
| T-19 | 59.1 | 23.5 | 57.5 | 24.1 |
| T-20 | 115.9 | 12.0 | 128.3 | 10.8 |
| T-21 | 63.7 | 21.7 | 77.9 | 17.8 |
| T-22 | 225.7 | 6.1 | 636.9 | 2.2 |

The experimental results are shown in Table 2 above. The compounds disclosed herein have a longer half-life and a lower clearance rate. They show superior metabolic stability in human liver microsomes and rat liver microsomes, and are more suitable as drugs for anti-HIV and/or anti-HBV infection (4) Rat Pharmacokinetics Experimental purpose: To study the pharmacokinetic behavior of the compounds disclosed herein after they were administered to the rats.

Experimental Animals:
Species and strain: SD rats, grade: SPF grade
Gender and number: male, 6
Weight range: 180-220 g (actual body weight in the range of 187-197 g)
Source: Shanghai Sippr-BK laboratory animal Co. Ltd.
Assays and animal certification number: SCXK(Shanghai)2013-0016
Experiment Procedure:
Before the blood sample collection, 20 μL of 2M sodium fluoride solution (esterase inhibitor) was added to the EDTA-K2 anticoagulation tube, which was dried in an 80° C. oven and stored in a 4° C. refrigerator.
Rats, males, weighing 187 to 197 g, were randomly divided into 2 groups. They started fasting overnight in the afternoon before the experiment but were free to drink water. They were given food 4 hours after administration. The reference compounds (3 mg/kg) were administered to the rats in Group A, and the Example compound (3 mg/kg) was administered to the rats in group B. About 100-200 μL blood was taken from the orbital vein of rats at 15 min, 30 min, 1, 2, 3, 5, 8, and 10 h after administration, and placed in a 0.5 mL Eppendorf tube anti-coagulated with EDTA-K2, which were mixed immediately. After the anti-coagulation, the test tubes were inverted and mixed 5-6 times gently as soon as possible. Then the collected blood was placed in an ice box, and within 30 min, the blood sample was centrifuged at 4000 rpm, 4° C. for 10 min. All of the plasma were collected and stored at −20° C. immediately. After samples were collected at all above time points, the drug concentration in the plasma was determined at each time point.

From the resulting data of mean drug concentration in the plasma verse time after administration, Winnonin software was used to calculate the pharmacokinetics-related parameters of the male SD rats after they were i.g. administered the Example compounds (3 mg/kg) according to the non-compartment statistical moment theory.

Experiments show that the compounds disclosed herein have good activity and pharmacokinetic properties, and are more suitable compounds for inhibiting nucleoside reverse transcriptase, and thus they are suitable for preparing a drug for treating antiviral infection.

It should be understood, these examples are illustrative of the present invention and are not intended to limit the scope of the present invention. The experimental methods without specific conditions in the examples generally follow the conventional conditions or the conditions recommended by the manufacturer. Unless otherwise stated, parts and percentages are parts by weight and weight percent.

The foregoing is a further detailed description of the present invention in conjunction with specific preferred embodiments, and it cannot be assumed that the specific embodiment of the present invention is limited to these descriptions. For ordinary skilled in the art, without departing from the concept of the present invention, several simple deductions or replacements can also be made, which should be deemed to be within the scope of the present invention.

The invention claimed is:

1. A compound of Formula (I-1):

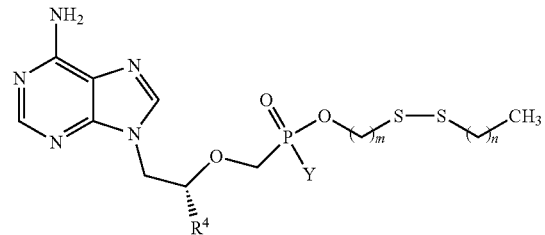

(I-1)

wherein,
$R^4$ is optionally substituted $C_1$-$C_6$ alkyl;
Y is selected from the following structures:

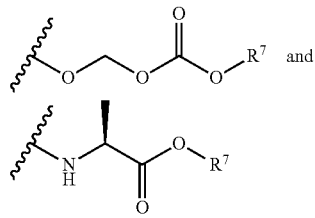

wherein, $R^7$ is selected from optionally substituted $C_1$-$C_6$ alkyl or optionally substituted $C_3$-$C_7$ carbocyclyl as valency permits;
m is 2 or 3;
n is 13 or 15;
or a pharmaceutically acceptable salt, a stereoisomer, a solvate, a hydrate, a polymorph, or an isotopic variant thereof.

2. The compound of claim 1, wherein $R^4$ is methyl.

3. The compound of claim 1, wherein
$R^7$ is selected from the following groups:
methyl, ethyl, n-propyl, isopropyl, n-butyl, s-butyl, isobutyl, t-butyl, n-pentyl, isopentyl, neopentyl, tert-pentyl, n-hexyl, 3-methylhexyl, 2,2-dimethylpentyl, 2,3-dimethylpentyl, cyclopropyl, cyclobutyl, cyclopentyl, cyclohexyl, and cycloheptyl.

4. The compound of claim 1, wherein m is 2.

5. The compound of claim 1, wherein n is 15.

6. The compound of claim 1, wherein the compound has a chirality at the phosphorus atom, and its configuration is selected from S-configuration, R-configuration or the mixture of S-configuration and R-configuration.

7. The compound of claim 1, which is selected from the following compounds:

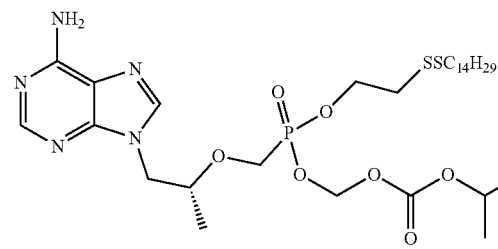

II-2

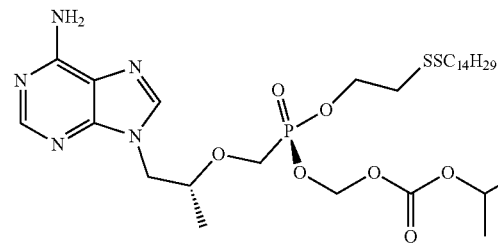

II-2-a

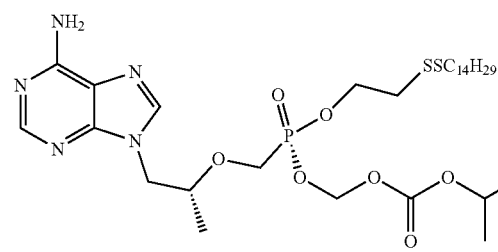

II-2-b

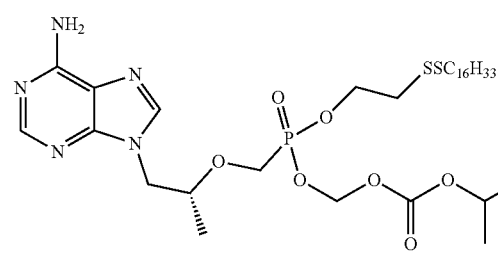

II-3

II-3-a
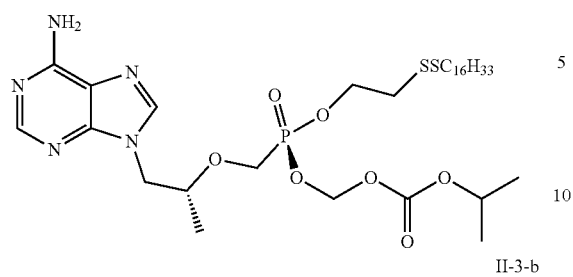
II-3-b
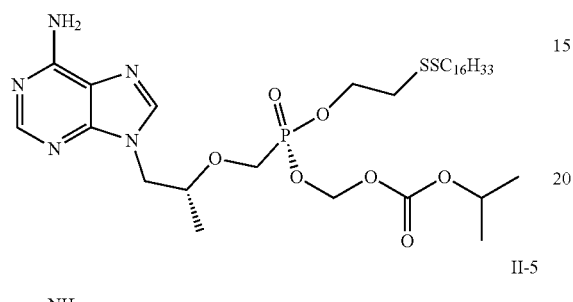
II-5
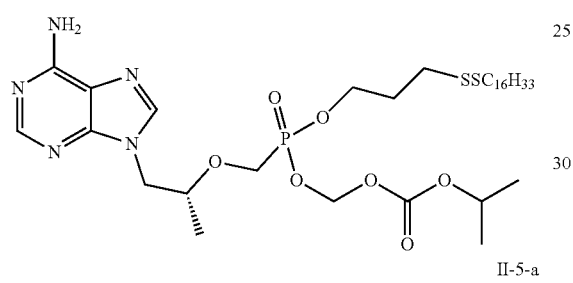
II-5-a
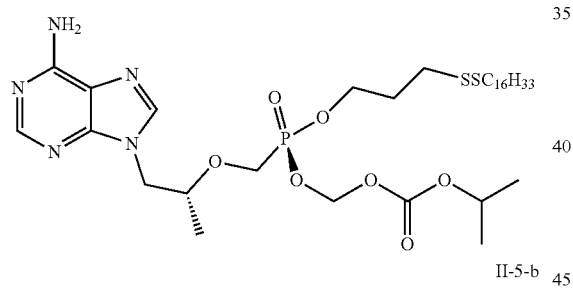
II-5-b
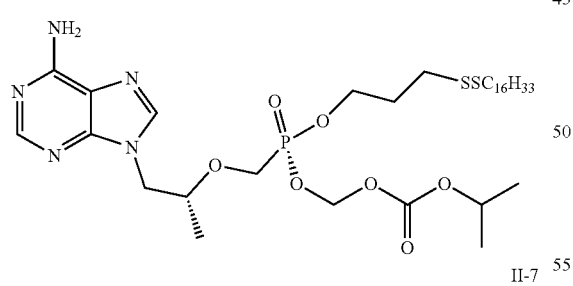
II-7
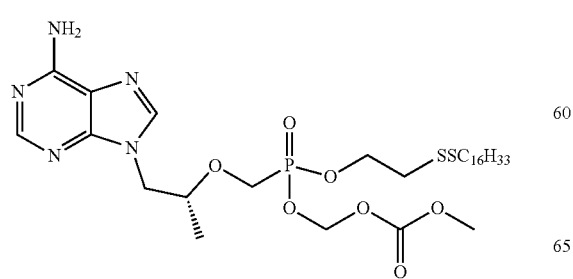
II-7-a
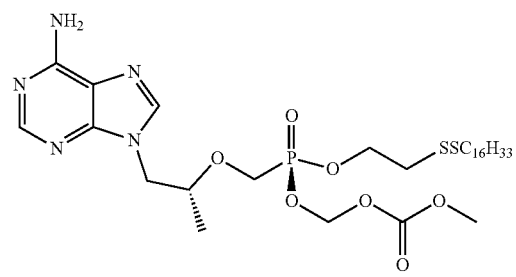
II-7-b
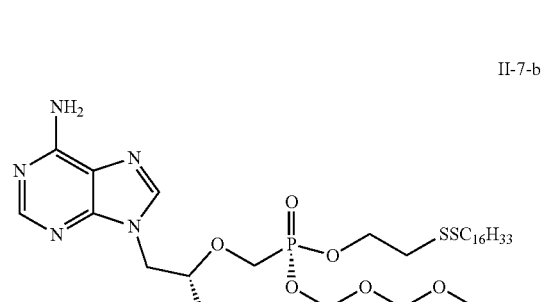
II-8
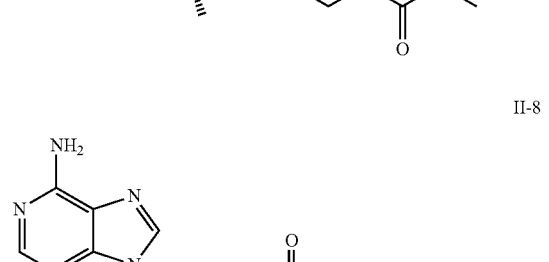
II-8-a
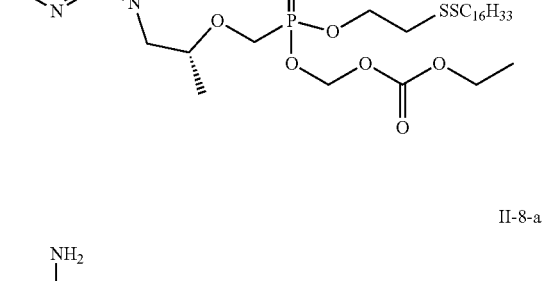
II-8-b
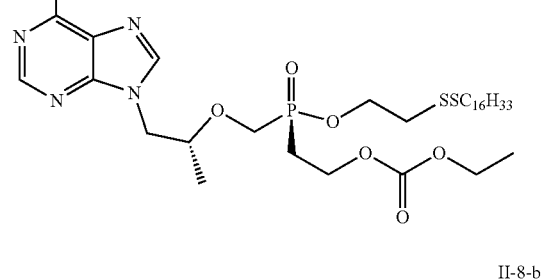
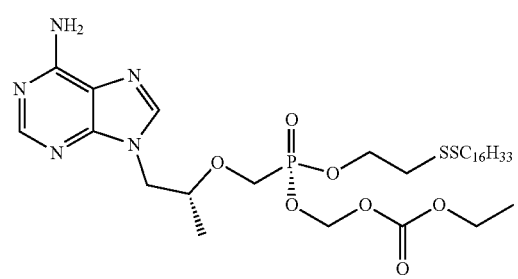

-continued
II-9
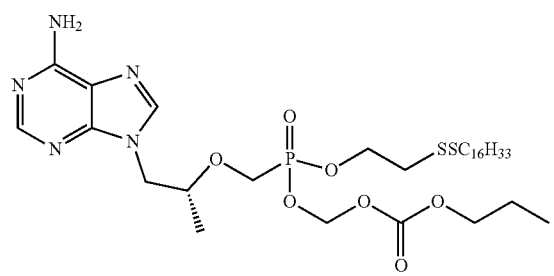
II-9-a
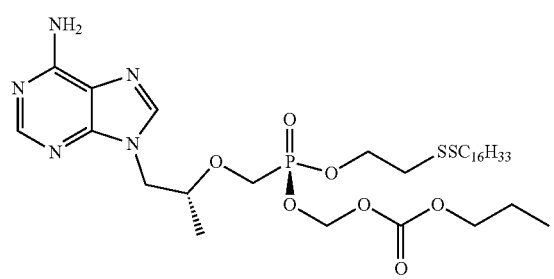
II-9-b
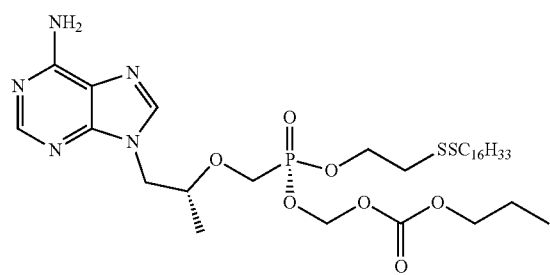
II-10
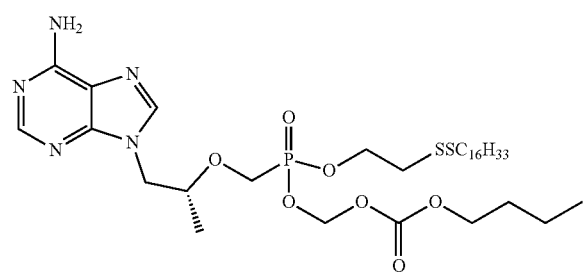
II-10-a
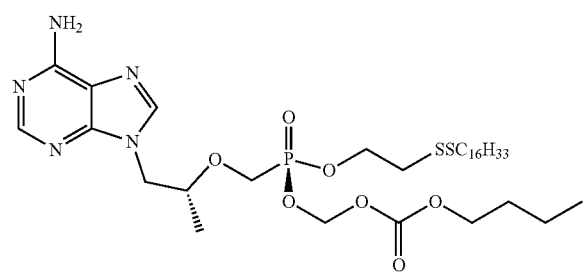
-continued
II-10-b
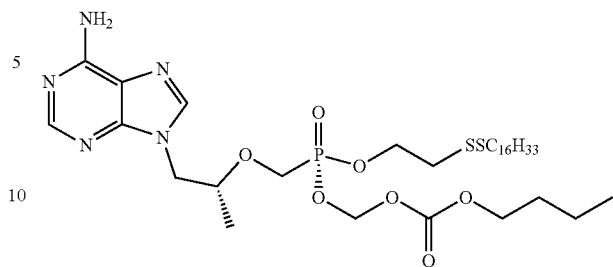
II-11
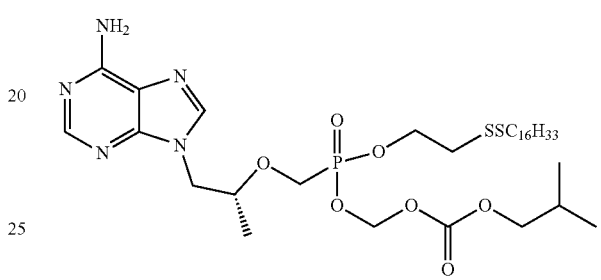
II-11-a
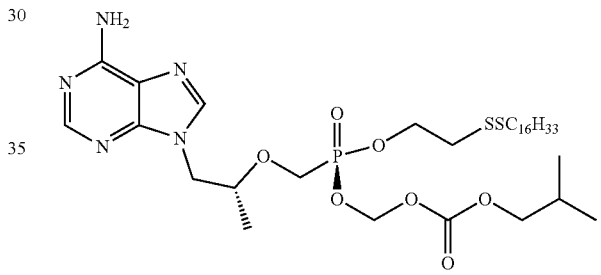
II-11-b
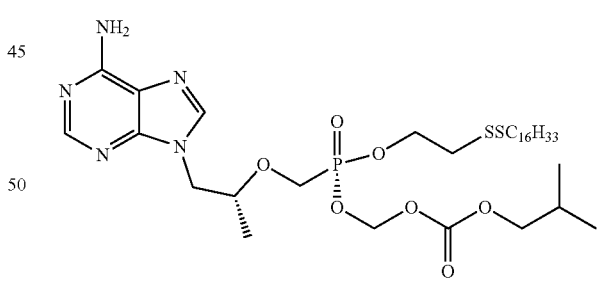
II-12
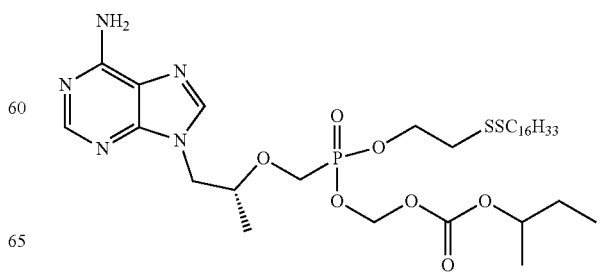

II-12-a
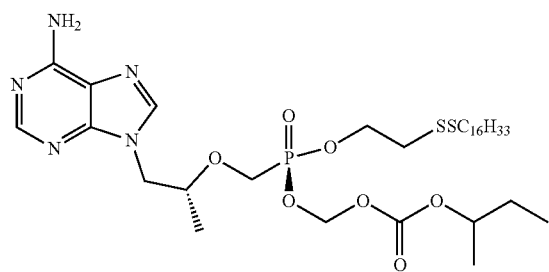
II-12-b
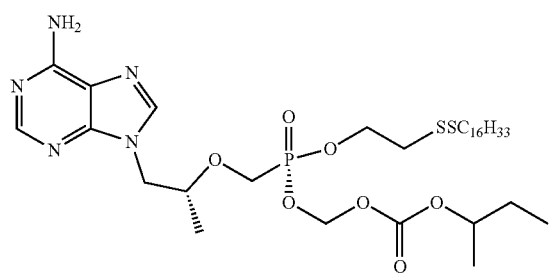
II-13
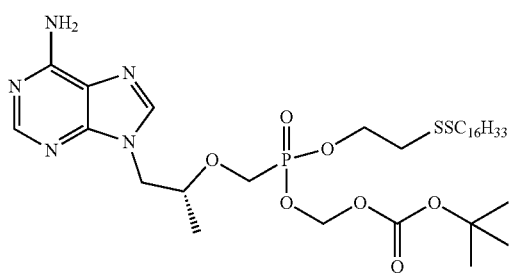
II-13-a
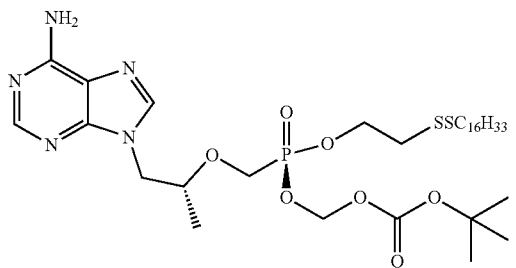
II-13-b
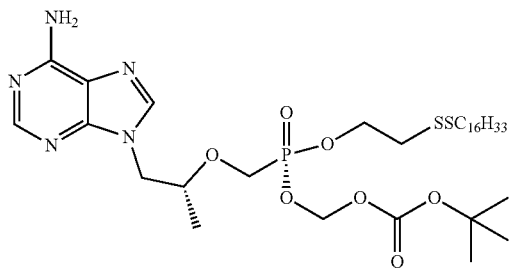
II-14
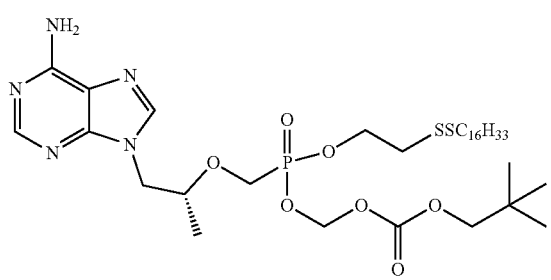
II-14-a
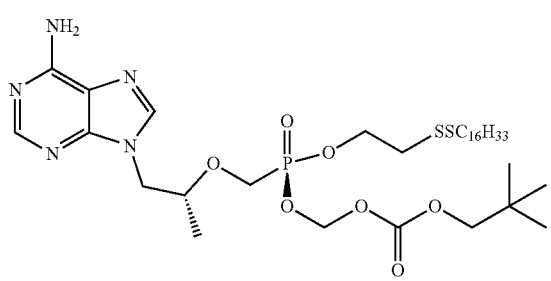
II-14-b
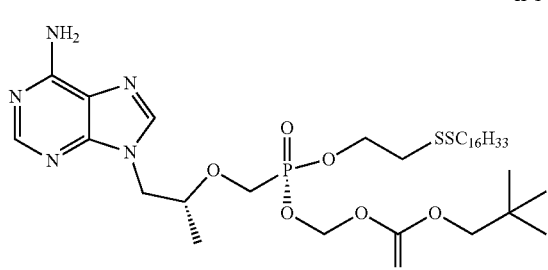
II-15
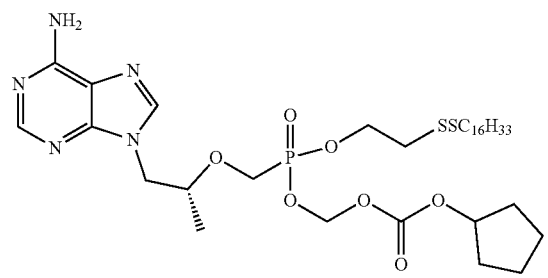
II-15-a
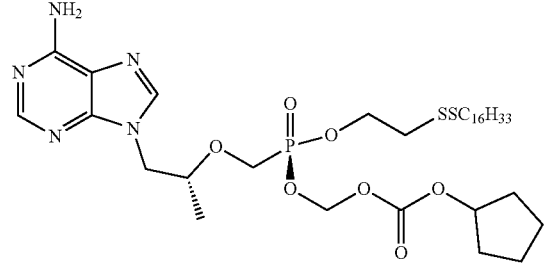

II-15-b
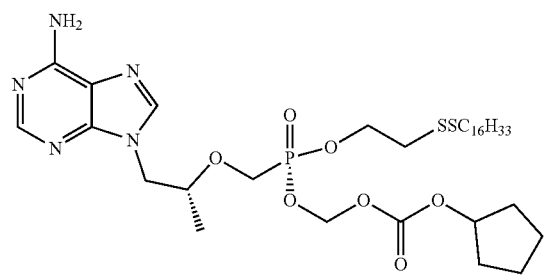
II-16
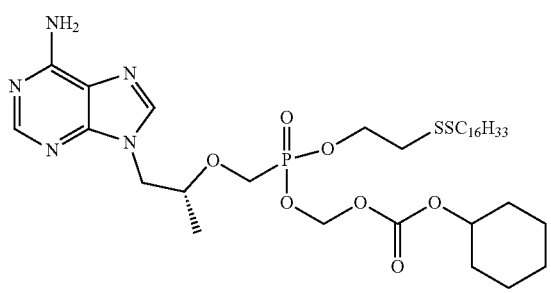
II-16-a
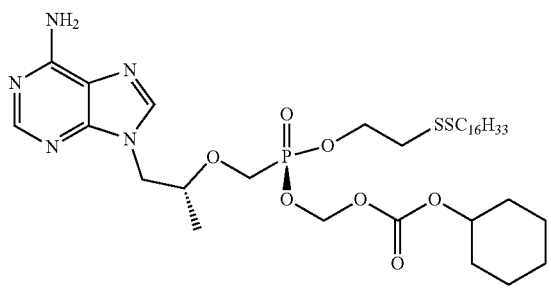
II-16-b
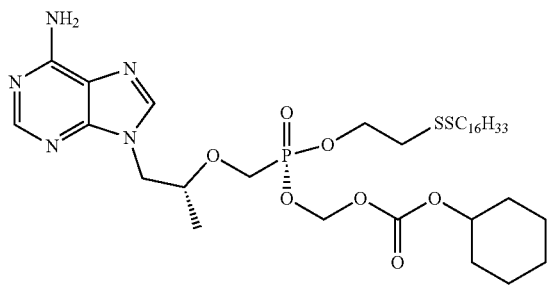
III-2
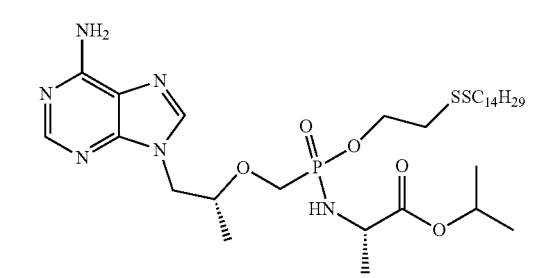
III-2-a
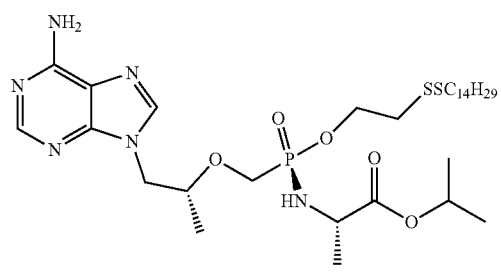
III-2-b
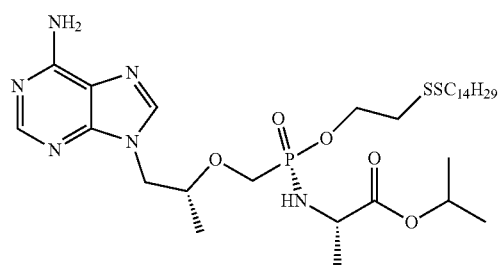
III-3
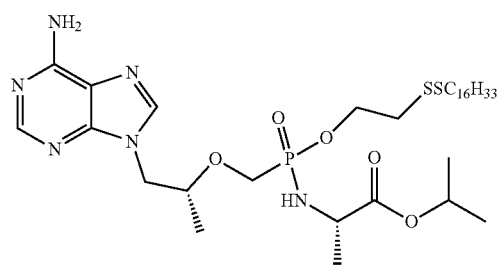
III-3-a
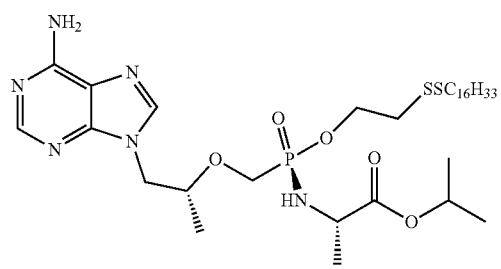
III-3-b
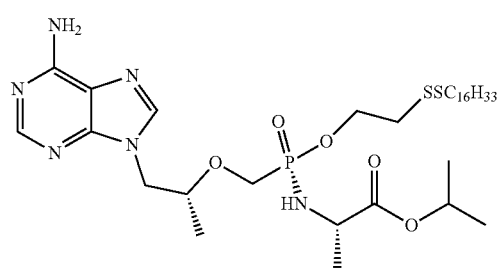

III-5

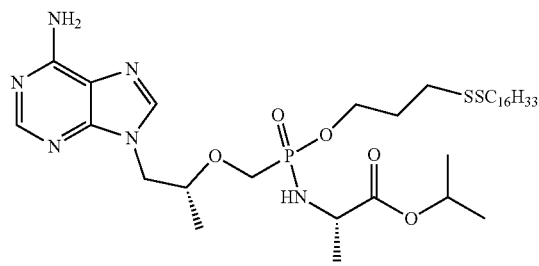

III-5-a

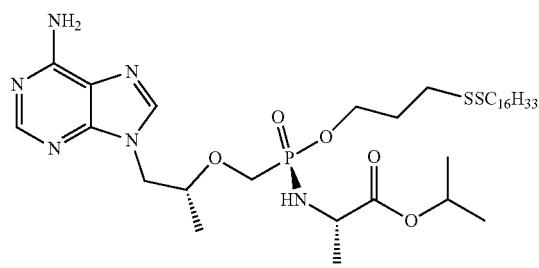

III-5-b

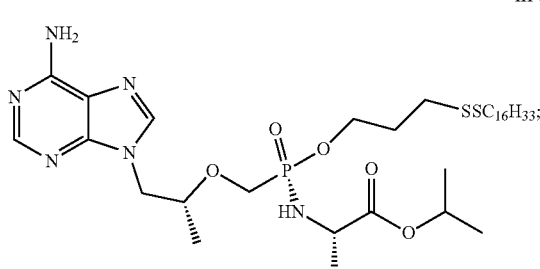

or a pharmaceutically acceptable salt, a stereoisomer, a solvate, a hydrate, a polymorph, or an isotopic variant thereof.

8. The compound of claim 1, wherein $R^7$ is selected from the following groups:

methyl, ethyl, n-propyl, isopropyl, n-butyl, s-butyl, isobutyl, t-butyl, neopentyl, cyclopentyl, and cyclohexyl.

9. The compound of claim 1, wherein $R^7$ is isopropyl.

10. A compound, which is selected from the following compounds:

II-4

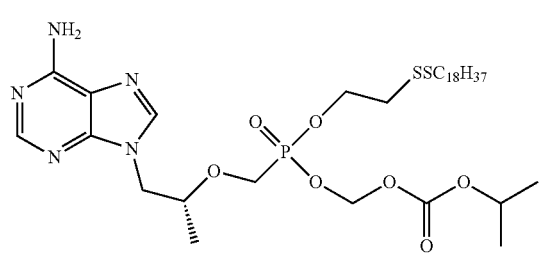

II-4-a

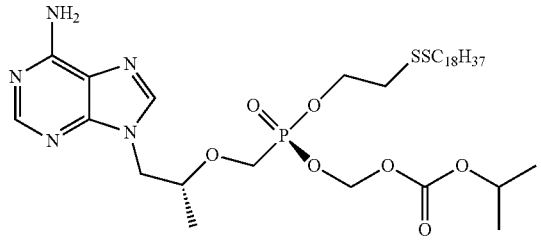

II-4-b

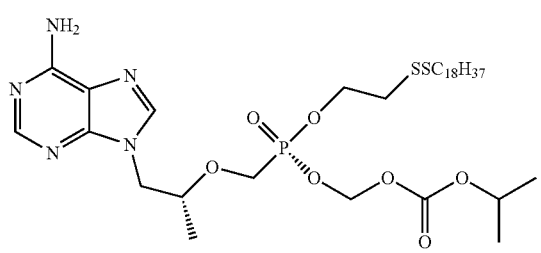

III-1

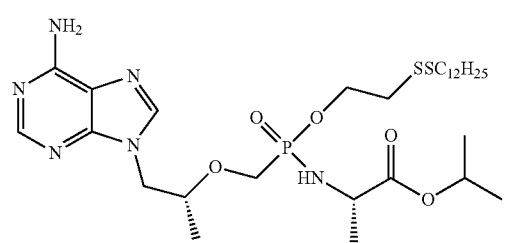

III-1-a

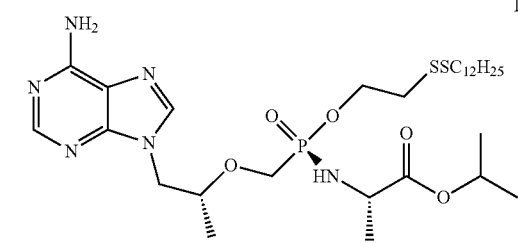

III-1-b

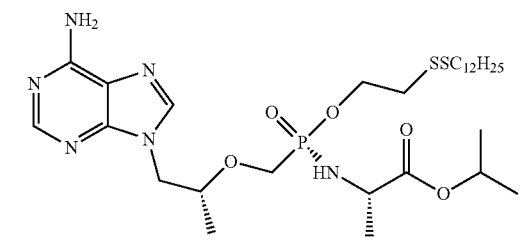

III-6

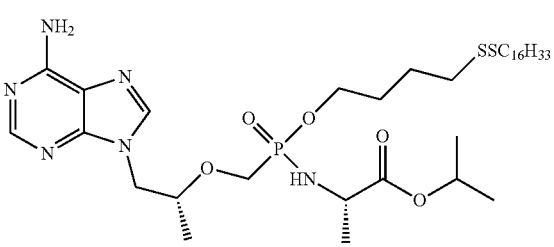

-continued

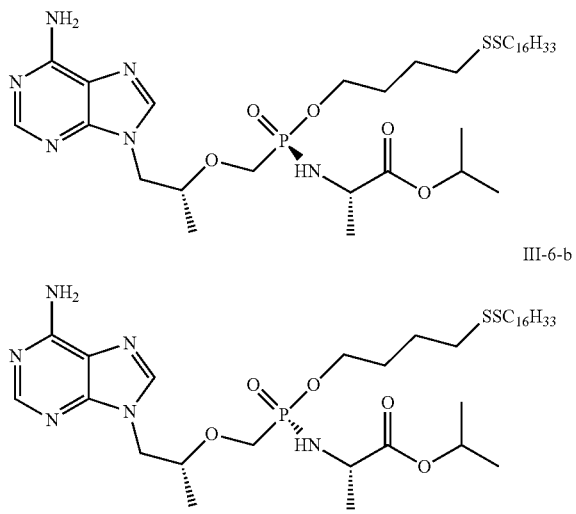

III-6-a

III-6-b or a pharmaceutically acceptable salt, a stereoisomer, a solvate, a hydrate, a polymorph, or an isotopic variant thereof.

11. A pharmaceutical composition, which comprises the compound of claim 1 or a pharmaceutically acceptable salt, a stereoisomer, a solvate, a hydrate, a polymorph, or an isotopic variant thereof, and pharmaceutically acceptable excipient(s).

12. The pharmaceutical composition of claim 11, which further comprises other therapeutic agent(s).

13. A kit, comprising:
   a first container comprising a compound of claim 1 or a pharmaceutically acceptable salt, a stereoisomer, a solvate, a hydrate, a polymorph, or an isotopic variant thereof; and
   optionally, a second container comprising other therapeutic agent(s); and
   optionally, a third container comprising a pharmaceutical excipient for diluting or suspending the compound and/or other therapeutic agent(s).

14. A method of treating viral infections in a subject, comprising administering to the subject the compound of claim 1 or a pharmaceutically acceptable salt, a stereoisomer, a solvate, a hydrate, a polymorph, or an isotopic variant thereof, wherein the viral infections is caused by human immunodeficiency virus (HIV) or hepatitis B virus (HBV).

* * * * *